(12) United States Patent
Lee et al.

(10) Patent No.: US 6,350,592 B1
(45) Date of Patent: Feb. 26, 2002

(54) AORTIC-SPECIFIC ENHANCER SEQUENCE AND USES THEREOF

(75) Inventors: Mu-En Lee, Newton; Chung-Ming Hsieh, Cambridge, both of MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/303,069

(22) Filed: Apr. 30, 1999

Related U.S. Application Data

(63) Continuation-in-part of application No. 09/134,250, filed on Aug. 14, 1998.

(51) Int. Cl.[7] .................. C07H 21/04; C12P 21/06; C12N 15/00; C12N 5/00; C12N 15/63
(52) U.S. Cl. .................. 435/69.1; 435/320.1; 435/455; 435/325; 536/23.1; 536/24.1
(58) Field of Search .................. 536/23.1, 24.1; 435/320.1, 69.1, 455, 325

(56) References Cited

U.S. PATENT DOCUMENTS

| | | | |
|---|---|---|---|
| 5,786,171 A | 7/1998 | Lee et al. | 435/69.1 |
| 5,846,773 A | * 12/1998 | Lee et al. | 435/69.1 |

FOREIGN PATENT DOCUMENTS

| | | |
|---|---|---|
| WO | WO 97/00953 | 1/1997 |
| WO | WO 98/35040 | 8/1998 |

OTHER PUBLICATIONS

Ausubel, F.M. et al. (1990) "Uses of Fusion Genes IN Mammalian Transfection" Current Protocols in Molecular Biology, Supplement 36 CPMB, pp. 9.6.1–9.6.12.
Yet, Shaw–Feng et al. (1998) "Molecular Cloning Characterization, and Promoter Analysis of the Mouse Crp2/SmLim Gene" The Journal of Biological Chemistry, vol. 273, No. 17, pp. 10530–10537.
Blobel et al., "Structure, Function and Evolutionary Relationship of Proteins Containing a Disintegrin Domain", *Curr. Opin. Cell Biol.*, 4:760–65 (1992).
Del Sal et al., "The Growth Arrest–Specific Gene, gas1, Is Involved in Growth Suppression", 1992, *Cell*, 70:595–607 (1992).
Gallagher et al., "The Carboxyl Terminus of the Smooth Muscle Myosin Light Chain Kinase is Expressed as an Independent Protein, Telokin", *J. Biol. Chem.*, 266:23945–52 (1991).
Gorski et al., "Molecular Cloning of a Diverged Homeobox Gene that is Rapidly Down–Regulated During the $G_0/G_1$ Transition in Vascular Smooth Muscle Cells", *Mol. and Cell. Biol.*, 13:3722–33 (1993).
Holden, et al., "X–ray Structure Determination of Tekokin, the C–terminal Domain of Myosin Light Chain Kinase, at 2·8 Å Resolution", *J. Mol. Biol.*, 277:840–51 (1992).

Hsieh et al., "APEG–1, a Novel Gene Preferentially Expressed in Aortic Smooth Muscle Cells, is Down–regulated by Vascular Injury," *FASEB J.* 10:6, p. A1012, No. 74 (1996).
Hsieh et al., "APEG–1, A Novel Gene Preferentially Expressed In Aortic Smooth Muscle Cells, is Down–regulated by Vascular Injury," *J. Biol. Chem. (Microfilms)* 271(29):17354–59 (1996).
Hunter et al., "Targeting Gene Expression to Specific Cardiovascular Cell Types in Transgenic Mice", *Hypertension*, 22:608–17 (1993).
Hynes, "Integrins: Versatility, Modulation, and Signaling in Cell Adhesion", *Cell*, 69:11–25 (1992).
Kozak, "At Lease Six Nucleotides Preceding the AUG Initiator Codon Enhance Translation in Mammalian Cells", *J. Mol. Biol.*, 196:947–50 (1987).
Leco et al., "Tissue Inhibitor of Metalloproteinases–3 (TIMP–3) Is an Extracellular Matrix–associated Protein with a Distinctive Pattern of Expression in Mouse Cells and Tissues", *J. Biol. Chem.*, 269:9352–60 (1994).
McGeoch et al., "Complete DNA Sequence of the Short Repeat Region in the Genome of Herpes Simplex Virus Type I," *Nucleic Acids Research* 14(4):1727–1745 (1986).
Pauly et al., "Experimental Models That Mimic the Differentiation and Dedifferentiation of Vascular Cells", *Circulation (Supp III)*, 86:III–68–73 (1992).
Ross, "The Pathogenesis of Atherosclerosis: A Perspecitve for the 1990s", *Nature*, 362:801–809 (1993).
Ruoslahti et al., "New Perspectives in Cell Adhesion: RGD and Integrins", *Science*, 238:491–96 (1987).
Shanahan et al., "Isolation of Gene Markers of Differentiated and proliferating Vascular Smooth Muscle Cells", *Circulation Res.*, 73:193–204 (1993).
Sun et al., "Molecular Cloning of Five Messenger RNAs Differentially Expressed in Preneoplastic or Neoplastic JB6 Mouse Epidermal Cells: One Is Homologous to Human Tissue Inhibitor of Metalloproteinases–3", *Cancer Res.*, 54:1139–44.
EMBL EST, Accession No. R24327, Sequence reference yg32f04.rl, Apr. 23, 1995, Homo sapiens cDNA clone 33988 5' XP002014921.
EMBL EST, Accession No. W55328, Sequence reference mb12e01.rl, Jun. 6, 1996, Life Tech mouse brain, Mus musculus cDNA clone 319992 5' XP002014922.

\* cited by examiner

*Primary Examiner*—David Guzo
*Assistant Examiner*—Gerald G. Leffers, Jr.
(74) *Attorney, Agent, or Firm*—Ingrid A. Beattie; Mintz, Levin, Cohn, Ferris, Glovsky and Popeo, P.C.

(57) ABSTRACT

Aortic-preferentially-expressed gene-1 (APEG-1) and striated muscle preferentially expressed (SPEG) polypeptide, DNA sequences encoding and controlling the transcription of the APEG-1/SPEG encoding gene, methods of diagnosing vascular injury, methods of conferring smooth muscle-cell specific expression, and methods of inhibiting vascular smooth muscle cell proliferation by increasing the level of APEG-1 at the site of vascular injury.

16 Claims, 31 Drawing Sheets

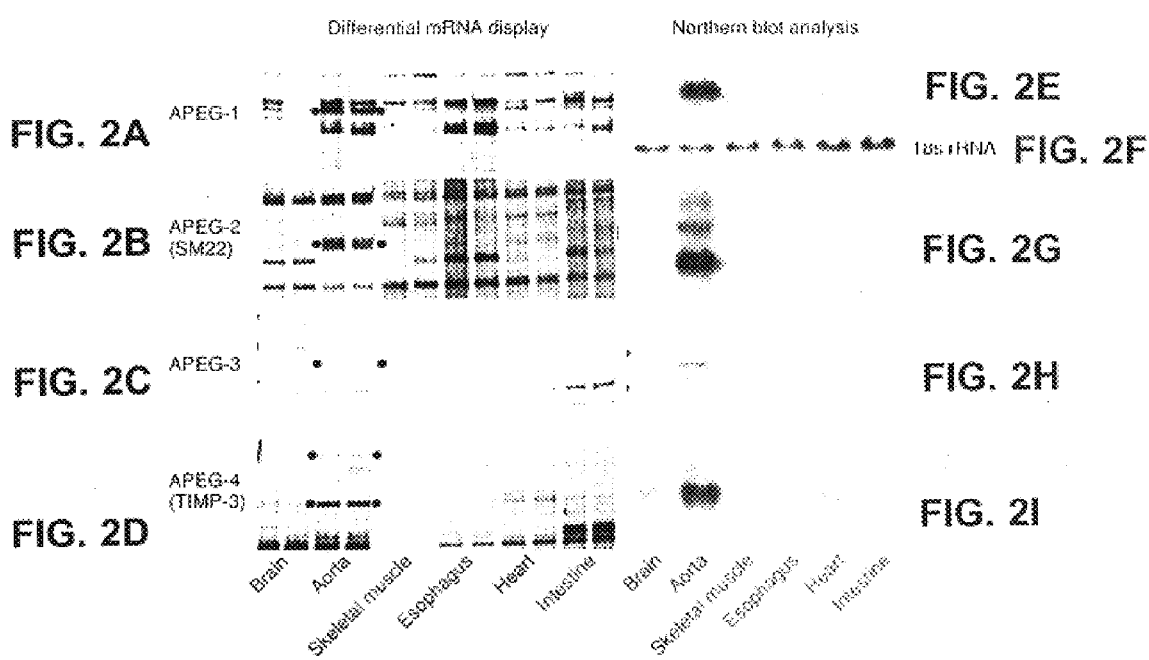

FIG. 3A  APEG-1 full cDNA

FIG. 3B  APEG-1 3' D.D. frag

FIG. 3C  18s rRNA

FIG. 3D
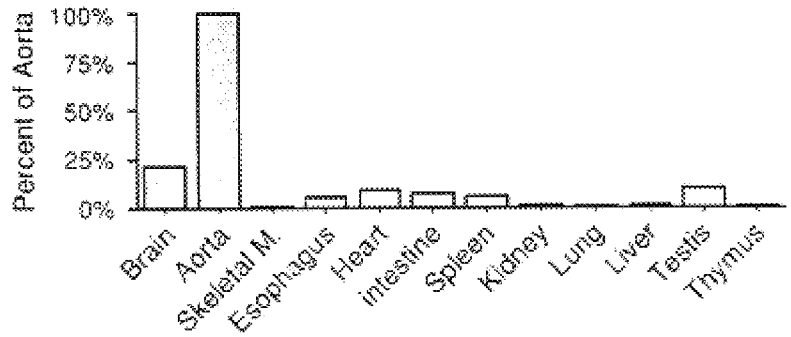

FIG. 4

Rat aortic cDNA library in the yeast expression vector pcJATA

↓

EcoR I and Xho I digestion
Release of the cDNA from the vector

↓

Separate the cDNAs on two identical agarose gels

Cut out the corresponding slice as shown on the Southern analysis

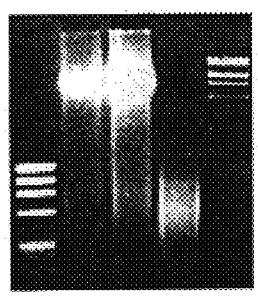

↓

Eluted cDNA fragments

↓

Ligation with pSP72 plasmid vector linearized by EcoR I and Xho I digestion

→ Transform E. coli cells to establish an aortic cDNA sublibrary

→ Screen the aortic cDNA sublibrary with rAPEG-1 3' D.D. frag

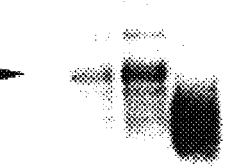

Southern blot analysis with rAPEG-1 3' D.D. frag 1      gaattcggcacgagcagagacttaaggaaggtgcagacgggtccgtttgcacagcctcagggcgcgtcc
71     acatcccctttcagcagcccaatcacctctgatgaggagtacctgagccccccagagaggagttcccagaac
141    ctggggagacctggtcccgaaCCcTACCAGTGAAGCCCAGTCCCAGGATCCGAGATTCCTCTGACTC
211    TTCCTCCAAGGCACCCCCAACCTTCAAGTCTCACTCATGAAGTCTCACTCAGTGAGAGAAGGTCAAGATGTC
281    A TATGAGCATCCGCGTGCAGGGGAGCCCAAGCCCTGGTCTCTCCTGGCTGAGGAATCGGCAGCCTGTGC
351    GCCCAGACCAGCGGCGCTTTGCAGGAGGCCGAGGGTGGGCTCTGCCGGTTGAGGATCCTGGCTGCTGA
421    GAGGGGAGATGCTGGTTTCTACACTTGCAAGGCGGTCAACGAATATGGCGCTCGGCAGTGTGAGGCCCGC
491    CTGGAGTCCGAGGGCGAGTGAgctcaggggccacctgcctgcgccccgctacctccgagctgcaccccc
561    tgtctcaggcacctcctgacctcgctgtgtttcactgcccacagaccccagccggctcgccgg
631    cccggacatagcccctatgctccctccctcctagccacacccctgggtaaccacatcggccccc
701    tgtggatccctccctcccccaagtggatatgtggctgtgcagaaggagccccagaaggactgagtgtt
771    gagaagggatggccatgaggttgtgacaagctcccccagctgtcctctgtcctgtgtctgtgacagcg
841    aatgcatgtgctatgctgctacaggccactgctctgctctgttctctgtgtctgtgacagt
911    cagggaagaaaaccttCGAGCTGaggtgggataagacagaataagactctctgggaagggtagggcactgc
981    tgcaggggcccagagggcaggcacagtggcacaacattttttattccacatgagacaaaagctagaggtctggattaa
1051   agaaatgggtttaaatggcaagcttaggaccaagtggggtacccttcttcacagacacacgctctgt
1121   gccctgactgctgcaagctgtgagactgagccagtgcacaggagccaggtcatagtgggactggacttttgaaacact
1191   ctgggaatgagaaagagcagactgagccagtgcacagtgggactcatagtgggactggacttttgaaacact
1261   atttcgtagctcaaataaagtccagtttgtacccaaaaaaaaaaaaa   SEQ ID NO:1

FIG. 5

```
  1   ATG AAG CCC AGT CCC AGC CAG GAT CGA GAT TCC TCT GAC TCT TCC AAG
      Met Lys Pro Ser Pro Ser Gln Asp Arg Asp Ser Ser Asp Ser Ser Lys

18   GCA CCC CCA ACC TTC AAG GTC TCA CTC ATG GAC CAA TCA GTG AGA GAA GGT
      Ala Pro Pro Thr Phe Lys Val Ser Leu Met Asp Gln Ser Val Arg Glu Gly

35   CAA GAT GTC ATT ATG AGC ATC CGC ATC CGG CAG GGG GAG GTG CCT GTG GTC
      Gln Asp Val Ile Met Ser Ile Arg Ile Arg Gln Gly Glu Val Pro Val Val

52   TCC TGG CTG AGG AAT CGG CAG CCT GTG CGC CCA GAC CAG CGG CGG TTT GCA
      Ser Trp Leu Arg Asn Arg Gln Pro Val Arg Pro Asp Gln Arg Arg Phe Ala

69   GAG GAG GCC GAG GGT GGG CTC TGC TTG CGG AGG TTG AGG ATC CTG GCT GCT GAG AGG
      Glu Glu Ala Glu Gly Gly Leu Cys Leu Arg Arg Leu Arg Ile Leu Ala Ala Glu Arg

86   GGA GAT GCT GGT TTC TAC ACT TGC AAG GCG GTC AAC GAA TAT GGC GCT CGG
      Gly Asp Ala Gly Phe Tyr Thr Cys Lys Ala Val Asn Glu Tyr Gly Ala Arg

103   CAG TGT GAG GCC CGC CTG GAG GTC CGA GGC GAG TGA                SEQ ID NO:2
      Gln Cys Glu Ala Arg Leu Glu Val Arg Gly Glu ***                SEQ ID NO:3
```

FIG. 6

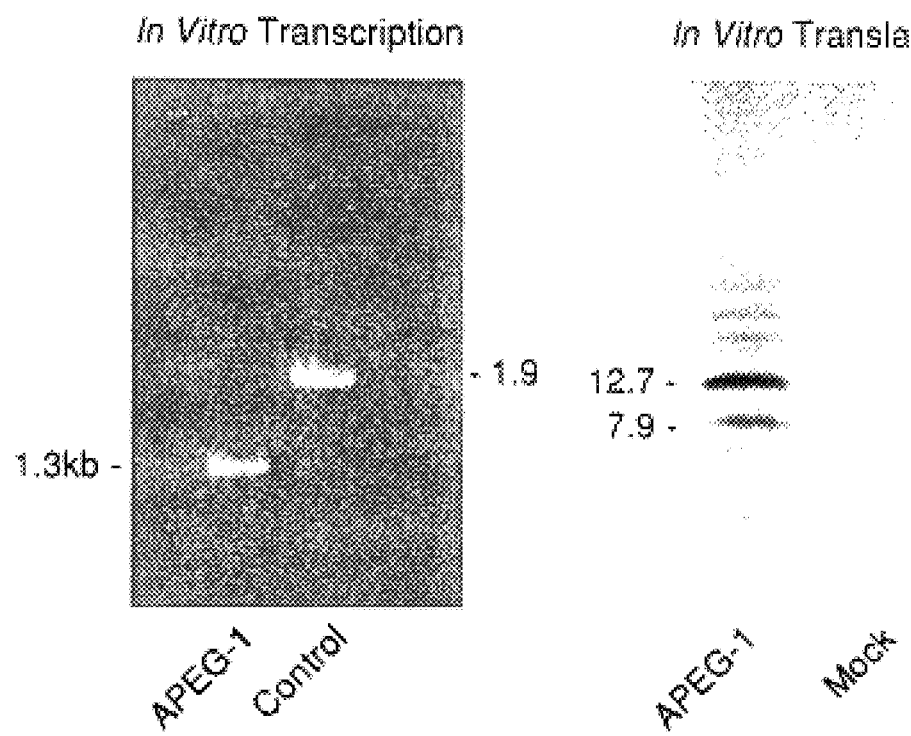
FIG. 7A  FIG. 7B

```
ChkTelo    MAMISGMSGR KASGSSPTSP INADKVENED .....AFLEEV AEEKPHVKPY FTKTILDMEV
ChkMLCK    MAMISGMSGR KASGSSPTSP INADKVENED .....AFLEEV AEEKPHVKPY FTKTILDMEV
RabTelo    MAMISGLSGR KSSTGSPTSP LTAERLETEE DVSQAFLEAV AEEKPHVKPY FSKTIRDLEV
RabMLCK    MAMISGLSGR KSSTGSPTSP LTAERLETEE DVSQAFLEAV AEEKPHVKPY FSKTIRDLEV
APEG-1     MKPSPSQDR  DSSDSSSKAP ..........  .......... ........PT FKVSLMDQSV
Consensus  ----S----R ---S----P  ---------- ---------- ---------P- F------D---V ChkTelo    VEGSAARFDC KIEGYPDPEV MWYKDDQPVK ESRHFQIDYD EEGNCSLTIS EVCGDDDAKY
ChkMLCK    VEGSAARFDC KIEGYPDPEV MWYKDDQPVK ESRHFQIDYD EEGNCSLTIS EVCGDDDAKY
RabTelo    VEGSAARFDC KIEGYPDPEV VWFKDDQSIR ESRHFQIDYD EDGNCSLIIS DVCGDDDAKY
RabMLCK    VEGSAARFDC KIEGYPDPEV VWFKDDQSIR ESRHFQIDYD EDGNCSLIIS DVCGDDDAKY
APEG-1     REGQDVIMSI RVQGEPKPVV SWLRNRQPVR PDQRRFAEEA EGGLCRLRIL AAERGDAGFY
Consensus  -EG------- ---G-P-P-V ------Q--- ------- -W E-G-C-L-I- -----D---Y ChkTelo    TCKAVNSLGE ATCTAELLVE TMGKEGEGEG EGEEDEEEEE E    SEQ ID NO:4
ChkMLCK    TCKAVNSLGE ATCTAELLVE TMGKEGEGEG EGEEDEEEEE E    SEQ ID NO:5
RabTelo    TCKAVNSLGE ATCTAELIVE TME.EGEGEG EEEEEE           SEQ ID NO:6
RabMLCK    TCKAVNSLGE ATCTAELIVE TME.EGEGEG EEEEEE           SEQ ID NO:7
APEG-1     TCKAVNEYGA RQCEARLEVR GE                         SEQ ID NO:8
Consensus  TCKAVN--G- --C-A-L-V- ---------- ------           SEQ ID NO:9
```

FIG. 8

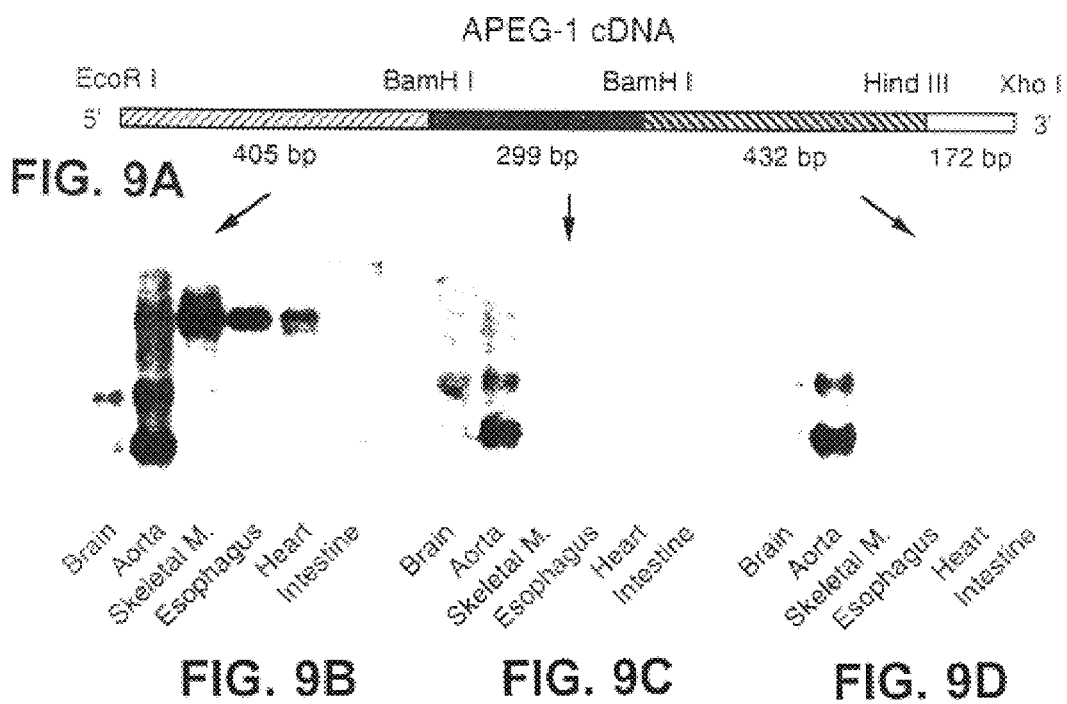
FIG. 9A
FIG. 9B
FIG. 9C
FIG. 9D
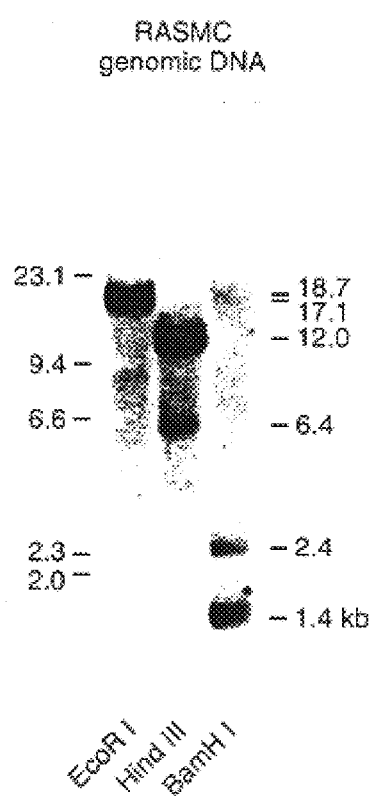
FIG. 10

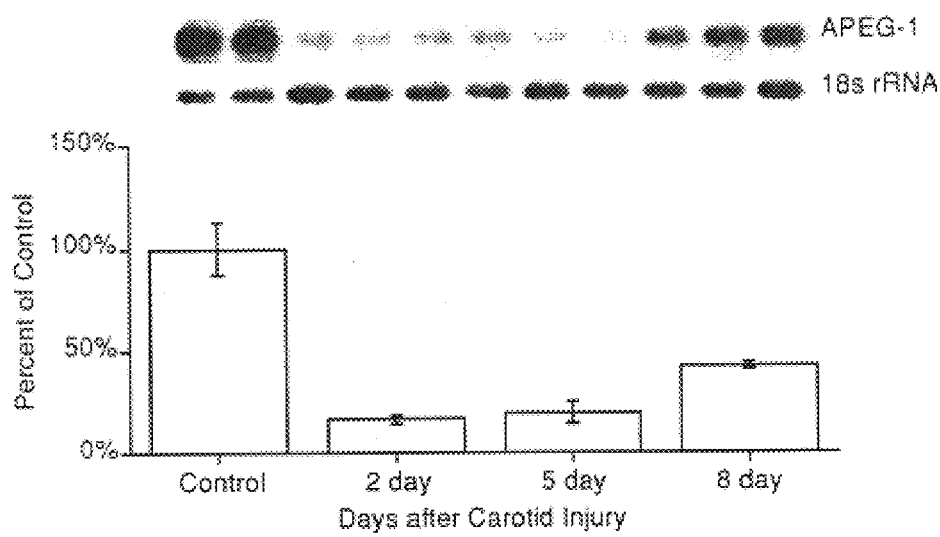
FIG. 13A
FIG. 13B
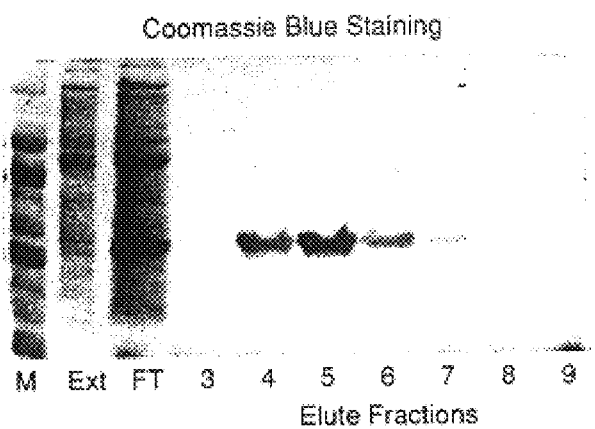
FIG. 14A
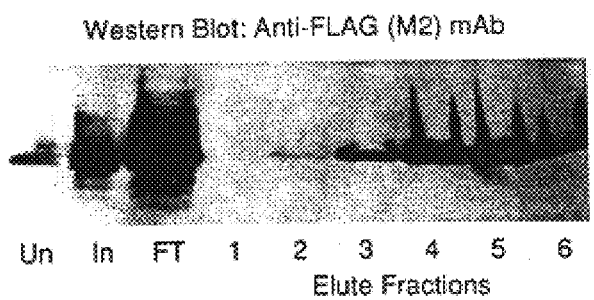
FIG. 14B

APEG-1 cDNA Sequence

```
   1  TCACCTCTGA TGAGGAATAC CTGAGCCCCC CAGAGGAGTT CCCAGAGCCT
  51  GGGGAGACCT GGCCGCGAAC CCCCACCATG AAGCCCAGTC CAGCCAGGA
 101  CCGCCGTTCT TCTGACACTG GCTCCAAGGC ACCCCCCACC TTCAAGGTCT
 151  CACTTATGGA CCAGTCAGTA AGAGAAGGCC AAGATGTCAT CATGAGCATC
 201  CGCGTGCAGG GGGAGCCCAA GCCTGTGGTC TCCTGGCTGA GAAACCGCCA
 251  GCCCGTGCGC CCAGACCAGC GGCGCTTTGC GGAGGAGGCT GAGGGTGGGC
 301  TGTGCCGGCT GCGGATCCTG GCTGCAGAGC GTGGCGATGC TGGTTTCTAC
 351  ACTTGCAAAG CGGTCAATGA GTATGGTGCT CGGCAGTGCG AGGCCCGCTT
 401  GGAGGTCCGA GGCGAGTGAG CTCAGGGGGC CACCTGCGCT CCCCCCGCTA
 451  CCCTCCGAGC CGCGCCCCTG TCTCAGGCAC CTCTCGGACC TCGCTGTGTT
 501  TCACTGCCTC CTGCCCACAG ACCCAGGCCT GCCGGCCCGG ACCCGTCCCA
 551  GCCTCCCCTC CCCACCCCAT GCAGCCCCCA GGGGGATAGC CCATGGGCCC
 601  CTGTGGACAC TCCCTCCCCA AGTGGACACA TGGCTGTGCA GGCCAGGAGG
 651  CCCACAGATG GACTGAGTGC TGGGAAGGGG CGGCTTCGAG GGGTATCAAC
 701  CCCCCGAGTC TCTCCCTGAA GGGGAGCACC GGGCGAGTGC ATGTGCTACT
 751  GCTGCTACAG GCCTGTCTAT CTGTTTGTCT GTCTGTGTGT CTGTGACAGT
 801  CAGGGAAGGA TGCCTCGGAG CTGAGGTGGG GTGAGACAGA GTGGGAGAGA
 851  TTACGGCATG GCATGGAGGG GCCCAAGGAG CAGGGGCTGT TGACAAAGGC
 901  CTTACCAGGA AGGGTTAGGA CACTGACCAT TCTAGAAATG GGTTTCGAAT
 951  GGCACAACAC TTTCTATTTC ACAAAAGACC AAAAGCCAGA GGCCCCAGGC
1001  TCTGTGCTGA TGAACAGCCT GGCTGAGCCC TGGCCCTGGC AGGTTTAGGG
1051  CCCATTTGGG GCCCCCTCCT TCTCTGTCAG GGCTGGGGTG CTCTGTCTGG
1101  GAATGAGGGA GTTAACCAAG TTTGGTGCAG GAGCAGGGGC AGGGGGCCAC
1151  TGTAGTGAGC GTGGATGAAA TTTGGANACA CCTATNTCTT AANTCAAATA
1201  AAGTCCAGTT TGTACCTAAA AAAAAAA      SEQ ID NO:11
```

FIG. 16

Predicted Human APEG-1 Peptide Sequence

```
  1  MKPSPSQDRR SSDTGSKAPP TFKVSLMDQS VREGQDVIMS IRVQGEPKPV
 51  VSWLRNRQPV RPDQRRFAEE AEGGLCRLRI LAAERGDAGF YTCKAVNEYG
101  ARQCEARLEV RGE*   SEQ ID NO:12
```

FIG. 17

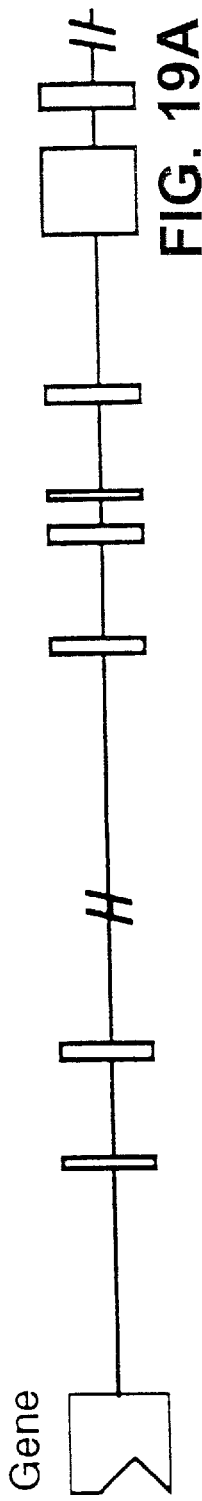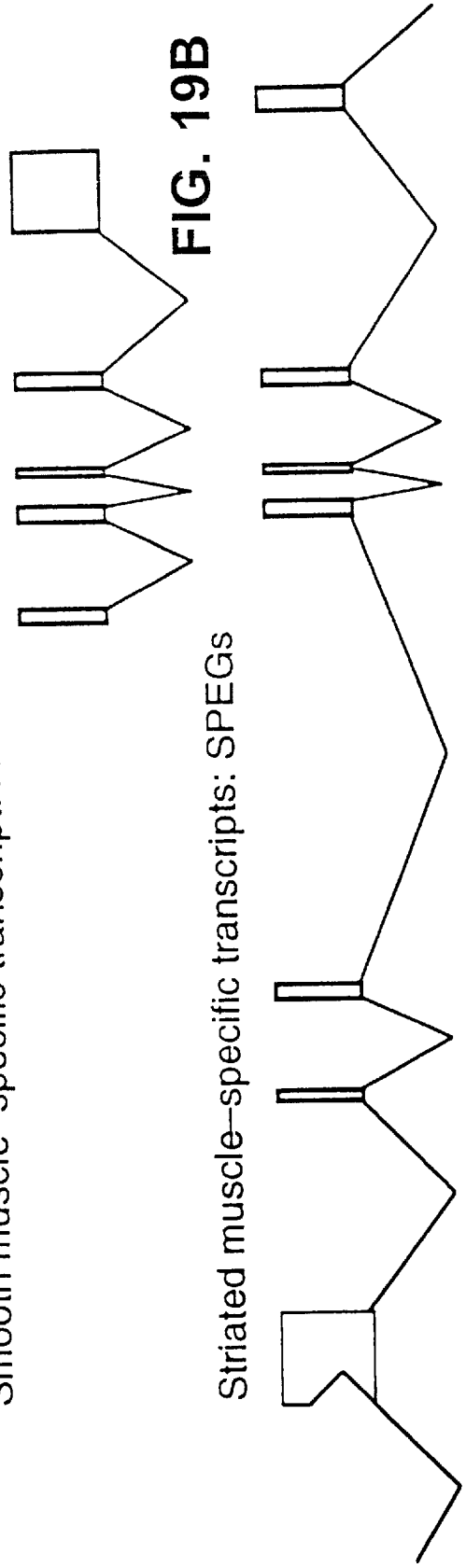
FIG. 19A
FIG. 19B
FIG. 19C
Gene
Smooth muscle-specific transcript: APEG-1
Striated muscle-specific transcripts: SPEGs
☐ Common exons
☐ Vascular smooth muscle-specific exons
☐ Striated muscle-specific exons

```
   1  GAATTCCGGT  CCAAATCCGC  GCTGCTCCCC  CCACCGTCCC  CTCGGGTCGG
  51  GAAGCGGTCC  CCGCCGGGAC  CCCCGGCCCA  GCCCGCGGCC  ACCCCCACGT
 101  CGCCCCACCG  TCGCACTCAG  GAGCCTGTGC  TGCCCGAGGA  CACCACCACC
 151  GAAGAGAAGC  GAGGGAAGAA  GTCCAAGTCG  TCCGGGCCCT  CCCTGGCGGG
 201  CACCGGGAAT  CCCGACCCCA  GACGCCACTG  AGCGAGGCCT  CAGGCCGCCT
 251  GTGGGCGTTG  GGCCGATCGC  CTAGGCTGGT  GCGCGCCGGC  TCCCGCATCC
 301  TGGACAAGCT  GCAGTTCTTC  GAGGAGCGAC  GGCGCAGCCT  GGAGCGCAGC
 351  GACTCGCCGC  CGGCGCCCCT  GCGGCCCTGG  GTGCCCCTGC  GCAAGGCCCG
 401  CTCTCTGGAG  CAGCCCAAGT  CGGAGCGCGG  CGCACCGTGG  GGCACCCCCG
 451  GGGCCTCGCA  GGAAGAACTG  CGGGCGCCAG  GCAGCGTGGC  CGAGCGGCGC
 501  CGCCTGTTCC  AGCAGAAAGC  GGCCTCGCTG  GACGAGCGCA  CGCGTCAGCG
 551  CAGCCCGGCC  TCAGACCTCG  AGCTGCGCTT  CGCCCAGGAG  CTGGGCCGCA
 601  TCCGCCGCTC  CACGTCGCGG  GAGGAGCTGG  TGCGCTCGCA  CGAGTCCCTG
 651  CGCGCCACGC  TGCAGCGTGC  CCCATCCCCT  CGAGAGCCCG  GCGAGCCCCC
 701  GCTCTTCTCT  CGGCCCTCCA  CCCCCAAGAC  ATCGCGGGCC  GTGAGCCCCG
 751  CCGCCGCCCA  GCCGCCCTCT  CCGAGCAGCG  CGGAGAAGCC  GGGGGACGAG
 801  CCTGGGAGGC  CCAGGAGCCG  CGGGCCGGCG  GGCAGGACAG  AGCCGGGGGA
 851  AGGCCCGCAG  CAGGAGGTTA  GGCGTCGGGA  CCAATTCCCG  CTGACCCGGA
 901  GCAGAGCCAT  CCAGGAGTGC  AGGAGCCCTG  TGCCGCCCCC  CGCCGCCGAT
 951  CCCCCAGAGG  CCAGGACGAA  AGCACCCCCC  GGTCGGAAGC  GGGAGCCCCC
1001  GGCGCAGGCC  GTGCGCTTCC  TGCCCTGGGC  CACGCCGGGC  CTGGAGGGCG
1051  CTGCTGTACC  CCAGACCTTG  GAGAAGAACA  GGGCGGGGCC  TGAGGCAGAG
1101  AAGAGGCTTC  GCAGAGGGCC  GGAGGAGGAC  GGTCCCTGGG  GGCCCTGGGA
1151  CCGCCGAGGG  GCCCGCAGCC  AGGGCAAAGG  TCGCCGGGCC  CGGCCCACCT
1201  CCCCTGAGCT  CGAGTCTTCG  GATGACTCCT  ACGTGTCCGC  TGGAGAAGAG
1251  CCCCTAGAGG  CCCCTGTGTT  TGAGATCCCC  CTGCAGAATG  TGGTGGTGGC
1301  ACCAGGGGCA  GATGTGCTGC  TCAAATGTAT  CATCACTGCC  AACCCCCCGC
1351  CCCAAGTGTC  CTGGCACAAG  GATGGGTCAG  CGCTGCGCAG  CGAGGGCCGC
1401  CTCCTCCTCC  GGGCTGAGGG  TGAGCGGCAC  ACCCTGCTGC  TCAGGGAGGC
1451  CAGGGCAGCA  GATGCCGGGA  GCTATATGGC  CACCGCCACC  AACGAGCTGG
1501  GCCAGGCCAC  CTGTGCCGCC  TCACTGACCG  TGAGACCCGG  TGGGTCTACA
1551  TCCCCTTTCA  GCAGCCCAT   CACCTCCGAC  GAGGAATACC  TGAGCCCCCC
1601  AGAGGAGTTC  CCAGAGCCTG  GGGAGACCTG  GCCGCGAACC  CCCACCATGA
1651  AGCCAGTCC   CAGCCAGAAC  CGCCGTTCTT  CTGACACTGG  CTCCAAGGCA
1701  CCCCCCACCT  TCAAGGTCTC  ACTTATGGAC  CAGTCAGTAA  GAGAAGGCCA
1751  AGATGTCATC  ATGAGCATCC  GCGTGCAGGG  GGAGCCCAAG  CCTGTGGTCT
1801  CCTGGCTGAG  AAACCGCCAG  CCCGTGCGCC  CAGACCAGCG  GCGCTTTGCG
1851  GAGGAGGCTG  AGGGTGGGCT  GTGCCGGCTG  CGGATCCTGG  CTGCAGAGCG
1901  TGGCGATGCT  GGTTTCTACA  CTTGCAAAGC  GGTCAATGAG  TATGGTGCTC
1951  GGCAGTGCGA  GGCCCGCTTG  GAGGTCCGAG  GCGAGTGAGC  TCAGGGGGCC
2001  ACCTGCGCTC  CCCCGCTAC   CCTCCGAGCC  GCGCCCTGT   CTCAGGCACC
2051  TCTCGGACCT  CGCTGTGTTT  CACTGCCTCC  TGCCCACAGA  CCCAGCTGCC
2101  GGCCCGGACC  CGTCCCAGCC  TCCCTCCCC   ACCCCATGCA  GCCCCAGGG
2151  GGATAGCCCA  TGGGCCCCTG  TGGACCCTCC  CTCCCCAAGT  GGACACATGG
```

FIG. 20A

```
2201  CTGTGCAGCC AGGAGGCCCA CAGATGGACT GAGTGCTGGG AAGGGGCGGC
2251  TGCGAGGGGT ATCAACCCCC CGAGTCTCTC CCTGAAGGGG AGCACCGGGC
2301  GAGTGCATGT GCTACTGCTG CTACAGGCCT GTCTATCTGT TTGTCTGTCT
2351  GTGTGTCTGT GACAGTCAGG GAAGGATGCC TCGGAGCTGA GGTGGGGTGA
2401  GACAGAGTGG GAGAGATTAC GGCATGGCAT GGAGGGGCCC AAGGAGCAGG
2451  GGCTGTTGAC AAAGGCCTTA CCAGGAAGGG TTAGGACACT GACCATTCTA
2501  GAAATGGGTT TCGAATGGCA CAACACTTTC TATTTCACAA AAGACCAAAA
2551  GCCAGAGGCC CCAGGCTCTG TGCTGATGAA CAGCCTGGCT GAGCCCTGGC
2601  CCTGGCAGGT TTAGGGCCCA TTTGGGGCCC CCTCCTTCTC TGTCAGGGCT
2651  GGGGTGCTCT GTCTGGGAAT GAGGGAGTTA ACCAAGTTTG GTGCAGGAGC
2701  AGGGGCAGGG GGCCACTGTA GTGAGCGTGG AGAAATTTGG AAACACCTAT
2751  TTCTTAACTC AAATAAAGTC CAGTTTGTAC CTAAAAAAAA AAA
      (SEQ ID NO:13)
```

FIG. 20B

```
  1 IPVQIRAAPP TVPSGREAVP AGTPGPARGH PHVAPPSHSG ACAARGHHHR REAREEVQVV
 61 RALPGGHRES RPQTPLSEAS GRLWALGRSP RLVRAGSRIL DKLQFFEERR RSLERSDSPP
121 APLRPWVPLR KARSLEQPKS ERGAPWGTPG ASQEELRAPG SVAERRLFQ  QKAASLDERT
181 RQRSPASDLE LRFAQELGRI RRSTSREELV RSHESLRATL QRAPSPREPG EPPLFSRPST
241 PKTSRAVSPA AAQPPSPSSA EKPGDEPGRP RSRGPAGRTE PGEGPQQEVR RRDQFPLTRS
301 RAIQECRSPV PPPAADPPEA RTKAPPGRKR EPPAQAVRFL PWATPGLEGA AVPQTLEKNR
361 AGPEAEKRLR RGPEEDGPWG PWDRRGARSQ GKGRRARPTS PELESSDDSY VSAGEEPLEA
421 PVFEIPLQNV VVAPGADVLL KCIITANPPP QVSWHKDGSA LRSEGRLLLR AEGERHTLLL
481 REARAADAGS YMATATNELG QATCAASLTV RPGGSTSPFS SPITSDEEYL SPPEEFPEPG
541 ETWPRTPTMK PSPSQNRRSS DTGSKAPPTF KVSLMDQSVR EGQDVIMSIR VQGEPKPVVS
601 WLRNRQPVRP DQRRFAEEAE GGLCRLRILA AERGDAGFYT CKAVNEYGAR QCEARLEVRG
661 E  (SEQ ID NO:14)
```

FIG. 21

```
   1  GAATTCCGGC TGGCGGGCAC AGTGGAGTCC CGGCCCCAGA CGCCACTGAG
  51  CGAGGCTTCG GGTCGCCTGT CAGCACTGGG CCGCTCGCCC CGGCTGGTGC
 101  GCGCGGGGTC CCGCATCCTG GACAAGCTAC AGTTCTTCGA AGAGCGGCGA
 151  CGCAGCCTGG AGCGCAGCGA CTCGCCGCCA GCGCCCCTGC GGCCCTGGGT
 201  GCCCCTGCGC AAGGCTCGCT CGCTGGAGCA GCCGAAGTCC GAGGGCGGTG
 251  CGGCGTGGGG CACACCCGAG GCCTCGCAGG AGGAGCTGCG GTCACCTCGG
 301  GGCAGTGTGG CAGAGCGGCG TCGCCTGTTC AGCAAAAGG CGGCCTCGTT
 351  GGATGAACGC ACGCGACAAC GCAGTGCAAC CTCGGACCTC GAACTCCGCT
 401  TCGCCCAGGA GCTGGGTCGC ATCCGCCGAT CTACGTCGCG GGAGGAGCTG
 451  GTGCGTTCGC ACGAGTCCCT GCGTGCCACG CTGCAGCGCG CCCCATCCCC
 501  TCGGGAGCCC GGCGAGCCCC CACTCTTCTC CCGGCCTTCC ACACCCAAGA
 551  CCTCACGGGC TGTGAGCCCG GCTGCCACCC AGCCGCCGCC TCCTAGTGGT
 601  GCGGGCAAAT CTGGGGACGA GCCTGGGAGG CCCCGAAGCA GAGGGCCGGT
 651  GGGCAGGACT GAACCGGGGG AAGGCCCGCA GCAGGAGATC AAGCGTCGGG
 701  ACCAATTCCC GCTAACCAGG AGCAGAGCCA TCCAGGAGTG CAGGAGCCCT
 751  GTGCCGCCCT ACACCGCGGA TCCCCCGGAG AGCAGGACAA AAGCCCCCTC
 801  CGGTCGCAAG CGGGAACCCC CTGCTCAAGC GGTGCGCTTT CTGCCCTGGG
 851  CCACTCCGGG AGTGGAGGAC TCTGTTCTGC CCCAAACCTT GGAGAAGAAT
 901  AGAGCGGGAC CCGAGGCTGA GAAGAGGCTT CGCAGAGGAC CTGAGGAGGA
 951  TGGCCCCTGG GGGCCCTGGG ACCGCAGAGG GACCCGCAGC CAAGGCAAAG
1001  GTCGCCGTGC TCGGCCTACT TCCCCCGAGC TCGAGTCCTC AGACGACTCC
1051  TATGTGTCCG CTGGGAAGA GCCCCTGGAG GCACCCGTGT TTGAGATCCC
1101  TCTGCAGAAT ATGGTGGTGG CGCCAGGAGC TGACGTGCTA CTTAAGTGTA
1151  TCATCACCGC CAACCCCCCA CCCCAAGTGT CCTGGAAAAA GGATGGGTCC
1201  ATGTTGCACA GCGAGGGTCG TCTTCTCATC CGGGCTGAAG GTGAACGGCA
1251  CACACTGCTG CTCAGAGAGG CCCAGGCTGC TGATGCTGGG AGCTACACAG
1301  CCACTGCCAC CAACGAACTG GGCCAAGCTA CCTGTGCTTC TTCACTGGCT
1351  GTGAGACCTG GCGGCTCCAC ATCCCCTTTC AGCAGCCCCA TCACCTCTGA
1401  TGAGGAGTAC CTGAGCCCCC CAGAGGAGTT CCCAGAGCCT GGGGAGACCT
1451  GGCCCCGAAC CCCTACCATG AAGCTCAGTC CCAGCCAGGA TCATGATTCC
1501  TCCGACTCTT CTTCCAAGGC ACCCCCAACG TTCAAGGTCT CACTCATGGA
1551  CCAATCGGTG AGAGAAGGTC AAGATGTCAT TATGAGCATC CGTGTGCAGG
1601  GAGAGCCCAA GCCTGTGGTT TCCTGGCTGA GGAATCGACA GCCCGTGCGC
1651  CCAGACCAGC GGCGCTTTGC AGAGGAGGCC GAGGGTGGGC TCTGCCGCTT
1701  GAGGATCCTG GCTGCTGAAC GGGGCGATGC TGGTTTCTAC ACATGCAAGG
1751  CGGTCAACGA ATATGGCGCT CGGCAGTGCG AGGCCCGCCT GGAGGTCCGA
1801  GGCGAGTGAG CTCAGGGGGC CACCTGCGCT GCCCCGCTA CCCTCCGAGC
1851  TGCACCCCTG TCTCAGGCAC CTCTCGGACC TCGCTGTGTT TCACTGCCTC
1901  CTGCCCACAG ACCCAGCCGG CTCGCCGGCC GGACTTAGCC CATGCTCCC
1951  CTTCCCTCCC TAGCCCATAC AGCACCCTGG GGTAACCCAC CGGGCCCTG
2001  TGGATCCTCC CTCCCCAAGT GGATATGTGG CTGTGCAGAC CAGGAGGCCC
2051  CCAGAAGGAC TGAGTGTTGG GAAGGGATGG CCATGAGGGG TGCCAAGCTC
2101  CCTCGGTCTC CCCATAGGGA GCATCCAGCG AGTGCATGTG CTATGCTGCT
2151  ACAGGCCACT GTCTGTCTAT CTGTTTGTCC GTCTGTGTGT CTGTGACAGT
2201  CAGGGAAGAA AGCCTTTGAG CTGAGGTGGG CTAAGACAGA ATAAGATGAC
2251  AGAGCACAGC ATCCATGAGA TGCAGGGGTT CAGAGGGGTC AGGTACAGTG
```

FIG. 22A

```
2301  GATATGAGGC TCTCTGGGAA GGGGCAGGGC ACTGACCATT TCAGAAATGG
2351  GTTTTAAATG GCACAACATT TTTTATTCCA CAAGAGACCA AAAGCTAGAG
2401  GTCTAGGGTT AAGCCCTAGC TGCTGGCAAG ATTAGGACCA AGTGGGGTAC
2451  CCTTCTTTAC AGACACATCC GACACGCGCT GTCTGAGAAT GAGAGAGGTA
2501  GCCAGGCTGA ACACAGGAGC AGGGTCATAG TGGAGGTGGA GATTTGGAAA
2551  CACTATTTCG TAGCTCAAAT AAAGTCCAGT TTGTACCCAA AAAAAAAAA
2601  AAAAAAAAAA AAAA (SEQ ID NO:15)
```

FIG.22B

```
  1 EFRLAGTVES RPQTPLSEAS GRLSALGRSP RLVRAGSRIL DKLQFFEERR RSLERSDSPP
 61 APLRPWVPLR KARSLEQPKS EGGAAWGTPE ASQEELRSPR GSVAERRRLF QQKAASLDER
121 TRQRSATSDL ELRFAQELGR IRRSTSREEL VRSHESLRAT LQRAPSPREP GEPPLFSRPS
181 TPKTSRAVSP AATQPPPPSG AGKSGDEPGR PRSRGPVGRT EPGEGPQQEI KRRDQFPLTR
241 SRAIQECRSP VPPYTADPPE SRTKAPSGRK REPPAQAVRF LPWATPGVED SVLPQTLEKN
301 RAGPEAEKRL RRGPEEDGPW GPWDRRGTRS QGKGRRARPT SPELESSDDS YVSAGEEPLE
361 APVFEIPLQN MVVAPGADVL LKCIITANPP PQVSWKKDGS MLHSEGRLLI RAEGERHTLL
421 LREAQAADAG SYTATATNEL GQATCASSLA VRPGGSTSPF SSPITSDEEY LSPPEEFPEP
481 GETWPRTPTM KLSPSQDHDS SDSSSKAPPT FKVSLMDQSV REGQDVIMSI RVQGEPKPVV
541 SWLRNRQPVR PDQRRFAEEA EGGLCRLRIL AAERGDAGFY TCKAVNEYGA RQCEARLEVR
601 GE  (SEQ ID NO:16)
```

FIG. 23

```
   1 GCGATAGATAACCTGGTGATCCAAACCTGTAATCCTAACTACTGTGGAGGCTGAGATAAT
  61 AACTTGCCAGAGATACAGAGTCAGTTCAAGACCACCCTAGGCAACTAAAGAGATCTTGTT
 121 TCAGACTAAGAAAAAGAGGCCTAGCAAGGCCCTACATTCAATCCCCCAGAAACAAATGAC
 181 TCAGACAGCCCAAGTCCAGACTGTAAATCAGAGACTACAGGGGACCATACCCCAAAGAAC
 241 TCTCTAGAATTCCTGTGCTCAGAAAACTTTGAAACCCAATCAACCAAACTGGGCAGTGGT
 301 GTCACATGCTTTTAATCCCAGTACTCAGGAGGCAGAGGCAGGCAGATCTCTGAGTTCAAG
 361 TCCAGCCTGATTTACTGATTGAGTCAAGGCTACACAGAGATACCCTGTCTCAAAAAACTA
 421 ACAAGCAAAATACAAAAACAAAAACCAAAAAAAAAAAAAAAAAAAAAAAAAAAATAAGAA
 481 GCCCAACCATATAAGAAGCATTTTGAAAAAAACTAATGTTTGAAATCGCTGGCATGGGG
 541 TTAAAGATCTAGTTCAAATTGGGAAGCTGGCTGCTGTCATTGGAATCACAAGGGCTGTCG
 601 AACCAGACTTAGGGATTTACAGCCCTGCTCTGAAGTTGAATGGCCAAGAGCTGTGAGATT
 661 CAGTGAAATCACCTCTTAGAGTTCCCATCCTCCCATGAGGATTTGCCTAGGTCTCAAAAC
 721 TTCCATGTGCCTAGGGATCTCTAGAGTGCTTTTGAAAAAAAATTACAGTGTTCGACTCCT
 781 CACTTTAGAAAATCAATTCTGTAGGCTGGATAAGGTCTAAGAATCTGTATTTCAAAACAA
 841 GCCCCAAGTGGTACCCGTGTGGGTGGTTCAAGCATCACGCACACAGTCCTGGTGTAGATG
 901 GCCTTGGGTGATGCTATCCGTGTGCTAGAAACTGGGTGTCTGTCGTGAAGAGACTACAGA
 961 CAGCTGGGATGTCAGGCTTGACTGGATATACTGGCCTGGGGGAAATTCCTGCTTGTGGGC
                                         NFkB/GArC
1021 TGTCTAATGCCAGTTCTTATTGAATGATACTGGCCTGAAAGAACTGTCCAAAGGGCAGCT
1081 AGATGAATAGAGTCAGCTCATGGAGAGCTGGGTCAAATGTAATGAAGTGGTCCTTTAATG
                                                       CArG
1141 GGAAGGTTTGGGATCAAAAGAACACTGCCCTTGCTGGTGTTATCTCCCACAGTGAAATCT
1201 GGGTTTGTAGATGGATCAGGCTTGGATGTTACAAAAAAATGGCTACAAAGTTGCTTTAG
1261 CCCATGCGGTCTGCAGGGCTTGGATTCTACAGCTTGGTGGTGTACTTTGGGGTTATGGC
1321 TGGAACAGAGGCCACTTCTTTTTCTCAGAGAGGCATTCCATTGGAGCTTGAGCCTGCAGC
1381 CTGACAAGCAATCTCGCCAAGACTCTTGACCTAGGCTTGCTGCTGATTGGCTGGCTAGCA
1441 CCTAGGTTCTATTTCCCTGCTGGCCACCAGGGGTCTCTGAAGCAAACATAGACCTTTGGC
1501 AATTCGAGTTAAATGTTTGCCCCGCCCTCCTTTCCTTAGCCTGGGAGCTTGCCTCAGCAC
                   Sp1
1561 TGTCCAGCCTGGAGGTGACCCTGGAGCCAGGAATCTAAACTCTGTAGAGGGAAAGGAGTC
1621 CCCTCTTCCAAGGGCTGTGCCTATGACCTCAGTATCAGCTGGTGGCCACGCCCCGGCCA
                                              Sp1
1681 CAAATGCCATTCGGATTTCTCTCTCCTCCCCAACCTTGAGACTGCCAGCCTGAAAGTGGG
1741 CTGTCCTCTTGGCCCCCACACTTCTTCATCACTGGCAGTGCTGGGAACACAGGTCATAG
1801 CTTGGGAATGTGGCCCTGGGTGGAGAGAGGGGATCAAGGAGGGAGAGAGATTTGTGGCCT
1861 CTGCTCAACACCTCTGCTTCTATTATTCTTCCTGAGCCCCTTCCCTACCCACTGGGTGCA
1921 AACGGAAGCTGGGGAGGAGCGACCATTGGGGAGGAGCGGCCCACACTTCCCTAGCTTTGA
1981 GCCCTGGTGGGCTGAGGGGTGAGGGGCAGTTTGCCAGCAGAAATTCAGTAGAACCCATGG
2041 TTGAGCAGGGTGCAGGCCTGTGTCCTGAAGTACCTGCTCTCCTGAACTTGTCTAGGGCAG
2101 GACCTGGGAGTCTGCAGCCATGGGCTCAGTTTCCTTAGGTTGGCAGGGGACAAATCTGGA
2161 AAGGAGGGTCAAGCCCTGACAGTTCTTTGGTTCTCTGTGTCTGAAAAAGCTGGTTGTGGC
2221 CTATTTGGGGGTTTAAGGCTGGCTAGTTATGTATTCCTAGGTCAGGATTCTTCTTGGTTT
     CArG
2281 GGGCAAAGCATGGCGCTTGCTGTGCTGTATGGGTCAACACTTCTGGCCCAGGCAAGGATA
2341 TTAAATGCCGCAGTGCAGTGCCACCCCTTAGACCCCTCTGAGGACCGGGGTCCCCACACC
                                                       E box
2401 TGTAGTCTAGGCCCTACTGATGGGTTCAGCTCTTGTCAGTGTCCCAAGCTGTAAGGAGAG
2461 GAAAGGCAGACAGCTAGCTGCTTGGAATGATCAGAGTCTAAATTCAGCTGGTCTGGGCTC
                                                            Sp1
2521 CGCCCCTCCCCCGTTCCTATTCCACCACTCCAGGGGCTGCTCCCTGTGGTCTCAGCAGGC
2581 ACCACCTTCCCAGCCAGCGCCTGCCTGCTGCCCAGCCTCTTGCTGGCCACCCCCACCTCC
2641 TCCTTCCCCCGCTCCTAGGCTCACTTCCCCTCCCCCCAGGGCTGGCTCAGTGCGGGGCCT
2701 CAGCTGGGTCAGCGAGTGAGTGGGGCTGGCCAGGCTGA (SEQ ID NO:17)
```

FIG. 25

```
              1
Human.pep     MKPSPSQDRR SSDTGSKAPP TFKVSLMDQS VREGQDVIMS IRVQGEPKPV
Mouse.pep     MKLSPSQDHD SSDSSSKAPP TFKVSLMDQS VREGQDVIMS IRVQGEPKPV
Rat.pep       MKPSPSQDRD SSDSSSKAPP TFKVSLMDQS VREGQDVIMS IRVQGEPKPV
Consensus     MKxSPSQDxx SSDxxSKAPP TFKVSLMDQS VREGQDVIMS IRVQGEPKPV
                                                                    50

51
Human.pep     VSWLRNRQPV RPDQRRFAEE AEGGLCRLRI LAAERGDAGF YTCKAVNEYG
Mouse.pep     VSWLRNRQPV RPDQRRFAEE AEGGLCRLRI LAAERGDAGF YTCKAVNEYG
Rat.pep       VSWLRNRQPV RPDQRRFAEE AEGGLCRLRI LAAERGDAGF YTCKAVNEYG
Consensus     VSWLRNRQPV RPDQRRFAEE AEGGLCRLRI LAAERGDAGF YTCKAVNEYG
                                                                    100

101        114
Human.pep     ARQCEARLEV RGE*       (SEQ ID NO:12)
Mouse.pep     ARQCEARLEV RGE*       (SEQ ID NO:18)
Rat.pep       ARQCEARLEV RGE*       (SEQ ID NO:13)
Consensus     ARQCEARLEV RGEx       (SEQ ID NO:19)
```

TCCCCTCCCCCCAGGGCTGGCTCAGTGCGGGGCCTCAGCTGGGTCAGCCGAGTGAGTGGGGCTGGCCAGGCTGA

AP-2    E box    AP-2

+4    +76

(SEQ ID NO:20)

```
-2257  gtctcaaaaaactaacaagcaaaatacaaaaaaaaaaaacaaaaaaaaaaataagagcccaaccatataaga
-2167  agcatttgaaaaaaaaactaatgtttaggatcgctggcatggcttaaagatctagttcaaatctggaagtgctgctgttcattgaa
-2077  tcacaaggctgtcgaatcctcccactttagcagcagcgatttgcctagtctcaaaactccatgtcctcaagtctctagaatggcgaagcaccuc
-1987  ttagagtttcccatcctcctcactttagcagcagcgatttgcctagtctcaaaactccatgtcctcaagtctctagaatggcgaagcaccuc
-1897  cagtgttcgactccttggttcaagcatcagcgcacacagtcctggtgctggataaatctgtatttcaaaacaagcccaagtggtacc
-1807  cgtgtgtgggtttcaagcatcagcgcacacagtcctggtgctggataatctgtatttccgtgtgctgatgtatccgtgtgctaagaactgggtgtcgtcg
-1717  tgaagagactacagacagctgggatgtcaggtcaggcttgactgactggatatactggCtggggaaaattcctgcttgtgtgggctgtctaatgccagtt
                                                              AP-2  NFκB -1627  cttattgaatgatactggcctgaaagaactgtccaaagggcagctgatgaatagagtcagctcagctcatggagagtcggtcaaatgtaatga
-1537  agtggtccttaatgaaggtttgggatcaaaagaacactgccctgtcgttatctcccacagtgaaatctgggtttgtagatgga
                  CArG box -1447  tcaggcttgggatgttacaaaaaaaatggctacaaagttgctttagcccatgcggtctgcaggcttaggattctacagcttggtggtgta
                                                                           NFκB -1357  ctttggggttatggctgtggaacagaggccactgtctttcttcctcagagaggcattccattggagcctgagcctgcagcctgacaagcaatctc
-1267  gccaagactcttgaccttggcaattcgagttaaatgttttgcccgcctcttccttagcctgggagcttgcctcagccttgtccagcctgaagcaa
-1177  acatagaccttggcaattcgagttaaatgttttgcccgcctcttccttagcctgggagcttgcctcagccttgtccagcctgaagg
                                        Sp1

-1087  tgaccctggagccaggaatctaaactctgtagagggaaaagagtcccctcttccaaggctgtgtgcctatgacctcagtatcagctgtca
                              Δ-1073

-997   ccacgcccggcacaaatgccattcgagatttctctctcctcctcccaaccttgagactgccagcctgaaagtgggctgtcctccttggccc
       AP-2/Sp1

-907   ccacacttcttcatcactggcagtgctggggaacacaggtgctcatagcttggaatgtgccctgggtggagagagggatcaaggaggag
-817   agagattgtgtgcctctgctcaacaccttgctctatttcttccgagccctccctaccgggtgcaaacggtgcggaacgaaggcggga
-727   ggagcgaccattggggagcggccacactttccctagcttgagccctgtggcctgaagggtgagggcagtttgccagcagaaatt
                                                              Sp1
```

FIG. 31B

```
-637  cagtagaacccatggttgagcagggtgcaggcctgtgtcctgaagtacctgctctcctgaacttgtctgctcctggagtctgc
-547  agccatgggctcagttcccttaggttgtggcaggggacaaatctggaaaggaggtcaagccctgacagttcttggttctctgtctgaa
                                                                    Δ-479
-457  aaagctgttgtggcctatttgggttaaggctggctagttatgtattcctaggtcaggatccttcttggtttggcaaagcatggcg
                     CArG-like box
-367  cttgctgtgctgtatgggtcaacacttctggcccaggcaaggatattaaatgccgcagtgcagtgccaccccctagaccccctgaggac
                                      Δ-355
-277  cggggtccccacacctgtagtctaggcccctactgatgggttcagtcttgtcagtgtcccaagctgtaaggagagaggcagacagct
-187  agctgcttggaatgatcagagtctaaattcagctggtctgggctcccctattccaccactccaggggctgctccct
                                                                              Δ-122
-97   gtggtctcagcaggcaccaccttcccagccagcgcctgctgcctgccccacccccacctcctccttcccccgctcc
                                                             AP-2
-7    taggctcACTTCCCCTCCCCCCAGGGCCTGGCTCAGTGCGGGGGCCTCAGCTGGTCAGCGAGTGAGTGGGGCTGGCCAGGCTGA
              AP-2                                        E box                      Δ+76
                                                         Δ+38
```

(SEQ ID NO: 24)

FIG. 31C

AORTIC-SPECIFIC ENHANCER SEQUENCE AND USES THEREOF

This application is a continuation-in-part of U.S. Ser. No. 09/134,250, filed on Aug. 14, 1998.

BACKGROUND OF THE INVENTION

The invention relates to diagnosis and treatment of vascular injury.

Atherosclerosis and its subsequent complications, such as myocardial infarction, stroke, and peripheral vascular diseases, are the major causes of death in developed countries. Vascular endothelial and smooth muscle cells have important roles in the regulation of normal vascular tone. Damage or dysfunction of these cells can lead to vascular diseases, such as atherosclerosis and restenosis.

Atherosclerosis is believed to be a consequence of a response of the vascular wall to injury (Ross, R., 1993, Nature 362:801–9). Upon vascular injury and various other stimuli, cytokines and growth factors from activated vascular cells promote growth and migration of vascular smooth muscle cells in a dedifferentiated status, resulting in the formation of atherosclerotic plaques.

The pathogenesis of atherosclerosis is not fully understood, and an effective therapeutic regime has not been developed to prevent or cure atherosclerosis (Ross, R., The Pathogenesis of Atherosclerosis, in Heart Disease, a textbook of cardiovascular medicine, E. Braunwald, Editor, 1992, W. B. Saunders Company: Philadelphia. pp. 1106–24; and Ross, R.: The Pathogenesis of Atherosclerosis: a Perspective for the 1990s, 1993, Nature 362:801–9). Despite extensive research, the molecular mechanisms responsible for the regulation of gene expression in vascular endothelial and smooth muscle cells are largely unknown. In particular, trans-acting factors and cis-acting elements mediating vascular cell-specific gene expression have not been identified, mainly due to the fact that only a few vascular specific genes have been identified. Furthermore, of the genes that have been characterized as endothelial cell-specific (e.g. von Willebrand factors, VEGF receptor flk-1, VCAM-1, and E-selection (Hunter, J. J., et al., 1993, Hypertension 22:608–17) or smooth muscle cell-specific (e.g., CHIP28, SM22, and gax (Gorski, D. H., et al., 1993, Mol. Cell. Biol. 13(6):3722–33), many have been found in other cell types at various levels.

SUMMARY OF THE INVENTION

The invention is based on the discovery of a novel gene the expression of which gives rise to variant isoforms, one which is specific to aortic cells, and others which are found in striated muscle cells. Accordingly, the invention features an aortic cell-specific gene, and therefore provides a substantially pure DNA (e.g., genomic DNA, cDNA or synthetic DNA) encoding an aortic-preferentially-expressed gene-1 (APEG-1) polypeptide. By "substantially pure DNA" is meant DNA that is free of the genes which, in the naturally-occurring genome of the organism from which the DNA of the invention is derived, flank the APEG-1 gene. The term therefore includes, for example, a recombinant DNA which is incorporated into a vector, into an autonomously replicating plasmid or virus, or into the genomic DNA of a prokaryote or eukaryote at a site other than its natural site; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

Hybridization is carried out using standard techniques such as those described in Ausubel et al., Current Protocols in Molecular Biology, John Wiley & Sons, (1989). "High stringency" refers to DNA hybridization and wash conditions characterized by high temperature and low salt concentration, e.g., wash conditions of 65° C. at a salt concentration of approximately 0.1×SSC. "Low" to "moderate" stringency refers to DNA hybridization and wash conditions characterized by low temperature and high salt concentration, e.g. wash conditions of less than 60° C. at a salt concentration of at least 1.0×SSC. For example, high stringency conditions may include hybridization at about 42° C. and about 50% formamide; a first wash at about 65° C., about 2×SSC, and 1% SDS; followed by a second wash at about 65° C. and about 0.1% ×SSC. Lower stringency conditions suitable for detecting DNA sequences having about 50% sequence identity to an APEG-1 gene are detected by, for example, hybridization at about 42° C. in the absence of formamide; a first wash at about 42° C., about 6×SSC, and about 1% SDS; and a second wash at about 50° C., about 6×SSC, and about 1% SDS.

A substantially pure DNA having at least 50% sequence identity (preferably at least 70%, more preferably at least 80%, and most preferably at least 90%) to SEQ ID NO:1, 2, or 11, and encoding a polypeptide having a biological activity of an APEG-1 polypeptide is also within the invention. The percent sequence identity of one DNA to another is determined by standard means, e.g., by the Sequence Analysis Software Package developed by the Genetics Computer Group (University of Wisconsin Biotechnology Center, Madison, Wis.) (or an equivalent program), employing the default parameters thereof. "Biological activity of an APEG-1 polypeptide" is defined as the ability to inhibit the proliferation or migration of smooth muscle cells at the site of vascular injury.

The invention also includes a substantially pure DNA containing a constitutive or inducible, vascular cell-specific promoter, e.g., an APEG-1 promoter which is preferably in a vector into which an heterologous gene may be or has been cloned, and under the control of which the gene may be expressed. The promoter is preferably specific for arterial cells (e.g., cells of the aorta), and most preferably specific for vascular smooth muscle cells. DNA encoding APEG-1 may be operably linked to such regulatory sequences for expression of the APEG-1 polypeptide in vascular cells.

By "promoter" is meant a minimal DNA sequence sufficient to direct transcription. Promoters may be constitutive or inducible, and may be coupled to other regulatory sequences or "elements" which render promoter-dependent gene expression cell-type specific, tissue-specific or inducible by external signals or agents; such elements may be located in the 5' or 3' region of the native gene, or within an intron. By "heterologous promoter" is meant a promoter other than a naturally occurring APEG-1 promoter.

By "operably linked" is meant that a coding sequence and a regulatory sequence(s) are connected in such a way as to permit gene expression when the appropriate molecules (e.g., transcriptional activator proteins) are bound to the regulatory sequence(s).

The invention also provides a method of directing vascular cell-specific expression of a protein by introducing into a vascular cell an isolated DNA containing a sequence encoding the protein operably linked to the vascular cell-specific promoter. A cell containing the DNA or vector of the invention is also within the invention.

The invention also features a substantially pure APEG-1 polypeptide (e.g., rat APEG-1 (SEQ ID NO:3) or human APEG-1 (e.g., human APEG-1 (SEQ ID NO:12)) and an antibody which specifically binds to an APEG-1 polypeptide. By a "substantially pure polypeptide" is meant a polypeptide which is separated from those components (proteins and other naturally-occurring organic molecules) which naturally accompany it. Typically, the polypeptide is substantially pure when it constitutes at least 60%, by weight, of the protein in the preparation. Preferably, the protein in the preparation is at least 75%, more preferably at least 90%, and most preferably at least 99%, by weight, APEG-1 polypeptide. A substantially pure APEG-1 polypeptide may be obtained, for example, by extraction from a natural source (e.g., an aortic cell); by expression of a recombinant nucleic acid encoding an APEG-1 polypeptide; or by chemically synthesizing the protein. Purity can be measured by any appropriate method, e.g., column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include recombinant polypeptides derived from a eukaryote but produced in *E. coli* or another prokaryote, or in a eukaryote other than that from which the polypeptide was originally derived.

In another aspect, the invention provides a method of detecting injury in a sample of vascular tissue by determining the level of APEG-1 gene expression in the tissue; a decrease in the level of expression detected in the tissue sample compared to that detected in uninjured control vascular tissue indicates the presence of a vascular injury.

The invention also includes a method of inhibiting smooth muscle cell proliferation in an animal by contacting an artery of the animal with an APEG-1 polypeptide or a biologically active fragment thereof or with a compound that stimulates the APEG-1 promoter, e.g., stimulates APEG-1 expression.

In yet another aspect, the invention includes a method of making an APEG-1 polypeptide, e.g., a rat or human APEG-1 polypeptide, involving providing a cell containing DNA encoding an APEG-1 polypeptide and culturing the cell under conditions permitting expression of the APEG-1 encoding DNA, i.e., production of the recombinant APEG-1 by the cell.

The invention further features a substantially pure DNA having an APEG-1 derived enhancer sequence which regulates vascular smooth muscle cell-specific transcription of a polypeptide-encoding sequence to which it is operably linked. By "enhancer sequence" is meant a DNA sequence which contains one or more cis-acting elements which regulate transcription, e.g., cell specific transcription. The elements may be contiguous or separated by DNA not involved in the regulation of transcription, e.g., an enhancer element may be in a position immediately adjacent to the promoter element or up to several kilobases upstream or downstream of the transcriptional start site. The enhancer DNA is preferably derived from the 5' region of a mammalian APEG-1 gene, such as that of the mouse (SEQ ID NO:17), and regulates preferential expression in vascular smooth muscle cells, e.g., aortic smooth muscle cells, of a polypeptide-encoding DNA to which it is operably linked. Preferably, the enhancer includes a sequence which hybridizes under high stringency conditions to SEQ ID NO:20 or SEQ ID NO:23, or a complement thereof. More preferably, the enhancer includes the 73 nucleotides of SEQ ID NO:20, which is located within the sequence of SEQ ID NO:17. Most preferably, the enhancer includes the 38 nucleotides of SEQ ID NO:23, which is located within the sequence of SEQ ID NO:20.

The enhancer sequence can be less than 100 nucleotides in length or less than 50 nucleotides in length.

In some embodiments, the enhancer includes less than the complete nucleotide sequence of SEQ ID NO:17, e.g., it can contain less than 2.6 kb, 2.1 kb, 1.7 kb, 1.2 kb, 700 nucleotides, 500 nucleotides, or even 100 nucleotides of SEQ ID NO:17.

In some embodiments, the enhancer contains SEQ ID NO:20 and is less than 2.7 kb in length, 1.0 kb, 500 bp, 250 bp or 100 bp in length. The enhancer may also include a plurality of copies of SEQ ID NO:23 or SEQ ID NO:20.

The enhancer including SEQ ID NO:20 or SEQ ID NO:23 may be immediately contiguous to a polypeptide-encoding DNA. Alternatively, the enhancer may be separated by 5, 10, 20, 30, 40, 50, 75, or 100 nucleotides from the polypeptide-encoding DNA. In addition to or alternatively, the enhancer may be contiguous to, or be separated by 5, 10, 20, 30, 40, 50, 75, or 100 nucleotides from an APEG-1 promoter or a heterologous promoter.

Preferably, expression of a polypeptide under the control of the APEG enhancer (e.g., SEQ ID No:17, SEQ ID NO:20, or SEQ ID NO:23) is at least 50% greater (e.g., as measured in the amount of polypeptide-encoding mRNA transcript), preferably at least 100% greater, more preferably at least 200% greater, and still more preferably at least 400% greater in vascular smooth muscle cells than in non-vascular smooth muscle cells. Most preferably, the APEG-1 enhancer directs vascular smooth muscle cell-specific polypeptide expression and directs negligible polypeptide expression in non-smooth muscle cell types. The enhancer sequence may in addition regulate developmental stage-specific expression, e.g., preferential expression in embryonic cells, of a polypeptide-encoding sequence.

The DNA of the invention (enhancer sequence) may be operably linked to a DNA sequence encoding a polypeptide that is not APEG-1 (i.e., a heterologous polypeptide), and function to regulate vascular smooth muscle cell-specific transcription of the polypeptide-encoding sequence. Examples of such polypeptides include tissue plasminogen activator (tPA), p21 cell cycle inhibitor, nitric oxide synthase, interferon-γ, and atrial natriuretic polypeptide.

The invention also includes a vector containing the enhancer DNA of the invention (operably linked to a polypeptide-encoding DNA sequence) and a vascular smooth muscle cell containing the vector. Also within the invention is a method of directing vascular smooth cell-specific expression of the polypeptide by introducing the vector into a vascular smooth muscle cell and maintaining the cell under conditions which permit expression of the polypeptide, e.g., introducing the vector into a human patient for gene therapy.

The vector of the invention can be used for gene therapy. For example, the vector can be introduced into a vascular smooth muscle cell to direct vascular smooth muscle cell-specific expression of a polypeptide. The vector of the invention can also be used for directing developmental stage-specific expression, e.g., preferential expression by embryonic cells, of a polypeptide, involving introducing into a vascular smooth muscle cell the vector of the invention.

The invention also features a method of inhibiting proliferation of vascular smooth muscle cells by administering to the cells an APEG-1 polypeptide.

The invention also features a striated muscle cell-specific variant gene product arising from the same genomic DNA encoding APEG-1, and therefore provides a substantially pure DNA (e.g., genomic DNA, cDNA or synthetic DNA) encoding a striated muscle preferentially-expressed gene (SPEG) polypeptide.

The DNA may encode a naturally occurring mammalian SPEG polypeptide such as a human SPEG polypeptide (SEQ ID NO:14) or mouse SPEG polypeptide (SEQ ID NO:16). For example, the invention includes degenerate variants of the human cDNA (SEQ ID NO:13) or the mouse cDNA (SEQ ID NO:15). The invention also includes a substantially pure DNA comprising a strand which hybridizes at high stringency to a DNA having the sequence of SEQ ID NO:13 or 15, or the complements thereof.

A substantially pure DNA having at least 50% sequence identity (preferably at least 70%, more preferably at least 80%, and most preferably at least 90%) to SEQ ID NO:13, or 15, and encoding a polypeptide having a biological activity of a SPEG polypeptide is also within the invention.

The invention also includes a substantially pure DNA containing a constitutive or inducible striated muscle cell-specific promoter, e.g., a SPEG promoter which is preferably in a vector into which an heterologous gene may be or has been cloned, and under the control of which promoter the gene may be expressed. The promoter is preferably specific for striated muscle cells (e.g., cells of skeletal or cardiac muscle). DNA encoding SPEG may be operably linked to such regulatory sequences for expression of the SPEG polypeptide in striated muscle cells.

The invention also provides a method of directing striated muscle cell-specific expression of a protein by introducing into a cell an isolated DNA containing a sequence encoding the protein operably linked to the striated cell-specific promoter. A cell containing the DNA or vector of the invention is also within the invention.

The invention also features a substantially pure SPEG polypeptide (e.g., human (SEQ ID NO:14) or mouse SPEG (SEQ ID NO:16) and an antibody which specifically binds to a SPEG polypeptide.

The invention further features a substantially pure DNA having an APEG-1 derived cis-acting transcriptional repressor sequence. A "cis-acting transcriptional repressor" as used herein is a nucleic acid which functions to decrease transcription of an operably linked nucleic acid sequence. For example, transcription of an operably linked sequence is decreased when a trans-acting repressor, e.g., an endogenous intracellular protein, binds to the cis-acting repressor sequence. Inhibiting binding of the trans-acting repressor, e.g., by administering an exogenous compound that binds to the cis-acting transcriptional repressor, leads to derepression and a concomitant increase in expression of the operably-linked nucleic acid.

The cis-acting transcriptional repressor sequence may be linked to other cis-acting elements, e.g., additional copies of the cis-acting transcriptional repressor sequence. The elements may be contiguous or separated by DNA not involved in the regulation of transcription, e.g., a transcriptional repressor element may be in a position immediately adjacent to the promoter element or up to several kilobases upstream or downstream of the transcriptional start site.

In some embodiments, the cis-acting transcriptional repressor sequence hybridizes to a sequence including nucleotides −3337 to −2663 of the 5' region of the mouse APEG-1 gene (SEQ ID NO:24), or its complement. In other embodiments, the cis-acting transcriptional repressor sequence comprises SEQ ID NO:24, or its complement.

The cis-acting transcriptional repressor sequence can be, e.g., less than 4.0 kb, 3.0 kb, 1.5 kb, 1.0 kb, or even 670 nucleotides in length. In some embodiments, the nucleic acid continuing the cis-acting transcriptional repressor sequence does not include the sequence of SEQ ID NO:23.

The invention also includes a vector comprising the cis-acting transcriptional repressor sequence.

In a further aspect, the invention includes a method of evaluating a compound for the ability to bind to a vascular smooth muscle cell cis-acting transcriptional repressor sequence. The method includes contacting the compound with a vascular smooth muscle cell cis-acting transcriptional repressor sequence and determining the amount of binding of the compound to the vascular smooth cell cis-acting transcriptional repressor sequence. The cis-acting transcriptional repressor sequence can be, for example, a sequence which hybridizes under high stringency conditions to SEQ ID NO:24 and can be SEQ ID NO:24.

In a further aspect, the invention includes a method of evaluating a compound for the ability to bind to a cis-acting transcriptional repressor sequence. In this method, the compound is contacted with a vascular smooth muscle cell containing a nucleic acid comprising a vascular smooth muscle cell cis-acting transcriptional repressor sequence operably linked to a sequence encoding a reporter molecule is contacted. The amount of the reporter molecule expressed by the cell is measured, and an alteration in the level of reporter molecule expressed in the presence of the compound compared to the level in the absence of the compound indicates that the compound binds to a vascular smooth muscle cell cis-acting transcriptional repressor sequence.

In another aspect, the invention includes a method of evaluating a compound for the ability to bind to increase APEG-1 expression. In this method, a vascular smooth muscle cell is contacted with a test compound, and the amount of APEG-1 transcript or polypeptide in the vascular smooth muscle cell is measured. An increase in the amount of APEG-1 transcript or gene product indicates the compound increases APEG-1 expression.

In a further aspect, the invention includes a method of inhibiting vascular smooth muscle cell proliferation by contacting a compound which binds to a vascular smooth muscle cell cis-acting transcriptional repressor sequence. The compound is provided in an amount effective to inhibit proliferation of the vascular smooth muscle cell. In some embodiments, the cis-acting transcriptional repressor sequence includes a sequence which hybridizes at high stringency to SEQ ID NO:24. For example, the cis-acting transcriptional repressor sequence comprises SEQ ID NO:24.

Other features and advantages of the invention will be apparent from the following description of the preferred embodiments thereof, and from the claims.

DETAILED DESCRIPTION

The drawings will first be described.

FIG. 2A is a photograph of a differential mRNA display showing APEG-1 preferentially expressed in the rat aorta. The differential expression was tested among 6 rat tissues.

Figure 1:
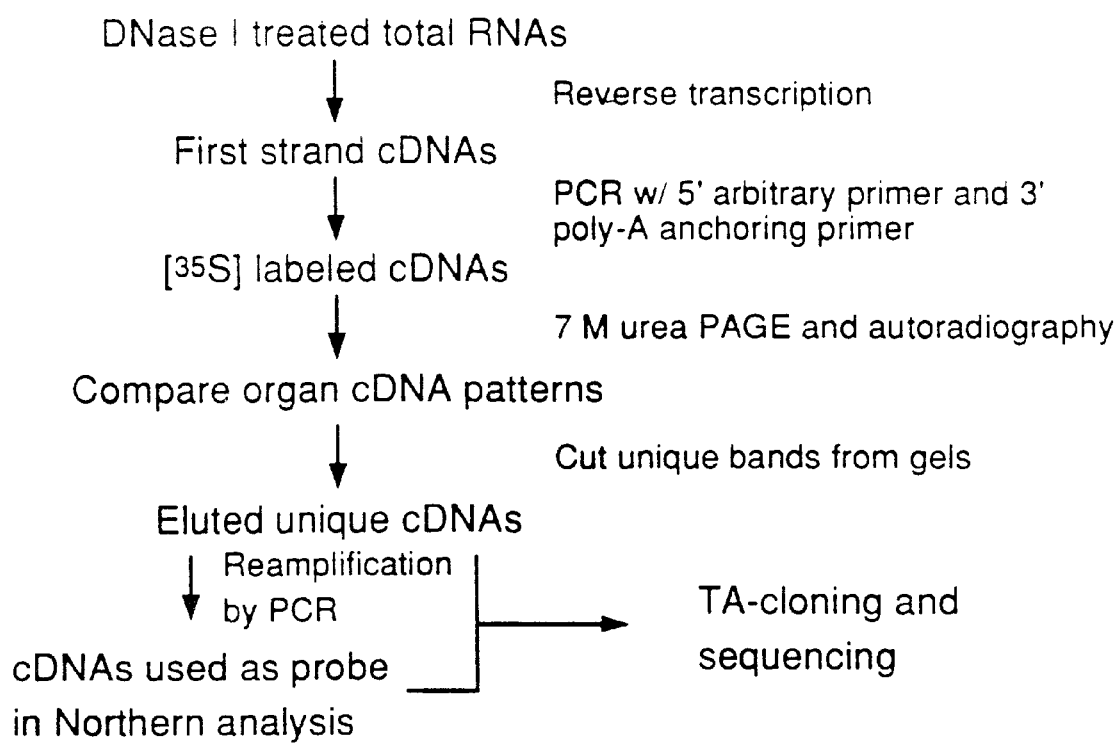
FIG. 1 is a flow chart of the differential mRNA display procedure for identifying APEG sequences.

Unique bands in the aorta that were eluted and reamplified for subsequent analysis are indicated (•).

FIG. 2B is a photograph of a differential mRNA display showing APEG-2 preferentially expressed in the rat aorta. The differential expression was tested among 6 rat tissues. Unique bands in the aorta that were eluted and reamplified for subsequent analysis are indicated (•).

FIG. 2C is a photograph of a differential mRNA display showing APEG-3 preferentially expressed in the rat aorta. The differential expression was tested among 6 rat tissues. Unique bands in the aorta that were eluted and reamplified for subsequent analysis are indicated (•).

FIG. 2D is photograph of a differential mRNA display showing APEG-4 preferentially expressed in the rat aorta. The differential expression was tested among 6 rat tissues. Unique bands in the aorta that were eluted and reamplified for subsequent analysis are indicated (•).

FIG. 2E is a photograph of a Northern blot analysis showing tissue expression of APEG-1. Ten micrograms of total RNA from each tissue were used in Northern analysis. The loading of each tissue RNA was normalized by comparing 18s rRNA hybridization signals (shown in FIG. 2F).

FIG. 2F is a photograph of a Northern blot analysis showing 18s rRNA.

FIG. 2G is a photograph of a Northern blot analysis showing tissue expression of APEG-2. Ten micrograms of total RNAs from each tissue were used in Northern analysis, and the loading of each tissue RNA was normalized by comparing 18s rRNA hybridization signals.

FIG. 2H is a photograph of a Northern blot analysis showing tissue expression of APEG-3. Ten micrograms of total RNAs from each tissue were used in Northern analysis, and the loading of each tissue RNA was normalized by comparing 18s rRNA hybridization signals.

FIG. 2I is a photograph of a Northern blot analysis showing tissue expression of APEG-4. Ten micrograms of total RNAs from each tissue were used in Northern analysis, and the loading of each tissue RNA was normalized by comparing 18s rRNA hybridization signals.

FIG. 3A is a photograph of a Northern blot analysis using full length cDNA of APEG-1 (APEG-1 full cDNA) as a probe. Samples of RNA from twelve rat organs were analyzed. The respective lanes are labelled in FIG. 3D.

FIG. 3B is a photograph of a Northern blot analysis using a 3' cDNA fragment originally cloned by differential mRNA display (APEG-1 3' D.D. frag.) as a probe. Samples of RNA from twelve rat organs were analyzed.

FIG. 3C is a photograph of a Northern blot showing 18s rRNA bands (18s rRNA) to which RNA loading was normalized.

FIG. 3D is a bar graph showing tissue distribution of APEG-1 gene expression.

FIG. 4 is a flow chart showing the cloning strategy for APEG-1. A rat aortic cDNA library established in the yeast expression vector pcJATA was screened to isolate full length APEG-1 cDNA. Southern analysis was carried out to confirm the presence of APEG-1 in this cDNA library. Restriction enzyme-digested (EcoRI and XhoI) cDNA fragments were separated on an agarose gel and the portions that contained APEG-1 cDNA, as determined by size markers and Southern analysis, were excised to elute the cDNA contents. Eluted cDNAs were ligated with linearized pSP72 vectors, and the ligated DNAs were used to transform competent *E. coli* DHα5 cells to establish a size-selected aortic cDNA sublibrary. This cDNA sublibrary was screened by the APEG-1 cDNA 3' fragment to obtain its full length cDNA.

FIG. 5 is a diagram of the nucleotide sequence of rat APEG-1 cDNA (SEQ ID NO:1). The longest open reading frame is located from nucleotide 169 to 511 (BOLD UPPERCASE) and the ATG flanking nucleotides that match the Kozak consensus sequence are indicated (UPPERCASE). A very short upstream open reading frame is present from nucleotide 102 to 116 (italic). There is a polyadenylation signal (underline) 21 nucleotides upstream of the poly-A tail. The primer annealing site of the 5' arbitrary primer used in the initial differential display PCR is also indicated (ITALIC UPPERCASE).

FIG. 6 is a diagram of the amino acid sequence (SEQ ID NO:3) deduced from the longest APEG-1 cDNA open reading frame (SEQ ID NO:2). Possible phosphorylation sites of protein kinase C and casein kinase-2 are indicated (bold). An integrin binding site, RGD, is also shown (bold italic). "***" represents a stop codon.

FIG. 7A is a photograph of in vitro transcription products of the APEG-1 gene. The 1.3 kb APEG-1 cDNA and a positive control DNA template were transcribed by T7 RNA polymerase. 1 µl of the 20 µl RNA products were resolved on a 1.2% denaturing agarose gel.

FIG. 7B is a photograph of in vitro translation products of the APEG-1 gene. In vitro transcribed APEG-1 mRNA was translated by wheat germ extract in the presence of [$^{35}$S]-methionine, and separated on a 10% tricine-SDS-polyacrylamide gel. In the mock reaction, mRNA template was absent.

FIG. 8 is an alignment of amino acid sequences of APEG-1 (SEQ ID NO:8), the myosin light chain kinase of chicken (ChkMLCK; SEQ ID NO:5) and of rabbit (RabMLCK; SEQ ID NO:7), and telokin of chicken (ChkTelo; SEQ ID NO:4) and of rabbit (RabTelo; SEQ ID NO:6). A consensus sequence (SEQ ID NO:9) is also shown to indicate the amino acid residues that are identical among these proteins. The conserved serine residue that is phosphorylated by cAMP-dependent protein kinase is marked by an asterisk (*).

FIG. 9A is a diagram of APEG-1 cDNA. APEG-1 cDNA was divided into four fragments by EcoR I, BamHI, Hind III, and XhoI restriction enzyme digestion. The three large fragments (405, 299, and 432 bp) were used to probe six rat tissue RNAs to show their different hybridization patterns.

FIG. 9B is a photograph of a Northern analysis using the 405 bp fragment of APEG-1 cDNA as a probe.

FIG. 9C is a photograph of a Northern analysis using the 299 bp fragment of APEG-1 cDNA as a probe.

FIG. 9D is a photograph of a Northern analysis using the 432 bp fragment of APEG-1 cDNA as a probe.

FIG. 10 is a photograph of a genomic Southern analysis of the APEG-1 gene. Genomic DNA from cultured rat aortic smooth muscle cells was harvested and digested with EcoRI, HindIII, or BamHI. APEG-1 full length cDNA was used as probe in the Southern analysis. The size of each band (indicated on the right) was determined according to the size markers (indicated on the left).

Figures 11A, 11B:
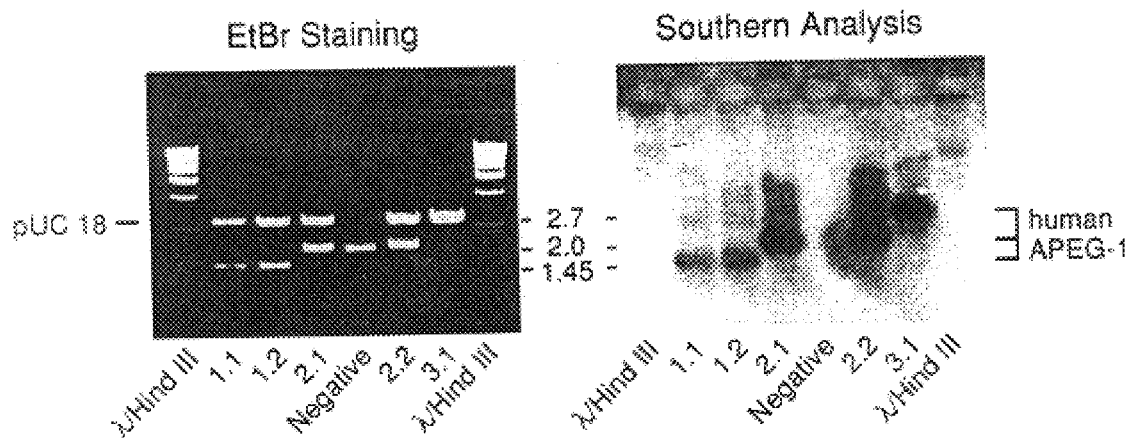

FIG. 11A is a photograph of ethidium bromide staining of the 3 clones of human homologues of rat APEG-1. Clone 1 (1.1, 1.2), clone 2 (2.1, 2.2), and clone 3 (3.1) were 1.45, 2.0, and 2.7 kb in size, respectively.

FIG. 11B is a photograph of a Southern analysis showing hybridization of these human homologues with a rat APEG-1 cDNA probe.

Figure 12:
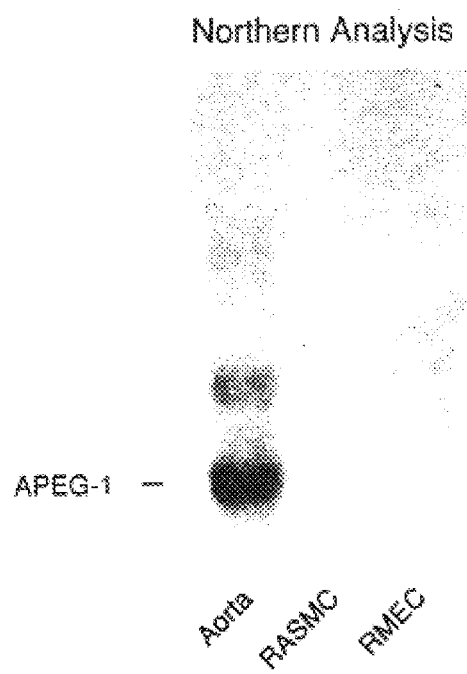

FIG. 12 is a photograph of a Northern analysis of APEG-1 expression in vitro. RNAs from rat aortic smooth muscle cells (RASMC) and from microvascular endothelial cells (RMEC) were purified and separated on a 1.2% denaturing agarose gel. RNA from normal rat aorta was used as a positive control. APEG-1 cDNA was used as probe in Northern analysis to examine its expression in these two cell types.

FIG. 13A is a photograph of a Northern analysis showing expression of APEG-1 in rat carotid artery during balloon injury. RNAs were purified from rat carotid arteries 2, 5, 8 days after balloon injury. Three injured rats were used in each time point and two uninjured rats were used as control. The APEG-1 cDNA was used in Northern analysis and the band intensities were normalized by 18s rRNA signal.

FIG. 13B is a bar graph showing expression of APEG-1 in rat carotid artery during balloon injury. Each column represents the mean expression of APEG-1 in the Northern analysis bands shown in FIG. 13A, expressed as a percent of control±one standard error.

FIG. 14A is a photograph of a Coomassie blue stained 10% tricine-SDS-PAGE gel showing the purified FLAG-APEG-1 fusion protein. M, protein size marker. Ext, induced bacterial cell extracts. FT, cell extract that flowed through the FLAG peptide affinity column.

FIG. 14B is a photograph of a Western analysis of the purified fusion protein. A monoclonal anti-FLAG peptide antibody, M2 (IBI), was used to identify the purity of the fusion protein. Un, uninduced bacterial cell extracts. In, induced bacterial cell extracts. FT, cell extract that flowed through the FLAG peptide affinity column.

Figure 15:
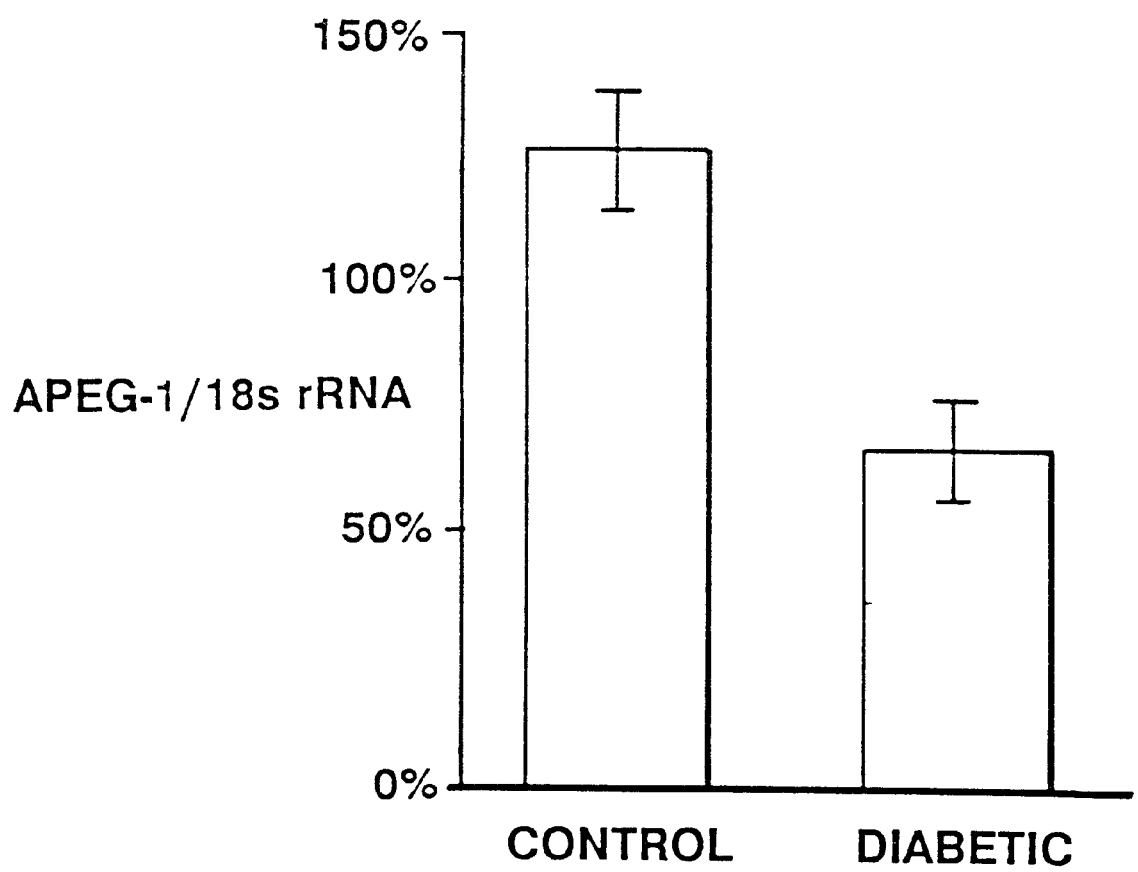

FIG. 15 is a bar graph comparing APEG-1 expression in diabetic rats and control rats. APEG-1 expression was decreased in diabetic rats (unpaired T test: $T_{10}$=3.284, p value=0.0033).

FIG. 16 is a diagram showing the cDNA sequence of human APEG-1 (SEQ ID NO:11)

FIG. 17 is a diagram showing the amino acid sequence of human APEG-1 (SEQ ID NO:12). "*" represents a stop codon.

Figure 18A:
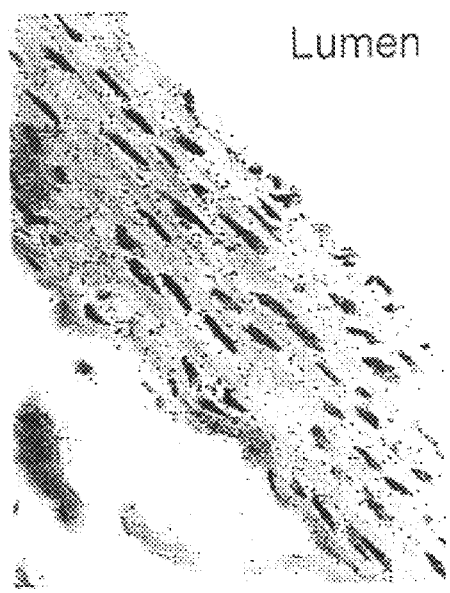

FIG. 18A is a photograph showing the results of an in situ hybridization experiment. The lumen of a rat aorta was sectioned and hybridization carried out using a rat APEG-1 sense strand DNA probe as a control.

Figure 18B:
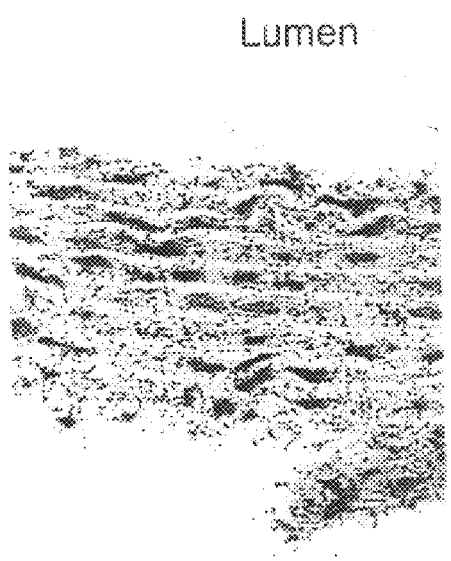

FIG. 18B is a photograph showing APEG-1 mRNA expression in the lumen of a rat aorta. In situ hybridization was carried out using a rat antisense strand DNA probe to measure rat APEG-1 expression in aortic tissue.

FIGS. 19A–C are diagrams showing the pattern of exon usage in the APEG-1 and SPEG transcripts. FIG. 19A is a diagram showing the intron/exon arrangement of the APEG/SPEG locus. FIG. 19B is a diagram showing APEG-1 exon usage. FIG. 19C is a diagram showing SPEG exon usage.

FIGS. 20A and 20B are diagrams showing the cDNA sequence of human SPEG (SEQ ID NO:13).

FIG. 21 is a diagram showing the amino acid sequence of human SPEG (SEQ ID NO:14).

FIGS. 22A and 22B are diagrams showing the cDNA sequence of mouse SPEG (SEQ ID NO:15).

FIG. 23 is a diagram showing the amino acid sequence of mouse SPEG (SEQ ID NO:16).

Figure 24A:
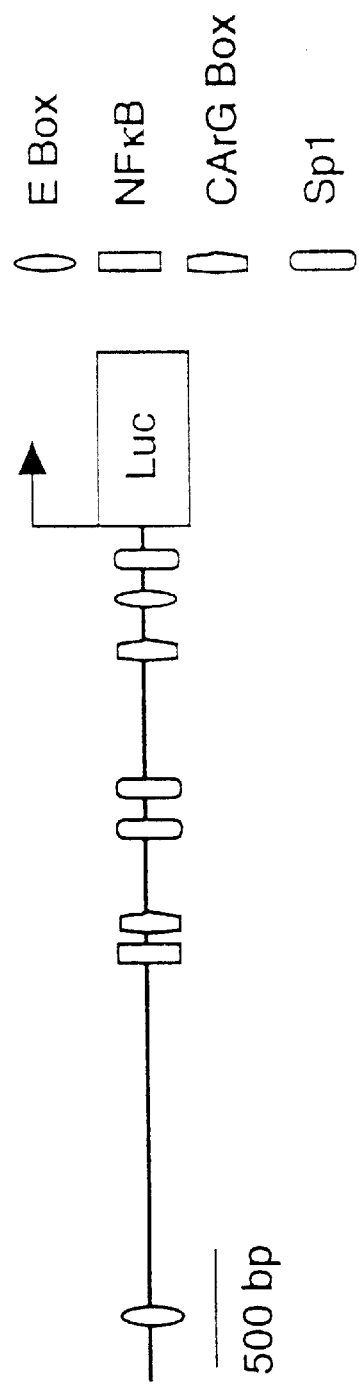

FIG. 24A is a diagram showing the PGL-3 construct.

Figure 24B:
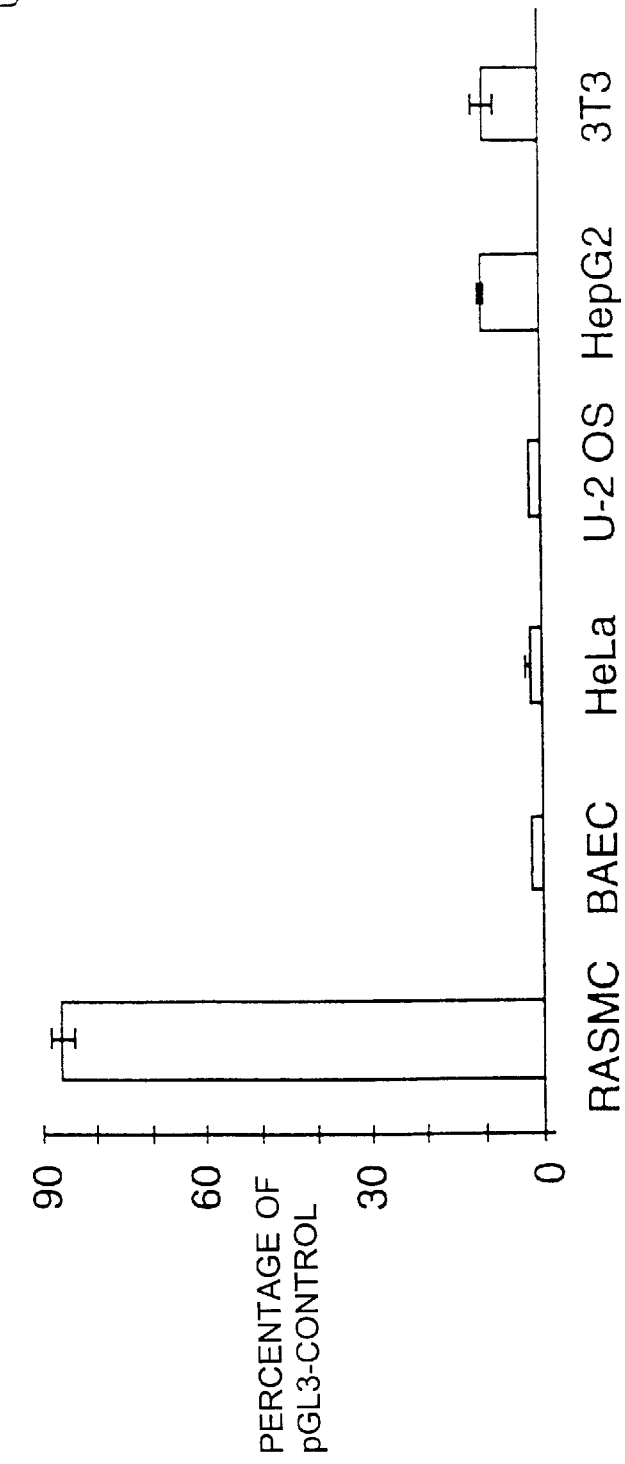

FIG. 24B is a bar graph showing the results of reporter transfection assays using 3.3 kb of APEG-1 5' sequence. Cell lines used: RASMC, rat aortic smooth muscle cells; BAEC, bovine aortic endothelial cells; HeLa, human epidermoid carcinoma cell line; U-2 OS, human osteosarcoma cells; HepG2, human hepatoma cells; NIH 3T3 mouse fibroblasts.

FIG. 25 is a diagram showing the sequence of a 2.7 kb fragment containing the APEG-1 5' vascular smooth muscle cell-specific promoter activity (SEQ ID NO:17).

FIG. 26 is a diagram showing a comparison of the full-length APEG-1 amino acid sequences of the human, mouse and rat.

Figure 27:
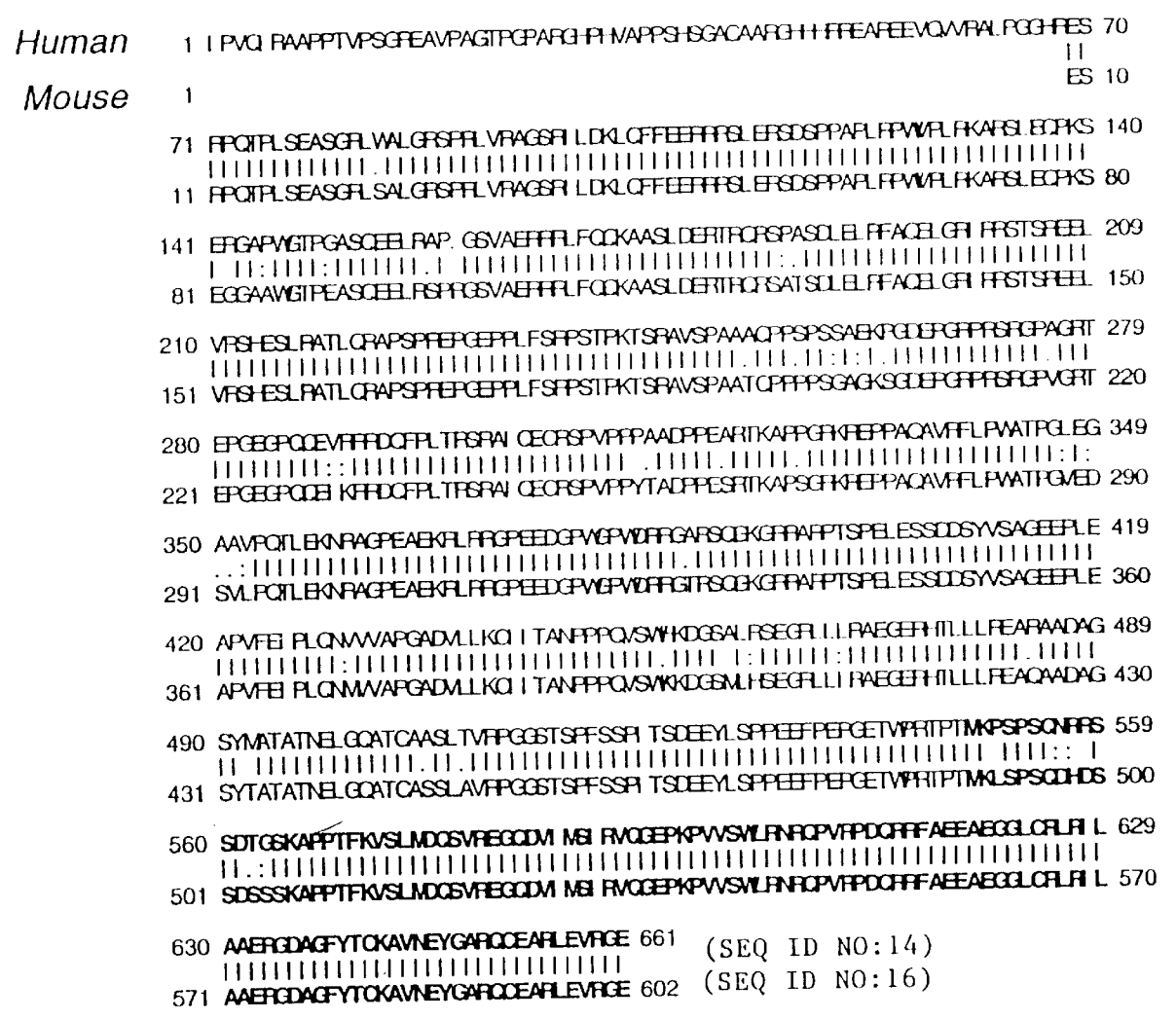

FIG. 27 is a diagram showing a comparison of partial SPEG amino acid sequences in human and mouse. "*" represents a stop codon.

FIG. 28 is a diagram showing the sequence of a 73 nucleotide DNA (SEQ ID NO:20) containing APEG-1 vascular smooth muscle cell-specific promoter activity.

Figure 29:
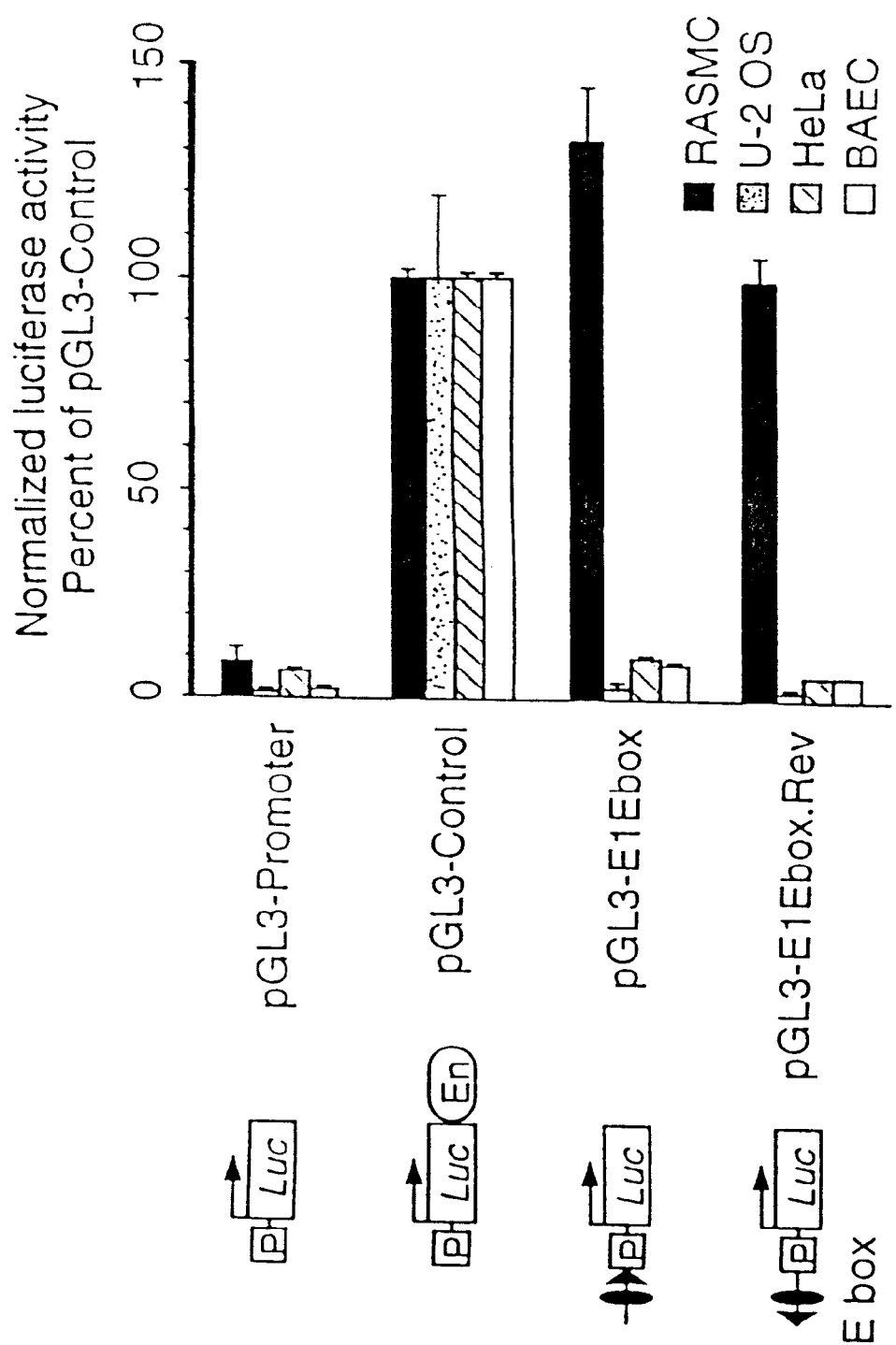

FIG. 29 is a bar graph showing the results of reporter transfection assays using a 73 bp fragment of the APEG-1 5' sequence. Cell lines used: RASMC, rat aortic smooth muscle cells; U-2 OS, human osteosarcoma cells; HeLa, a human epidermoid carcinoma cell line; and BAEC, bovine aortic endothelial cells.

Figure 30:
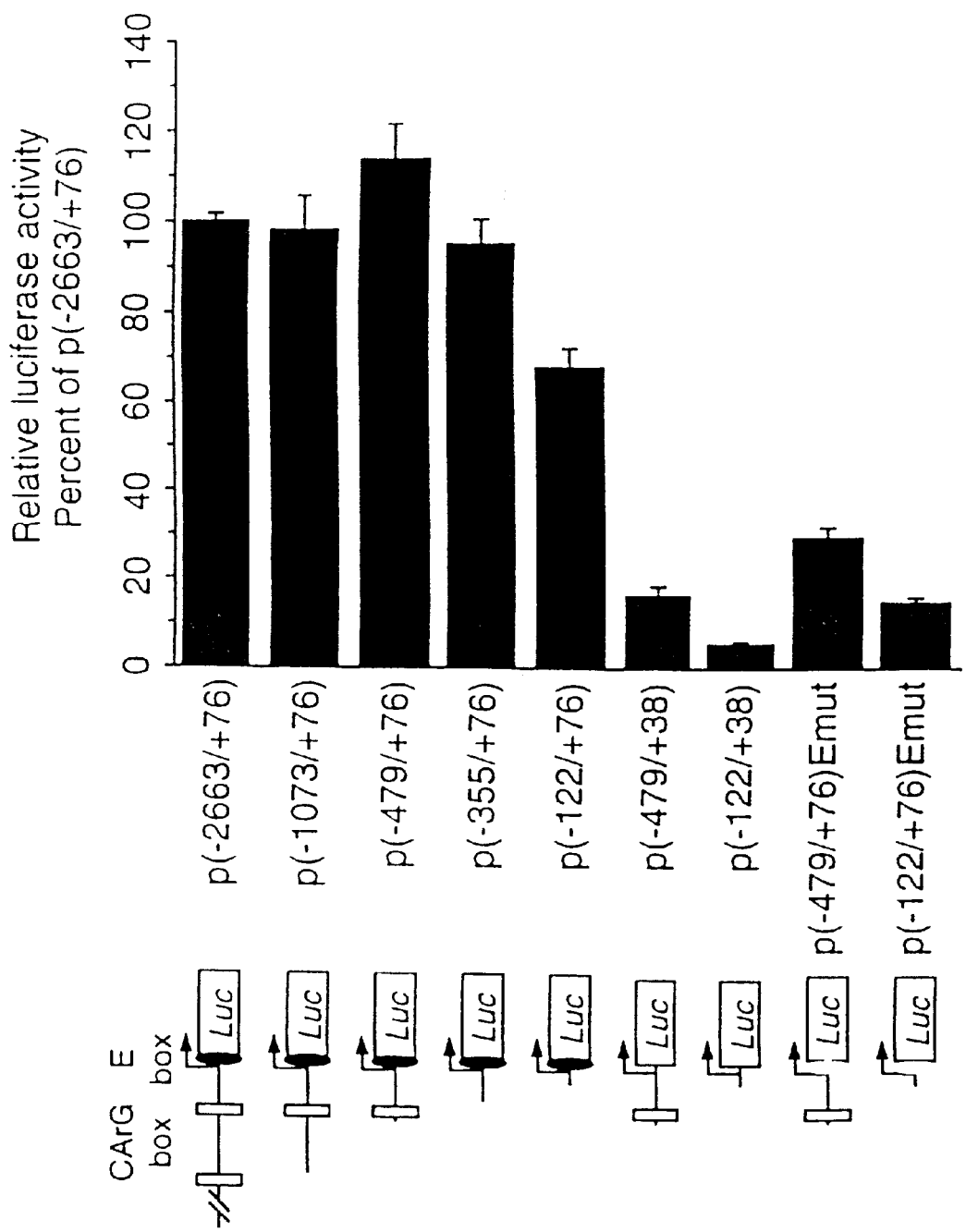

FIG. 30 is a bar graph showing the results of reporter transfection assays using reporter plasmids constructed from the APEG-1 promoter region.

Figure 31A:
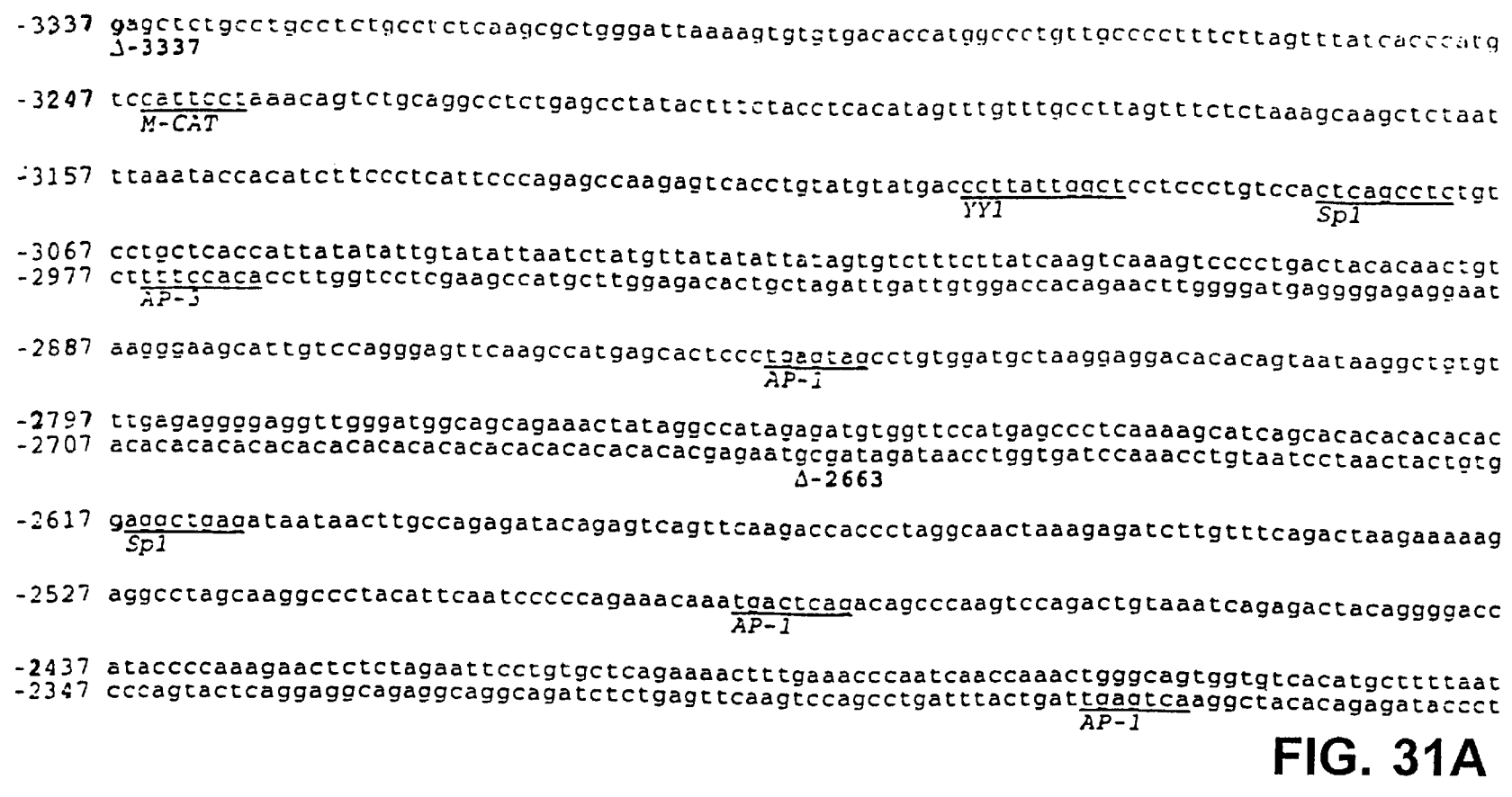

FIGS. 31A, 31B and 31C are diagrams showing the nucleotide sequence from –3337 to +76 of the 5' region of the mouse APEG-1 gene (SEQ ID. NO:24). Open triangles at –3337 and –2663 denote a cis-acting transcriptional repressor sequence, and open triangles at +38 and +76 indicate a cis-acting transcriptional enhancer sequence.

Figure 32:
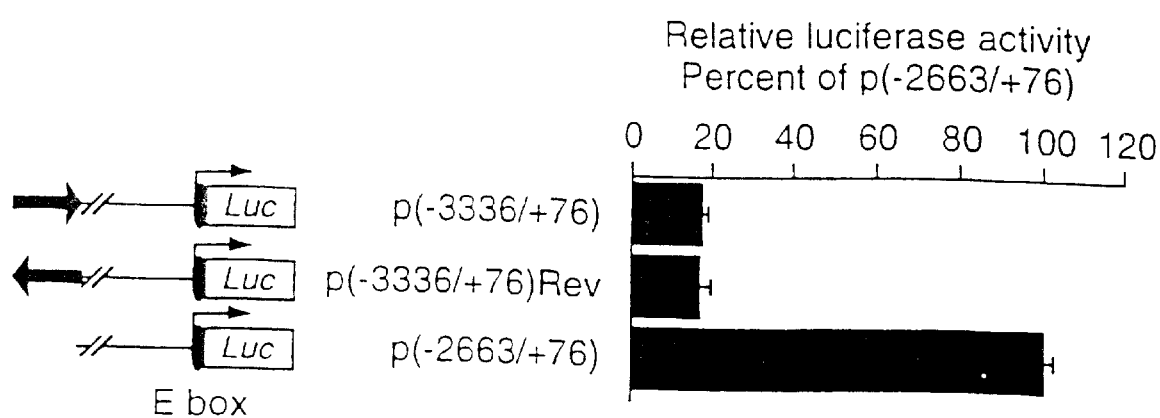

FIG. 32 is a bar graph showing luciferase activity relative in RASMC for constructs p(–33376/+76), p(–33376/+76) Rev, and p(–2663/+76). Activity is shown as a percentage of luciferase activity produced by p(–2663/+76).

Purification of Total RNAs

Total RNA was harvested from male Sprague-Dawley rat organs. The dissected organs were washed in phosphate buffered saline and snap-frozen in liquid nitrogen. The adventitia of the aorta was stripped, and the contents of the small intestine were removed before freezing. The frozen organs were homogenized and RNAs were harvested by acid guanidinium thiocyanate-phenol-chloroform extraction (Chomczynski, P. et al., 1987, Anal. Biochem. 162(1): 156–9). Mouse embryo RNA was harvested from whole embryos. The cell culture RNAs were purified by guanidinium/CsCl ultracentrifugation.

Differential mRNA Display

Fifty micrograms of total RNA were treated with DNase I (Boehringer Mannheim) to remove contaminating genomic DNA in the presence of RNase inhibitor RNasin (Promega). After phenol/chloroform extraction and ethanol precipitation, the RNA concentration was adjusted to 0.1 µg/ml in DEPC-treated dH20. First strand cDNA was synthesized using MMLV reverse transcriptase (GIBCO, BRL) with the 3' poly-A-anchoring primer $T_{12}VG$ (5'-TTTTTTTTTTTVG-3') (SEQ ID NO:10). Subsequently the reaction was heated at 950C to inactivate reverse transcriptase, and the cDNA products were stored at –20 C. Two microliters of the cDNA were used in 20 µl PCR reactions (2 µl cDNA, 0.2 µM 5' arbitrary primer, 1 µM 3' $T_{12}VG$ primer, 1.5 mM $Mg^{2+}$, 2.5 µM dNTP, 12.5 µCi $^{35}S$-dATP, 1 unit Taq DNA polymerase; 94° C. for 15 sec, the thermal cycling was 40° C. for 30 sec and 72° C. for 30 sec; the thermal cycling was repeated for 40 cycles) following the reverse transcription. Sample loading buffer (98% formamide, 0.05% bromophenol blue, and 0.05% xylene cyanol) was added, and the samples were heated at 95° C.

before loading onto a 6% sequencing gel. Overnight exposure of the dried sequencing gels to X-OMAT films (Kodak) was usually sufficient to display the differential mRNA patterns.

Reamplification of Eluted cDNAs

Bands of interest on the dried gel were excised, soaked in 200 µl dH$_2$O for 10 minutes at room temperature, and eluted by heating at 95° C. for 15 minutes. After a brief centrifugation, the supernatants were transferred into fresh tubes, and the eluted DNAs were ethanol-precipitated at −20° C. in the presence of 20 µg glycogen and 300 mM sodium acetate. The precipitated DNAs were collected by centrifugation and washed with 70% ethanol. Dried DNA pellets were resuspended in 10 µl dH$_2$O and nonradioactively reamplified by PCR with the same initial PCR primers and condition, except that the reaction volume was scaled up to 100 µl with 25 µM dNTP. Reamplified cDNAs were resolved on 1% agarose gel to determine their sizes and amounts.

RNA Gel Electrophoresis and Northern Blotting

Ten micrograms of total RNA were heat-denatured and loaded on a denaturing agarose gel (1.2% agarose, 1.1% formaldehyde, 0.5 µg/ml ethidium bromide in MOPS buffer). Electrophoresis was carried out at 10 V/cm for three to four hours. A photograph of the ethidium bromide staining pattern of the RNAs was taken under UV light illumination. The RNAs were then transferred onto a Nitropure membrane (Micron Separation Inc.) by standard blotting procedure (Ausubel, F. M., et al., ed. Current Protocols in Molecular Biology. ed. K. Janssen., 1994, Vol. 1., Current Protocols:4.9.1–14).

DNA Gel Electrophoresis and Southern Blotting

DNAs were loaded and separated on a 1% agarose gel, followed by standard Southern blotting (Ausubel, F. M., et al., ed. Current Protocols in Molecular Biology. ed. K. Janssen., 1994, Vol. 1, Current Protocols: 2.9.1–15). The DNAs in the gel were denatured in denaturation buffer (1.5 M NaCl, 0.5 N NaOH), then neutralized in neutralization buffer (1.5 M NaCl, 1 M TrisCl, pH 7.4) prior to being transferred onto a Nitropure membrane in 20×SSC solution overnight.

Random Priming and Hybridization

Radioactive DNA probes were generated by random priming (Boehringer Mannheim) with 25 to 50 ng of the DNA fragment. Hybridization to the DNA or RNA blots was carried out in QuikHyb solution (Stratagene) with 1×106 cpm/ml of radioactive probes and 0.2 mg/ml herring sperm DNA (Boehringer Mannheim) at 68° C. for one to two hours. The blots were washed and exposed to X-ray films for permanent records.

Quantitation of Hybridization Signals

To quantitate the hybridization signals, DNA and RNA blots were exposed to phosphor screens (Molecular Dynamics) overnight. The phosphor screens were then scanned by a PhosphoImager scanner (Molecular Dynamics) operated by the ImageQuant program (Molecular Dynamics) running on a PC-DOS/MS Windows computer system (Compaq). Intensities of the signals were quantified by the same ImageQuant program following the manufacturer's instructions.

DNA Sequencing and Sequence Analysis

Dideoxynucleotide chain termination DNA sequencing method was used to sequence DNAs. One microliter of DMSO was always included to reduce the DNA template secondary structures that may interfere with the Sequenase (USB) enzymatic activity. The sequences were resolved on 8% sequencing gel (National Diagnostics). The DNA sequences were stored into a local computer mainframe (mbcrr.harvard.edu), and analyzed by a sequence analysis software package (Genetics Computer Group).

Fusion Protein Expression and Purification

Rat APEG-1 cDNA was cloned into pFLAG-2 vector, then transformed into E. coli BL21 cells. Transformed BL21 cells were grown in large scale to an optical density (OD$_{595}$) of 1.75. The cell pellet was resuspended in extraction buffer (20 mM TrisCl, pH 7.4, 0.2 mM EDTA, 1 M NaCl, 1 mM PMSF, 1 mM DTT) and sonicated on ice, after which the extract was frozen and thawed three times in liquid nitrogen and a 42° C. water bath. The soluble cell extract was collected by centrifugation (12,000×g, g, 4° C., 20 minutes) and used in purification of the fusion protein by affinity chromatography with a M2 anti-FLAG peptide mAb affinity column. The column, loaded twice with the soluble cell extract, was washed sequentially with 50 ml of each of the following solutions, TE/NaCl/NP-40 buffer (20 mM TrisCl pH 7.4, 0.2 mM EDTA, 150 mM NaCl, 0.5% NP-40), TE/NaCl buffer (20 mM TrisCl pH 7.4, 0.2 mM EDTA, 150 mM NaCl), and TE buffer (20 mM TrisCl pH 7.4, 0.2 mM EDTA). The FLAG-APEG-1 fusion protein was eluted with 10 ml glycine buffer (0.1 M glycine, pH 3.0) and the eluates were slowly collected in 0.8 ml fractions into microfuge tubes containing 50 µl 1 M TrisCl, pH 8.0, and 150 µl 5 M NaCl solutions. The purity of the purified fusion proteins was assayed by protein electrophoresis and Coomassie blue staining as well as western blotting with anti-FLAG mAb.

Protein Gel Electrophoresis and Western Blotting

A 10% tricine-SDS-polyacrylamide gel system was used to separate bacterial-expressed pFLAG-APEG-1 fusion protein (Schägger, H. et al., 1987, Anal. Biochem. 166:368–79). This system was used because a 10% tricine-SDS-polyacrylamide gel has superior resolution for proteins less than approximately 14 kDa compared to a standard glycine-SDS-polyacrylamide gel. After electrophoresis, the protein gel was assembled in a semi-dry transfer apparatus (Hoefer) and the protein samples were transferred onto a PVDF membrane (Millipore) in transferring buffer (25 mM Tris base, 200 mM glycine, 20% methanol) at 125 mA for one hour.

In Vitro Transcription and Translation

Rat APEG-1 cDNA was cloned into the pSP72 vector and linearized so that RNA could be transcribed from its upstream T7 promoter with the T7 RNA polymerase. Transcription was carried out in a large-scale T7 transcription system (Novagen) in the presence of 7-$^{me}$GpppGTP to produce capped mRNA. The in vitro transcribed mRNA was translated in an in vitro translation system of wheat germ extract (Promega) with the [$^{35}$S]-methionine to produce radiolabeled proteins.

Cellular Localization

The expression plasmid c-myc-rAPEG-1/pCR3 was constructed by adding in frame a DNA sequence encoding a c-Myc peptide tag (EQKLISEED) to the rat APEG-1 open reading frame at the 5' end by PCR techniques known in the art (any other detectable peptide can be used as a tag to localize APEG-1). This hybrid DNA fragment was then cloned in to the eukaryotic expression vector pCR3 (Invitrogen, San Diego, Calif.). COS-7 cells were transiently transfected with the c-myc-rAPEG-1 expressing plasmid by a standard DEAE-dextran method (e.g., the method described in Tan et al., 1994, Kidney Intern. 46:690). The U-2 OS cells were transiently transfected by the calcium phosphate method known in the art. Twenty-four hours after transfection, cells were transferred to two-well chamber slides. The cells were fixed with 4% paraformaldehyde in PBS after growing for an additional twenty-four hours.

Immunostaining was performed with an anti-c-Myc monoclonal antibody (9E10, Oncogene, Cambridge, Mass.) followed by a rhodamine-conjugated goat anti-mouse IgG secondary antibody (Sigma, St. Louis, Mo). Nuclear DNA counterstaining was performed with Hoechst 33258 at a concentration of 1 $\mu$/ml.

Cell Culture

Primary rat aortic smooth muscle cells were maintained in DMEM medium supplied with 10% fetal calf serum, 4 mM L-glutamine, 10 mM HEPES, 100 U/ml penicillin and 100 ng/ml streptomycin. Primary rat microvascular endothelial cells were maintained in DMEM medium supplied with 20% fetal calf serum, 4 mM L-glutamine, 100 U/ml penicillin and 100 ng/ml streptomycin.

BAEC were isolated and cultured in Dulbecco's modified Eagle's medium (JRH Biosciences, Lenexa, Kans.) supplemented with 10% fetal calf serum (HyClone, Logan, Utah), 600 $\mu$g of glutamine/ml, 100 units of penicillin/ml, and 100 $\mu$g of streptomycin/ml.

HepG2 human hepatoma cells (ATCC HB-8065), U-2 OS human osteosarcoma cells (ATCC HTB-96), HeLa human epidermoid carcinoma cells (ATCC CRL-7923), HepG2 human hepatoma cells (ATCC HB-8065), and NIH 3T3 mouse fibroblasts (ATCC CRL-1658) are available from the American Type Culture Collection.

Plasmid DNA Purification

The mini- (<20 $\mu$g) and midiscale (<200 $\mu$g) preparations of plasmid DNA were purified by DNA-affinity chromatography (Qiagen). Large scale purification of plasmid DNA was carried out according to the alkaline lysis/CsCl ultracentrifugation methods (Ausubel, F. M., et al., ed. Current Protocols in Molecular Biology. ed. K. Janssen., 1994, Vol. 1, Current Protocols: 1.7.1–11).

Purification of Recombinant $\lambda$gt11 DNA

Single positive plaques were picked and soaked in the suspension medium (0.1 M NaCl, 10 mM $MgSO_4$, 50 mM TrisCl, pH 7.5, and 0.01% gelatin) with one drop of $CHCl_3$. Freshly prepared E. coli strain Y1090 competent cells were mixed and incubated briefly with the resuspended phage. The infected cells were grown overnight in LB medium with 10 mM $MgSO_4$ and 0.2% maltose. The next morning one drop of chloroform was added into the medium to lyse the bacterial cells for 15 minutes. Bacterial debris was collected by centrifugation, and to the clear supernatant 100 U DNase I and 100 ng RNase A were added to digest E. coli genomic DNA and RNA. The solutions of EDTA, TrisCl (pH 8.0), NaCl, and proteinase K were added subsequently to final concentrations of 50 mM, 100 mM, 200 mM, and 100 ng/ml, respectively. The mixture was incubated at 42° C. for 30 minutes. Phage DNA was then phenol/chloroform extracted once and precipitated by adding 0.6 xvolume of isopropanol in the presence of 300 mM NaOAc. Precipitated phage DNA was recovered by centrifugation and washed with 70% ethanol, air dried, then dissolved in 250 $\mu$l TE buffer (10 mM TrisCl, pH 8.0, 1 mM EDTA).

Cloning APEG-1 Genes

To clone genes that are preferentially expressed in the aorta, total organ RNA was prepared from rat aorta with the adventitia removed, and from brain, skeletal muscle, esophagus, heart, and intestine. Using the differential mRNA display technique, a technique that systematically amplifies mRNAs by means of RT-PCR with different sets of 5' arbitrary primers and 3' oligo-dT anchoring primers, the mRNA patterns of different organs were compared. The PCR products were resolved on a denaturing polyacrylamide sequencing gel to display mRNA patterns that distinguish one organ from another. The bands that were separated by gel electrophoresis represent the 3'-termini of the cDNAs. Therefore, a band that is present in one organ but not in the others suggests that the gene is only expressed in that particular organ (FIG. 1). Specific mRNAs that were present solely in the aorta were identified and cloned.

The organ RNAs were screened with thirty-three 5' arbitrary primers in combination with a $T_{12}VG$ 3' oligo-dT anchoring primer. This initial screening covered 21 percent of the 160 primer combinations needed to screen all possible mRNAs to be displayed by this technique. This estimate is based on the assumption that one primer combination displays about 100 different mRNAs from approximately 15,000 different mRNA species present in each cell.

From the initial screening, seventeen bands that were present solely in the aorta were identified. These bands were cut from the gel and the cDNA fragments eluted and reamplified by PCR with the same primers that were used in their original RT-PCRs. These reamplified cDNAs were $^{32}$P-labeled, then used in Northern blot analyses to confirm their aortic specificity. Four cDNA fragments were found to be aorta-specific (FIGS. 2A–2I). After cloning these four cDNA fragments by TA-cloning methods, the clones were designated APEG-1, APEG-2, APEG-3, and APEG-4. Their DNA sequences were determined by the dideoxynucleotide chain termination method and compared to known DNA sequences listed in the GENBANK® database. APEG-2 showed identical sequences to the rat SM22 gene (Shanahan, C. M., et al., 1993, Circ. Res. 73(1):193–204), a smooth muscle cell specific gene. APEG-4 was found to have a near-identical sequence to chicken and mouse TIMP-3 genes (tissue inhibitor of metalloproteinase-3) (Sun, Y., et al., 1994, Cancer Res. 54:1139–44; Leco, K. J., et al., 1994, J. Biol. Chem. 269(12):9352–60). APEG-1 and APEG-3 did not match any known genes. Further examination of the tissue distribution of expression showed that APEG-3 was also expressed in the lung, a result not seen in the initial Northern blot analysis. In contrast, APEG-1 showed the highest expression in the aorta among twelve rat organs (FIGS. 3A–3D), thus confirming the specificity of tissue expression.

Cloning and Sequence Analysis of Rat APEG-1 cDNA

The APEG-1 3' cDNA fragment, derived from differential mRNA display, was used to screen a rat aortic cDNA library (FIG. 4). The cloned APEG-1 cDNA was determined to be 1,308 base pairs, consistent with the size of the message seen in Northern blot analysis. Sequences of both cDNA strands were determined by dideoxynucleotide chain termination sequencing with fragment-subcloning and oligonucleotide-walking strategies. The complete cDNA sequence had no homologous counterpart in the GENBANK® database.

The rat APEG-1 cDNA can then be used to screen a genomic library to obtain the vascular cell-specific promoter sequences which regulate expression cell-specific expression of APEG-1.

To analyze the protein encoded in APEG-1 cDNA, the sequence was searched for possible ATG initiation codons for translation from the 5' end of the sequence. The longest open reading frame in the rat APEG-1 cDNA (SEQ ID NO:1) spans from 169 to 511 nucleotides (SEQ ID NO:2) downstream of the 5' end of the cDNA. Another ATG sequence was found at nucleotide 102 to 104 (FIG. 5), but the possible translation from this preceding ATG codon is terminated after four amino acid residues, thus making it unlikely to be the initiation codon used in vivo. The longest open reading frame has a Kozak consensus sequence (Kozak, M., 1987, J. Mol. Biol. 196:947–50) and encodes a protein of 113 amino acids (SEQ ID NO:3) with a predicted molecular weight of 12,667 daltons and an estimated pI of 9.125 (FIG. 6). This predicted translation product was confirmed by in vitro transcription and in vitro translation of the APEG-1 cDNA, which yielded a major translation product of 12.7 kDa as predicted by the deduced amino acid sequence from the longest open reading frame (FIGS. 7A–7B). Comparison of the APEG-1 deduced amino acid sequence to the SwissProt protein database again showed no identical protein sequence. However, a region was identified that is homologous to proteins of the myosin light chain kinase family, which includes myosin light chain kinases and telokin (FIG. 8).

The myosin light chain kinases (MLCKs), present in all eukaryotic cells, are members of the $Ca^{2+}$-calmodulin-dependent protein kinases. They phosphorylate the 20 kDa light chain subunit of myosin, a protein that is important in regulating contraction of smooth muscle cells, secretory vesicle movement, cellular locomotion, and changes in cellular morphology (Gallagher, P. J., et al., 1991, J. Biol. Chem. 266(35):23945–52). The structure of MLCKs is highly conserved and composed of several modular domains. The MLCK carboxyl terminus is the calmodulin-binding domain and has a regulatory function mediated by two specific serines residues which become phosphorylated by cAMP-dependent protein kinase. Phosphorylation at these two sites downregulates MLCK kinase activity by decreasing the affinity of MLCK for $Ca^{2+}$-calmodulin. One of the two phosphorylated serine residues in the MLCK C-terminus is conserved in APEG-1 (Ser12), suggesting a regulatory site of APEG-1.

Telokin, originally purified as an acidic protein from turkey gizzard, is a protein that has the same peptide sequence as the carboxyl terminal domain of MLCKs. Its mRNA transcription initiates from a promoter that is located in one of the MLCK introns. Telokin transcription regulation is independent from that of MLCK despite having a sequence identical to the MLCK carboxyl terminal domain. Telokin has been proposed to be a calmodulin-binding protein (Holden, H. M., et al., 1992, J. Mol. Biol. 227:840–51), and it is expressed in almost every smooth muscle cell, except in the aortic smooth muscle cell. It is not expressed in any non-muscle cells (Gallagher, P. J., et al., supra).

When the APEG-1 polypeptide sequence was compared with those of MLCKs, there was a 33% identity at the amino acid level. However, several lines of evidence indicate that APEG-1 is not a rat homologue of a MLCK. First, peptide sequence comparison of APEG-1 to rat smooth muscle MLCK has only 24% identity, significantly less than the identity between APEG-1 and rabbit or chicken MLCKs. Second, the APEG-1 protein is predicted to be a basic protein, whereas the telokin protein is acidic. Third, rabbit telokin is not expressed in the aorta, in contrast to the specific expression pattern of APEG-1.

When the APEG-1 protein was analyzed to identify sequence motifs, several residues were identified as capable of being phosphorylated by protein kinase C and casein kinase-2. An arg-gly-asp (RGD) peptide sequence was found at position 90–92. This motif is present in many proteins involved in cell adhesion as well as signaling, and it interacts with its cell surface receptor, an integrin (Hynes, R. O., 1992, Cell 69:11–25, Ruoslahti, E., et al., 1987, Science 238:491–6). This observation suggests that APEG-1 protein plays role in cell signaling. The motif of two cysteine residues, four residues upstream and six residues downstream of the integrin-binding RGD sequence, are also conserved in the disintegrins, a family of platelet aggregation inhibitors found in snake venom (Blobel, C. P., et al., 1992, Curr. Opin. Cell. Biol. 4:760–5). The cysteine residue 6 residues downstream of the RGD sequence was also found to be present in the APEG-1 protein.

Cloning of Mouse APEG-1

The mouse cDNA encoding an APEG-1 open reading frame was first amplified from mouse aortic RNA by reverse transcription polymerase chain reaction (RT-PCR) with primers conserved between the rat and human sequences. Using nested primers designed according to the open reading frame of mAPEG-1, the 3' end of the mouse cDNA was obtained by 3' RACE. Both strands of the entire mouse APEG-1 cDNA were sequenced at least once by the dideoxy chain termination sequencing method.

Northern and Genomic Southern Analyses of APEG-1

The APEG-1 full length cDNA was used as the probe to hybridize a 12-organ RNA Northern blot. In addition to the 1.3 kb message that appeared in the aorta, two other much larger messages (10–20 kb) were observed in skeletal muscle, esophagus, and heart. These two large messages were not initially identified by the APEG-1 3' -probe; therefore, it is likely the 5' sequence of APEG-1 cDNA hybridized to these new signals. To test this possibility further, three different probes from the 5', the middle, and the 3' portions of the APEG-1 cDNA sequence were used in Northern analysis (FIG. 9A). The result indicated that these 10–20 kb messages were recognized by the 5' but not by the 3' portion of the APEG-1 cDNA (FIGS. 9B–9D).

To determine the relationship of the 1.3 kb aortic transcript and the larger transcripts, a series of probes spanning the APEG-1 gene was used in Northern blot hybridization analyses of RNA isolated from rat aorta, heart, and skeletal muscle. This analysis revealed that the APEG-1 gene defines a muscle cell-specific protein family that encodes both smooth muscle cell-specific proteins and striated muscle cell-specific proteins. The APEG-1 transcripts were detected only in aortic RNA. The large transcripts correspond to variant isoforms, which have been named SPEGs. SPEGs are detected in striated muscle RNA (skeletal and cardiac tissue) but were not seen in aortic RNA.

The patterns of exon usage in APEG-1 and SPEGs are shown in FIGS. 19A–C. The APEG-1 gene spans 4.5 kb and is composed of five exons and four introns. SPEG-specific probes detect transcripts 10 and 12 kb in size that are composed of at least seven exons. Three of these exons are shared with the APEG-1 gene, while at least four are unique. The first exon of APEG-1 is separated from the closest upstream SPEG exon by 7 kb. The differential tissue expression patterns of APEG-1 and SPEG arise from utilization of different promoters, alternative splicing, or a combination of the two mechanisms.

The partial nucleotide and amino acid sequences of human SPEG are shown in FIGS. 20A and B and FIG. 21, respectively. The partial nucleotide and amino acid sequences of mouse SPEG are shown in FIGS. 22A, 22B and 23, respectively. A comparison of the human and mouse partial SPEG amino acid sequences is shown in FIG. 27.

Chromosomal Location of the APEG-1 Gene

The APEG-1 gene was mapped to human chromosome 2q33–34, which is a region containing several genes involved in cardiovascular disease.

Identification of APEG-1 Associated Sequences Conferring Vascular Smooth Muscle Cell Gene Expression To determine whether a smooth muscle cell specific promoter exists 5' to the first APEG-1 exon, a 3.3 kb APEG-1 5' flanking sequence was used in a reporter gene transfection analysis using the luciferase reporter plasmid pGL3–C. As shown in FIGS. 24A–B, a high level of promoter activity directed by the APEG-1 5' flanking sequence was detected in both rat aortic smooth muscle cells human aortic smooth muscle cells. In contrast, as shown in FIG. 24A–B, minimal activity was detected in five non-smooth muscle cell types, including human cell lines HeLa, HepG2, and U-2 OS.

The sequences responsible for directing a high level of promoter activity have been further localized within the 3.3 kb fragment to the 2.7 kb sequence shown in FIG. 25.

APEG-1 sequences able to confer vascular smooth muscle cell specific gene expression have been still further localized within the 2.7 kb sequence to a 73 nucleotide sequence (SEQ ID NO:20) shown in FIG. 28. The sequence corresponds to nucleotides 2666 to 2738 of the sequence shown in FIG. 25 (SEQ ID NO:17), and to nucleotides +4 to +76 of the APEG-1 transcript, wherein +1 is the first transcribed nucleotide as determined by RNAse protection assays and 5' RACE PCR amplification. The 73 nucleotide sequence includes two AP-2 binding motifs and one E-box binding motif.

To demonstrate its ability to confer VSMC specific transcription, the 73 bp sequence was cloned in both orientations into the SmaI site of the pGL3-Promoter to generate pGL3-E1box and pGL3-E1Ebox.Rev, respectively. The pGL3-E1box and pGL3-E1Ebox.Rev constructs are shown schematically in the left-hand portion of FIG. 29. The APEG-1 derived sequence is shown as a filled oval, to denote the E-box containing region, and with an arrowhead to indicate the relative orientation of the 73 bp sequence in the two plasmids. Both plasmids in addition contain a promoter (P) derived from SV40.

Also shown in the schematic diagram are control constructs pGL3-Promoter, which contains the SV 40-derived promoter (P) but lacks an enhancer element, and pGL3Control, which contains the SV40 promoter (P) and an SV40 enhancer region (En). The SV40 enhancer region is able to direct transcription in a variety of cell types.

The constructs were each transfected into rat aortic smooth cells (RASMC), U-2 OS, HeLa, and BAEC cells. Their ability to activate transcription of the SV40 promoter was determined by measuring luciferase activity. The luciferase activity for each construct in the respective cell types is shown in the right-hand portion of FIG. 29. For the data shown, luciferase activity was measured in each cell type as a percent of the luciferase activity of the pGL3-Control. Each bar represents the mean±SEM.

In all of the cell types examined, the PGL3-Promoter construct demonstrated negligible luciferase activity. In contrast, the pGL3-Control plasmid, which contains the SV40 enhancer, was active in all cell lines. Both pGL3-E1 Ebox and pGL3-E1 Ebox.Rev expressed levels of luciferase activity comparable to control pGL3-Control only in RASMC. The promoters directed little or no luciferase in the U2-OS, HeLa, or BAEC cell lines. These results demonstrate that the 73 bp sequence from APEG-1 activates RASMC-specific transcription in an manner that does not depend on the orientation of the 73 bp sequence with respect to the SV40 promoter.

The 73 bp sequence was further characterized in gel mobility shift assays for binding activity upon incubation with nuclear extracts. Studies were done using two 18 bp double-stranded oligonucleotides derived from the mouse APEG-1 exon 1 sequence. One 18-mer oligonucleotide, named the E oligonucleotide, had the sequence 5'GGGCCTCAGCTGGGTCAG-3' (SEQ ID NO:21). This sequence corresponds to the E box motif in the 73 bp fragment, as well as 6 nucleotides upstream and downstream of the E box. The second oligonucleotide, named the Emut oligonucleotide, had the sequence 5'-GGGCCTCAGCACGGTCAG-3' (SEQ ID NO:22). The Emut oligonucleotide was identical in sequence to the E oligonucleotide except that the nucleotide TG in the E box sequence changed to AC in the corresponding positions in the Emut sequence.

Each oligonucleotide was end-labeled with [γ-32P]ATP and incubated with or without RASMC nuclear extract. Omission of RASMC nuclear extract resulted in each labeled oligonucleotide migrating at the positions expected for the free oligonucleotide.

Incubation of the E oligonucleotide with the RASMC extract retarded the mobility of the oligonucleotide relative to its migration as a free nucleotide. No altered mobility was observed if the labeled E oligonucleotide was incubated with RASMC nuclear extract in the presence of a 100-fold molar excess of unlabeled E oligonucleotide. In contrast, an altered mobility was still observed following incubation of the labeled E oligonucleotide with RASMC nuclear extract in the presence of a 100-fold molar excess of unlabeled Emut oligonucleotide, or with an unlabeled oligonucleotide having a sequence unrelated to the E oligonucleotide.

No altered mobility was observed upon incubation of labeled Emut oligonucleotide and the RASMC nuclear extract. These results show that the Ebox-containing motif binds to one or more components of RASMC nuclear extracts in a sequence-specific manner.

Binding to the 73 nucleotide region by a component of RASMC nuclear extracts was also determined in a DNase I footprint assay. An APEG-1 genomic DNA sequence corresponding to the nucleotides from −132 to +76 bp was radiolabeled at either the 5' or 3' end with Klenow fragment and [α-$^{32}$P]dNTP. The end-labeled probes were incubated with either bovine serum albumin (BSA) or RASMC nuclear extract and subjected to varying amounts of DNaseI digestion. Incubation with RASMC nuclear extract resulted in protected regions corresponding to the AP2 and Sp1 binding motifs in the APEG-1 genomic sequence. No protection of these regions were observed upon incubation with BSA.

The AP2 and SP1 regions were similarly protected when the DNAseI studies were performed on a fragment having nucleotides −490 to +76 of the genomic APEG-1 sequence. Together, the DNAse I footprint studies reveal that VSMC nuclear extracts have one or more components that bind to the APEG-1 promoter region.

A series of 3' deletion constructs based on constructs containing nucleotides −479 to +76 of the 5' APEG-1 region, or nucleotides −122 to +76 of the 5' region (p(−479/+76) and p(−122/+76), respectively) were constructed to further localize the positive cis-acting element and to confirm the presence of the 76-bp exon 1 sequence was important for promoter activity. The constructs were transfected into RASMC and the amount of luciferase activity relative to luciferase generated by a p(−2663/+76) construct determined. The results are shown in FIG. 30.

Four 5' deletion constructs (p−1073/+76), p(479/+76), p(−355/+76) and p(−122/+76) were made from p(−2663/+76). The results demonstrate that most of the APEG-1 promoter activity is contained within p(−122/+76). Two 3' deletion constructs p(−479/+38) and p(−122/+38), which were made from p(−479/+76) and p(−122/+76), showed minimal promoter activity. The p(−479/+76)Emut and p(−122/+76)Emut constructs contain a 2-bp mutation that changes the E box motif in exon 1 from CAGCTG to CAGCAC. The diagram on the left of FIG. 30 shows the relative lengths of the constructs and the positions of the CArG boxes (white boxes) and the E box (black ovals). The E box mutation is indicated by the hatched ovals. Transfection experiments were repeated at least three times for each construct, and promoter activity is expressed as a percentage of p(−2663/+76) activity.

In comparison with p(−479/+76), sequences including −479 to +38 of the APEG-1 5′ region or −122 to −38 of the 5′ region both had much lower promoter activity (16% and 4%, respectively) These results demonstrate that the sequence between bp +38 and +76 (SEQ ID NO:23) in exon 1 is essential for APEG-1 promoter activity. The sequence of SEQ ID NO:23 is shown in FIGS. 31A–C as the sequence defined by open triangles at nucleotides +38 and +76.

The sequence between bp +38 and +76 includes an E box motif (CAGCTG) at bp +39 to +44 (FIGS. 31A–C). To determine if this sequence is required for activity, a construct was prepared in which CAGCTG sequence was altered to CAGCAC in the constructs p(−479/+76) and p(−122/+76). As shown by transfection experiments with p(−479/+76) Emut and p(−122/+76)Emut, mutation of the exon 1 E box motif caused a dramatic reduction in APEG-1 promoter activity (FIG. 30). These data show that this E box motif located at the 5′-untranslated region (5′-UTR) is essential for high-level APEG-1 promoter activity in RASMC.

Although not commonly found, transcription regulatory elements have been documented to locate to the 5′-UTR of a few other genes. For instance, the 5′-UTR of the herpes simplex virus type 1 ICP22 gene and the human integrin β3 gene have been reported to contain cis-acting elements that mediate high-level expression of these genes (Greco et al., J. Gen. Virol. 75:1693–1702, 1994; Wilhide et al., Blood 90:3951–61, 1997). Furthermore, the human Aγ-globin gene also has regulatory elements in the 5′-UTR. One of these elements binds to the erythroid transcription factor GATA-1 and may regulate transcription of the human Aγ-globin gene during development (Amrolia et al., J. Biol. Chem. 270:12892–12898, 1995).

It is noteworthy that one CArG box and one Carg-like box are located at bp −1531 to −1522 and bp −443 to −434 of the APEG-1 5′-flanking region, respectively. The Carg box is crucial to the expression of several other SMC-specific genes (Kim et al., Mol. Cell. Biol. 15:2266–2278, 1997; Herring et al., Am. J. Physiol. 272:C1394–1404, 1997; Shimizu et al., J. biol. Chem. 270:7631–43; Madsen et al., J. Biol. Chem. 272:6332–6340, 1997), although there is no known SMC-specific, Carg box-binding protein. In the case of the APEG-1 promoter, however, deletion of the Carg and Carg-like boxes did not alter its activity (FIG. 30), indicating that the two boxes are dispensable. This dispensability distinguishes APEG-1 from other SMC-specific genes and suggests the existence of Carg-independent mechanisms of SMC-specific gene expression. Indeed, the Carg-less promoter of mouse CRP2/SmLIM has been shown to direct a high level of VSMC-specific reporter gene expression in transgenic mice (Yet et al., J. Biol. Chem. 273:10530–37, 1998).

Sequences capable of directing striated muscle specific expression of the SPEGs exons are determined by performing the above-described cell transfection assays using sequences 5′ to the first SPEG exon.

Identification of a Transcriptional Repressor Sequence in the 5′ Region of the APEG-1 Gene The expression of APEG-1 is down-regulated in dedifferentiated VSMC both in vivo and in vitro. Thus, it was unexpected that the 2.7 kb (SEQ ID NO:17) of the APEG-1 5′-flanking region directed high levels of promoter activity in cultured, and therefore dedifferentiated, RASMC. One explanation for this anomaly is the presence of negative DNA regulatory elements outside the 2.7-kb APEG-1 5′-flanking sequence.

To test this possibility, plasmids p(−3336/+76) and p(−3336/+76)Rev were constructed by cloning an additional 685 bp of APEG-1 5′-flanking sequence into p(−2663/+76), in both orientations. The nucleotide sequence −3336 to +76 (SEQ ID NO:24) is shown in FIGS. 31A–C at the open triangles at these nucleotide positions.

As is shown in FIG. 32, the promoter activity of p(−336/+76) and p(−3336/+76)Rev was only 20% of the activity of the 2.7-kb APEG-1 promoter construct p(−2663/+76). An additional (upstream) 4-kb DNA sequence did not further decrease promoter activity. These results reveal that an orientation-independent transcription repressor is located between bp −3336 and −2663 (SEQ ID NO:24).

Expression of APEG-1 and SPEG in Mouse Development

The full-length APEG-1 cDNA was used to probe RNA isolated from mouse embryos at different times in embryonic development. RNA was isolated from the entire embryo for these experiments. The APEG-1 probe hybridized to a 1.3 kb RNA from embryos beginning 9.5 days post-coitus (p.c.) and continuing to 20 days p.c. Strong hybridization was observed to RNA from embryos 11.5 to 20 days p.c.

APEG-1 transcript levels were also examined post-natally in RNA isolated from rat heart tissue. Hybridization to the APEG-1 probe was detectable in RNA from two-day old rats, but only faint hybridization was detected in RNA from rats aged 14 and 28 days. In situ hybridization experiments of post-natal heart tissue using the APEG-1 probe also revealed a decreased level of APEG-1 RNA. Interestingly, as APEG-1 RNA levels decreased, the levels of SPEG RNAs in striated muscle increased.

When considered with the tissue specific expression data, these results suggest that APEG-1 transcript levels are high during embryonic development, particularly at day 11.5 p.c. and thereafter. Post-natally, APEG-1 transcript levels, e.g., in cardiac muscle, was generally found to decrease. As global APEG-1 levels decreased, SPEG transcript levels in striated muscle cells increased.

Southern blot analysis suggested that APEG-1 has a single copy in the rat genome, because there was only one 17.1 kb band in the EcoR I-digested rat genomic DNA (FIG. 10). This result further indicated that the large messages are unlikely to be products of other genes, unless these other genes are closely linked with APEG-1 without any intervening EcoR I sites. From the APEG-1 cDNA sequence two BamH I and one Hind III site were located (FIG. 9A). This correlated with the Southern analysis data in that three bands (18.7, 2.4, and 1.4 kb) in BamH I- and two bands (12.0 and 6.4 kb) in HindIII-digested genomic DNA were identified.

Cloning of the Human APEG-1 cDNA

The APEG-1 cDNA probe was used to screen a human λgt11 aortic 5′-stretch cDNA library (Clontech). Four positive clones were purified, and the insert cDNA was sized by EcoRI digestion of the phage DNA and sequenced. The sequence of the human APEG-1 cDNA and the predicted amino acid sequence of the open reading frame encoding human APEG-1 are shown in FIG. 16 and FIG. 17, respectively.

The human APEG-1 cDNA can then be used to screen a genomic library to obtain the vascular cell-specific promoter sequences which regulate expression cell-specific expression of APEG-1.

Comparison of the Human, Mouse, and Rat APEG-1 Peptide Sequences

FIG. 26 shows the aligned human, mouse, and rat APEG-1 peptide sequences, along with a derived consensus sequence (SEQ ID NO: 12, 18, 13, and 19). A comparison of the human and rat open reading frames revealed 90% identity at the cDNA level and 97% identity at the amino acid level. Comparison of the open reading frames of mouse and rat APEG-1 revealed 95% identity at the cDNA level and 98% identity at the amino acid level. Thus, APEG-1 is highly conserved across species.

Deposit

A plasmid containing DNA encoding rat APEG-1 (rat APEG-1 cDNA in pSP72 vector) has been deposited with the American Type Culture Collection (ATCC) under the terms of the Budapest Treaty on the International Recognition of the Deposit of Microorganisms for the Purpose of Patent Procedure on Mar. 3, 1995, and bears the accession number ATCC 97071. A plasmid containing DNA encoding human APEG-1 (human APEG-1 cDNA in pUC18 vector) was deposited with the American Type Culture Collection under the terms of the Budapest Treaty on Jun. 1, 1995, and bears the accession number ATCC 97180. A deposit of a plasmid clone containing 2.7 kb of 5' flanking sequence of the mouse APEG-1 gene was deposited with the ATCC on Feb. 5, 1997. Applicants' assignee, President and Fellows of Harvard College, acknowledges its duty to replace the deposit should the depository be unable to furnish a sample when requested due to the condition of the deposit before the end of the term of a patent issued hereon, and its responsibility to notify the ATCC of the issuance of such a patent, at which time the deposit will be made available to the public. Prior to that time, the deposit will be made available to the Commissioner of Patents under the terms of CFR §1.14 and 35 U.S.C. §112.

The Absence of APEG-1 Expression in Primary Culture Cells

As discussed above, APEG-1 was initially identified in adventitia-removed aortic tissue, a tissue composed of smooth muscle cells and endothelial cells. To identify which of these two cell types express APEG-1 gene, total RNAs were harvested from primary cultured rat aortic smooth muscle cells and microvascular endothelial cells, both at the second passage, and these RNAs were used in Northern analysis. APEG-1 message was not detected in these cell types (FIG. 12). It is likely that the in vivo expression of APEG-1 was lost during in vitro cell culture. These data suggest that APEG-1 expression is strictly growth-regulated, such that its expression is downregulated when cells are growing in vitro, as has been observed with respect to gas1 gene expression (Sal, G. D., et al., 1992, Cell 70:595–607). Alternatively, since cultured smooth muscle cells are believed to exhibit a dedifferentiated phenotype (Pauly, R. R., et al., 1992, Circulation 86 (suppl III):III–68–73), APEG-1 may be expressed solely in fully differentiated endothelial or smooth muscle cells. Consistent with a role in maintaining a differentiated phenotype, which is characterized by the absence of cell division, microinjected APEG-1 inhibited BrdU uptake in rat arterial smooth muscle cells. APEG-1 expression in vivo was found to be vascular smooth muscle cell-specific, as shown in FIGS. 18A and 18B.

APEG-1 Expression in the Balloon Injury Animal Model

Since APEG-1 gene expression in vitro is different from that in vivo, APEG-1 expression in vivo was studied. A balloon injury model of the rat carotid artery, which has been used extensively to study vascular smooth muscle cells in atherogenesis and vascular remodeling (Clowes, A. W., et al., 1983, Lab. Invest. 49(2):208–15, Clowes, A. W. et al., 1985, Circ. Res. 56:139–45), was used to study the expression modulation of APEG-1. In this animal model, the rat left carotid artery was injured by a 2F balloon catheter, intimal arterial endothelial cells completely removed, and the medial smooth muscle cell layer distended. After the carotid injury, formation of the neointima was initiated. This involves smooth muscle cells proliferating and migrating from the media. With this model, medial and neointimal smooth muscle cells reach their respective highest rates of proliferation two days and four days after the balloon injury, declining rapidly thereafter. The total number of smooth muscle cells approaches a maximum and remains constant after two weeks (Clowes, A. W. et al., 1985, supra).

Total RNAs from rat carotid arteries 2, 5, and 8 days after balloon injury were collected and used in Northern analysis with an APEG-1 cDNA probe. The results showed that APEG-1 is downregulated to 15%-20% of non-injured carotid arteries after 2 and 5 days; the expression recovered to 40% of control after 8 days (FIGS. 13A and 13B). These data suggest that APEG-1 expression is involved in the regulation of smooth muscle cell proliferation and/or migration, and expression has to be suppressed for either or both events to occur.

Production and Purification of Recombinant APEG-1

Recombinant APEG-1 was expressed as a fusion protein and purified by the pFLAG expression system (IBI) and subsequently injected into rabbit to produce antiserum. The rat APEG-1 cDNA was cloned into pFLAG-2 expression vector and used to transform the E. coli BL21 cells. The transformed cells were grown and induced by IPTG (isopropyl-β-D-thio-galactopyroside) to express the vector-encoded fusion protein. The FLAG-APEG-1 fusion protein was then purified by anti-FLAG monoclonal antibody affinity chromatography from soluble cell extract, and the purity was monitored by both Coomassie blue staining (FIG. 14A) and Western analysis (FIG. 14B).

APEG-1 Cellular Localization

To determine the cellular localization of APEG-1, a plasmid was generated, c-myc-rAPEG-1/pCR3, that would express a fusion protein of APEG-1 with an N-terminal c-Myc tag. COS-7 cells were then transiently transfected with the c-myc-rAPEG-1/pCR3 plasmid and immunostained with a monoclonal anti-c-Myc antibody, 9E10. The c-Myc-tagged protein was expressed predominantly in the nuclei of transfected COS-7 cells. The same result was obtained when U-2 OS cells were used as the host cells.

Methods of Diagnosis

The invention includes a method of detecting injury in a sample of vascular tissue. A depressed level of APEG-1 would predict a high degree of smooth muscle cell proliferation indicative of vascular tissue injury, e.g., restenosis. The diagnostic method of the invention is carried out by determining the level of APEG-1 gene expression in a tissue, e.g., a vascular biopsy obtained at atherectomy. The level of gene expression may be measured using methods known in the art, e.g., in situ hybridization, Northern blot analysis, or Western blot analysis using APEG-1-specific monoclonal or polyclonal antibodies. A decrease in the level of APEG-1 expression per cell in the test sample of tissue compared to the level per cell in uninjured control vascular tissue indicates the presence of a vascular injury in the test sample. For example, tissue obtained at atherectomy could be tested for APEG-1 expression, e.g., the level of APEG-1 transcript or protein. A depressed level of APEG-1 (compared to normal tissue) correlates with a high degree of smooth muscle cell proliferation indicating a high probability of restenosis. Such diagnostic procedures are useful to identify patients in need of therapeutic intervention to reduce or prevent restenosis.

Methods of Detecting Specific Types of Muscle Cells

Because APEG-1 and SPEG mRNAs are enriched in vascular smooth muscle cells and in striated muscle cells, respectively, the APEG-1 and SPEG nucleic acid sequences can be used as probes to identify these cell types. For example, an APEG-1 specific nucleic acid sequence, e.g., a probe corresponding to an APEG-1 specific exon, is hybridized, using methods well known in the art, to RNA sequences in Northern blot hybridization studies or using in situ hybridization assays. Reactivity to an APEG-1 specific probe is indicative of a vascular smooth muscle cell tissue. Similarly, a SPEG-specific nucleic acid sequence, e.g., a probe corresponding to a SPEG-specific exon, is used to identify striated muscle cells.

APEG-1 and SPEG DNA sequences can also be used to make recombinant APEG-1 and SPEG polypeptides, or fragments thereof. Monoclonal or polyclonal antibodies are then raised to the recombinant polypeptides using methods well-known in the art. The anti-SPEG antibodies are then used, e.g., in western or immunofluorescence experiments, to identify vascular smooth muscle cells, in the case of APEG-1, or striated muscle cells in the case of SPEG.

Methods of Therapy

Upon vascular injury and other stimuli, cytokines and growth factors from activated vascular cells promote growth and migration of dedifferentiated vascular smooth muscle cells, resulting in atherosclerotic plaques and restenosis. Administration of APEG-1 polypeptide to vascular smooth muscle cells in vitro (by microinjection) resulted in a decrease in DNA synthesis, indicative of a decrease in cellular proliferation. Vascular injury such as that caused during surgery or balloon angioplasty can be treated by administering APEG-1 polypeptides or DNA encoding APEG-1 polypeptides operably linked to appropriate expression control sequences. Other vascular conditions, e.g., atherosclerosis, transplant arteriosclerosis, and diabetes, which are characterized by a decrease in APEG-1 expression (FIG. 15) may be treated in a similar manner. APEG-1 polypeptide, DNA encoding an APEG-1 polypeptide, or compositions which stimulate the APEG-1 promoter may administered to increase the level of APEG-1 polypeptide in the injured vascular tissue and thus inhibit the growth of smooth muscle cells.

APEG-1 polypeptides may be administered to the patient intravenously in a pharmaceutically acceptable carrier such as physiological saline. Standard methods for intracellular delivery of peptides can be used, e.g. packaged in liposomes. Such methods are well known to those of ordinary skill in the art. It is expected that an intravenous dosage of approximately 1 to 100 μmoles of the polypeptide of the invention would be administered per kg of body weight per day. The compositions of the invention are useful for parenteral administration, such as intravenous, subcutaneous, intramuscular, and intraperitoneal.

Compounds which increase APEG-1 expression, e.g., by inhibiting binding of a trans-acting repressor to a cis-acting repressor sequence (e.g. SEQ ID NO:24) are administered as described above.

DNA (e.g., APEG-1-encoding DNA, DNA including vascular cell-specific promoters (e.g., sequences which hybridize at high stringency to SEQ ID NO:17, SEQ ID NO:20, or SEQ ID NO:23), SPEG-encoding DNA, and striated muscle cell-specific promoters) and vectors of the invention may be introduced into target cells of the patient by standard vectors and/or gene delivery systems. Suitable gene delivery systems may include liposomes, receptor-mediated delivery systems, naked DNA, and viral vectors such as herpes viruses, retroviruses, and adenoviruses, among others. For example, the DNA under encoding an APEG-1 or SPEG polypeptide under the control of a strong constitutive promoter may be administered locally to a blood vessel during balloon angioplasty using an adenovirus delivery system.

A vascular cell-specific promoter or enhancer sequence derived from the APEG-1 gene (e.g., SEQ ID NO:17, SEQ ID NO:20 or SEQ ID NO:23) may be used to direct the expression of APEG-1 or genes other than APEG-1. Thus, vascular diseases may be treated by administering a vascular cell-specific enhancer sequence of the invention operably linked to a sequence encoding a heterologous polypeptide, e.g., an APEG-1 promoter linked to DNA encoding a growth inhibitor gene such as Rb, p21 or p18.

The DNA may encode a naturally occurring mammalian APEG-1 polypeptide such as a rat APEG-1 polypeptide (SEQ ID NO:3) or human APEG-1 polypeptide (SEQ ID NO:12). For example, the invention includes degenerate variants of SEQ ID NO:2 or SEQ ID NO:11. The invention also includes a substantially pure DNA comprising a strand which hybridizes at high stringency to a DNA having the sequence of SEQ ID NO:1, 2, or 11, or the complements thereof.

Similarly, a striated muscle cell specific-promoter may be used to direct expression of SPEG or genes other than SPEG. Thus, striated muscle diseases may be treated by administering a striated muscle cell-specific promoter of the invention operably linked to a sequence encoding a heterologous polypeptide, e.g., a SPEG promoter linked to DNA encoding a therapeutic gene, e.g., dystrophin to treat Duchenne's or Becker's muscular dystrophy, or a growth inhibitor gene such as Rb, p21, or p18, to reduce undesirable proliferation of striated muscle cells.

The DNA of the invention may be administered in a pharmaceutically acceptable carrier. The therapeutic composition may also include a gene delivery system as described above. Pharmaceutically acceptable carriers are biologically compatible vehicles which are suitable for administration to an animal e.g., physiological saline. A therapeutically effective amount is an amount of the nucleic acid of the invention which is capable of producing a medically desirable result in a treated animal.

As is well known in the medical arts, dosage for any given patient depends upon many factors, including the patient's size, body surface area, age, the particular compound to be administered, sex, time and route of administration, general health, and other drugs being administered concurrently. Dosages for the compounds of the invention will vary, but a preferred dosage for intravenous administration is from approximately $10^6$ to $10^{22}$ copies of the nucleic acid molecule. Determination of optimal dosage is well within the abilities of a pharmacologist of ordinary skill.

Drugs which stimulate the APEG-1 promoter may also be administered as described above to increase the level of expression APEG-1 in vascular tissue. Such drugs can be identified by contacting the APEG-1 promoter linked to a reporter gene with a candidate compound and measuring the level of expression of the reporter gene in the presence and absence of the compound. An increased level of expression in the presence of the compound compared to that in its absence indicates that the compound stimulates the APEG-1 promoter.

The invention also includes cells transfected with the DNA of the invention. Standard methods for transfecting cells with isolated nucleic acid are well known to those skilled in the art of molecular biology. Preferably, the cells are vascular smooth muscle cells, and they express an APEG-1 polypeptide of the invention encoded by the nucleic acid of the invention. Cells of the invention may be administered to an animal locally or systemically using intravenous, subcutaneous, intramuscular, and intraperitoneal delivery methods. Alternatively, prokaryotic or eukaryotic cells in culture can be transfected with the DNA of the invention operably linked to expression control sequences appropriate for high-level expression in the cell. Such cells are useful for producing large amounts of the APEG-1 polypeptide, which can be purified and used, e.g., as a therapeutic or for raising anti-APEG-1 antibodies.

Methods of Evaluating Compounds for Binding to the VSMC Transcriptional Repressor Sequence The invention includes methods of evaluating a compound for the ability to bind to a vascular smooth muscle cell cis-acting transcriptional repressor sequence. The cis-acting sequence can include a sequence which hybridizes under high stringency conditions to SEQ ID NO:24, e.g., a sequence containing SEQ ID NO:24 itself.

The compound can be contacted with a vascular smooth muscle cell cis-acting transcriptional repressor sequence using methods known in the art and the amount of binding determined using methods known in the art. For example, altered gel mobility assays can be used to ascertain binding of a test compound to the cis-acting transcriptional repressor sequence. Alternatively, assays that detect altered sensitivity to agents such as DNase or dimethyl sulfate (DMS) in the presence of the test compound can be used.

Alternatively, a compound can be evaluated for its ability to bind to a cis-acting transcriptional repressor sequence by providing a vascular smooth muscle cell containing a nucleic acid comprising a vascular smooth muscle cell cis-acting transcriptional repressor sequence which is operably linked to a sequence encoding a reporter molecule. The reporter molecule can be, e.g., luciferase or β-galactosidase.

The test compound is then added to the cell, and the amount of the reporter molecule expressed by the cell is measured. An alteration in the level of reporter molecule expressed in the presence of the compound compared to the level in the absence of the compound indicates that the compound binds to a vascular smooth muscle cell cis-acting transcriptional repressor sequence.

For example, an increase in the level of transcription of DNA encoding the reporter molecule, or an increase in the amount of molecule expressed, indicates that the test compound inhibits binding of a trans-acting repressor factor in a VSMC to the cis-acting sequence and therefore functions therapeutically to increase expression of APEG-1 and decrease VSMC proliferation.

Other embodiments are within the following claims.

What is claimed is:

1. A substantially pure DNA comprising a vascular smooth muscle cell (VSMC) specific enhancer sequence operably linked to a polypeptide coding sequence, wherein said enhancer sequence includes a sequence which hybridizes under high stringency conditions to SEQ ID NO:20, or the complement thereof, and wherein said DNA does not contain the complete nucleotide sequence of SEQ ID NO:17.

2. The DNA of claim 1, wherein the DNA sequence contains less than 2.6 kb of SEQ ID NO:17.

3. The DNA of claim 1, wherein the DNA sequence contains less than 2.1 kb of SEQ ID NO:17.

4. The DNA of claim 1, wherein the DNA sequence contains less than 1.7 kb of SEQ ID NO:17.

5. The DNA of claim 1, wherein the enhancer sequence is less than 100 nucleotides in length.

6. The DNA of claim 1, wherein the enhancer sequence is less than 50 nucleotides in length.

7. The DNA of claim 1, wherein the enhancer sequence comprises SEQ ID NO:20.

8. The DNA of claim 1, wherein the enhancer sequence comprises a plurality of copies of SEQ ID NO:20.

9. The DNA of claim 1, wherein the enhancer sequence hybridizes under high stringency conditions to SEQ ID NO:23, or the complement thereof.

10. The DNA of claim 1, wherein the enhancer sequence comprises SEQ ID NO:23.

11. The DNA of claim 1, wherein the enhancer sequence comprises a plurality of copies of SEQ ID NO:23.

12. The DNA of claim 1, wherein said polypeptide coding sequence does not encode APEG-1.

13. The DNA of claim 1, wherein the enhancer is operably linked to a heterologous promoter.

14. The DNA of claim 1, wherein the polypeptide is chosen from a group consisting of tissue plasminogen activator, p21 cell cycle inhibitor, nitric oxide synthase, interferon-γ, and atrial natriuretic polypeptide.

15. A vector comprising the DNA of claim 1.

16. A method of directing vascular smooth muscle cell-specific expression of a polypeptide, comprising introducing into a vascular smooth muscle cell the vector of claim 15.

* * * * *

SEQUENCE LISTING

```
<160> NUMBER OF SEQ ID NOS: 24

<210> SEQ ID NO 1
<211> LENGTH: 1308
<212> TYPE: DNA
<213> ORGANISM: Rattus rattus
<220> FEATURE:
<221> NAME/KEY: CDS
<222> LOCATION: (170)...(508)

<400> SEQUENCE: 1
gaattcggca cgagcagaga cttaaggaag gtgcagacgg ggtccgtttg cacagcctca      60
gggcgcgtcc acatccccct tcagcagccc aatcacctct gatgaggagt acctgagccc     120
cccagaggag ttcccagaac ctggggagac ctggtcccga acccctacc atg aag ccc     178
                                                        Met Lys Pro
                                                          1 agt ccc agc cag gat cga gat tcc tct gac tct tcc tcc aag gca ccc       226
Ser Pro Ser Gln Asp Arg Asp Ser Ser Asp Ser Ser Ser Lys Ala Pro
      5                  10                  15 cca acc ttc aag gtc tca ctc atg gac caa tca gtg aga gaa ggt caa       274
Pro Thr Phe Lys Val Ser Leu Met Asp Gln Ser Val Arg Glu Gly Gln
 20                  25                  30                  35 gat gtc att atg agc atc cgc gtg cag ggg gag ccc aag cct gtg gtc       322
Asp Val Ile Met Ser Ile Arg Val Gln Gly Glu Pro Lys Pro Val Val
                 40                  45                  50 tcc tgg ctg agg aat cgg cag cct gtg cgc cca gac cag cgg cgc ttt       370
Ser Trp Leu Arg Asn Arg Gln Pro Val Arg Pro Asp Gln Arg Arg Phe
         55                  60                  65 gca gag gag gcc gag ggt ggg ctc tgc cgg ttg agg atc ctg gct gct       418
Ala Glu Glu Ala Glu Gly Gly Leu Cys Arg Leu Arg Ile Leu Ala Ala
     70                  75                  80 gag agg gga gat gct ggt ttc tac act tgc aag gcg gtc aac gaa tat       466
Glu Arg Gly Asp Ala Gly Phe Tyr Thr Cys Lys Ala Val Asn Glu Tyr
 85                  90                  95
```

-continued

```
ggc gct cgg cag tgt gag gcc cgc ctg gag gtc cga ggc gag        508
Gly Ala Arg Gln Cys Glu Ala Arg Leu Glu Val Arg Gly Glu
100                 105                 110 tgagctcagg gggccacctg cgctgccccc gctaccctcc gagctgcacc cctgtctcag   568
gcacctcctg gacctcgctg tgtttcactg cctcctgccc acagaccag ccggctcgcc    628
ggcccggaca tagcccatgc tccccttccc tccctagccc atacagcacc ctggggtaac   688
ccatcgggcc cctgtggatc ctccctcccc aagtggatat gtggctgtgc agaccaggag   748
gcccccagaa ggactgagtg ttgagaaggg atggccatga ggttgtgaca agctccccc    808
gtccccagcc tccatgtagg gagcatccag cgaatgcatg tgctatgctg ctacaggcca   868
ctgtctgtct ctctgtctgt ctgcctgtgt gtctgtgaca gtcagggaag aaaaccttcg   928
agctgaggtg ggataagaca gaataagatg atagaacaca gcatctgtga gatgcagggg   988
cccagagggg caggcacagt ggataggaga ctctctggga agggtagggc actgaccatt  1048
gcagaaatgg gttttaaatg gcacaacatt ttttattcca catgagacca aaagctagag  1108
gtctgggatt aagccctgac tgctggcaag cttaggacca agtggggtac ccttcttcac  1168
agacacatcc gacacgctct gtctgggaat gagagagtag ccagactgag cacaggagca  1228
ggtcatagtg ggactggagg tttggaaaca ctatttcgta gctcaaataa agtccagttt  1288
gtacccaaaa aaaaaaaaaa                                              1308
```

<210> SEQ ID NO 2
<211> LENGTH: 342
<212> TYPE: DNA
<213> ORGANISM: Rattus rattus

<400> SEQUENCE: 2

```
atgaagccca gtcccagcca ggatcgagat tcctctgact cttcctccaa ggcaccccca    60
accttcaagg tctcactcat ggaccaatca gtgagagaag gtcaagatgt cattatgagc   120
atccgcgtgc aggggagcc caagcctgtg gtctcctggc tgaggaatcg gcagcctgtg   180
cgcccagacc agcggcgctt tgcagaggag gccgaggtg ggctctgccg gttgaggatc    240
ctggctgctg agaggggaga tgctggtttc tacacttgca aggcggtcaa cgaatatggc   300
gctcggcagt gtgaggcccg cctggaggtc cgaggcgagt ga                      342
```

<210> SEQ ID NO 3
<211> LENGTH: 113
<212> TYPE: PRT
<213> ORGANISM: Rattus rattus

<400> SEQUENCE: 3

```
Met Lys Pro Ser Pro Ser Gln Asp Arg Asp Ser Ser Asp Ser Ser
1               5                   10                  15

Lys Ala Pro Pro Thr Phe Lys Val Ser Leu Met Asp Gln Ser Val Arg
                20                  25                  30

Glu Gly Gln Asp Val Ile Met Ser Ile Arg Val Gln Gly Glu Pro Lys
            35                  40                  45

Pro Val Val Ser Trp Leu Arg Asn Arg Gln Pro Val Arg Pro Asp Gln
        50                  55                  60

Arg Arg Phe Ala Glu Glu Ala Glu Gly Gly Leu Cys Arg Leu Arg Ile
65                  70                  75                  80

Leu Ala Ala Glu Arg Gly Asp Ala Gly Phe Tyr Thr Cys Lys Ala Val
                85                  90                  95

Asn Glu Tyr Gly Ala Arg Gln Cys Glu Ala Arg Leu Glu Val Arg Gly
```

-continued

```
                      100                 105                 110
Glu

<210> SEQ ID NO 4
<211> LENGTH: 113
<212> TYPE: PRT
<213> ORGANISM: Gallus gallus

<400> SEQUENCE: 4

Met Lys Pro Ser Pro Ser Gln Asp Arg Asp Ser Ser Asp Ser Ser
  1               5                  10                  15

Lys Ala Pro Pro Thr Phe Lys Val Ser Leu Met Asp Gln Ser Val Arg
                 20                  25                  30

Glu Gly Gln Asp Val Ile Met Ser Ile Arg Val Gln Gly Glu Pro Lys
             35                  40                  45

Pro Val Val Ser Trp Leu Arg Asn Arg Gln Pro Val Arg Pro Asp Gln
         50                  55                  60

Arg Arg Phe Ala Glu Glu Ala Glu Gly Gly Leu Cys Arg Leu Arg Ile
 65                  70                  75                  80

Leu Ala Ala Glu Arg Gly Asp Ala Gly Phe Tyr Thr Cys Lys Ala Val
                 85                  90                  95

Asn Glu Tyr Gly Ala Arg Gln Cys Glu Ala Arg Leu Glu Val Arg Gly
                100                 105                 110

Glu

<210> SEQ ID NO 5
<211> LENGTH: 157
<212> TYPE: PRT
<213> ORGANISM: Gallus gallus

<400> SEQUENCE: 5

Met Ala Met Ile Ser Gly Met Ser Gly Arg Lys Ala Ser Gly Ser Ser
  1               5                  10                  15

Pro Thr Ser Pro Ile Asn Ala Asp Lys Val Glu Asn Glu Asp Ala Phe
                 20                  25                  30

Leu Glu Glu Val Ala Glu Glu Lys Pro His Val Lys Pro Tyr Phe Thr
             35                  40                  45

Lys Thr Ile Leu Asp Met Glu Val Val Glu Gly Ser Ala Ala Arg Phe
         50                  55                  60

Asp Cys Lys Ile Glu Gly Tyr Pro Asp Pro Glu Val Met Trp Tyr Lys
 65                  70                  75                  80

Asp Asp Gln Pro Val Lys Glu Ser Arg His Phe Gln Ile Asp Tyr Asp
                 85                  90                  95

Glu Glu Gly Asn Cys Ser Leu Thr Ile Ser Glu Val Cys Gly Asp Asp
                100                 105                 110

Asp Ala Lys Tyr Thr Cys Lys Ala Val Asn Ser Leu Gly Glu Ala Thr
                115                 120                 125

Cys Thr Ala Glu Leu Leu Val Glu Thr Met Gly Lys Glu Gly Glu Gly
            130                 135                 140

Glu Gly Glu Gly Glu Glu Asp Glu Glu Glu Glu Glu
145                 150                 155

<210> SEQ ID NO 6
<211> LENGTH: 155
<212> TYPE: PRT
<213> ORGANISM: Leporidae
```

-continued

```
<400> SEQUENCE: 6

Met Ala Met Ile Ser Gly Leu Ser Gly Arg Lys Ser Thr Gly Ser
1               5                   10                  15

Pro Thr Ser Pro Leu Thr Ala Glu Arg Leu Glu Thr Glu Glu Asp Val
            20                  25                  30

Ser Gln Ala Phe Leu Glu Ala Val Ala Glu Glu Lys Pro His Val Lys
        35                  40                  45

Pro Tyr Phe Ser Lys Thr Ile Arg Asp Leu Glu Val Val Glu Gly Ser
    50                  55                  60

Ala Ala Arg Phe Asp Cys Lys Ile Glu Gly Tyr Pro Asp Pro Glu Val
65                  70                  75                  80

Val Trp Phe Lys Asp Asp Gln Ser Ile Arg Glu Ser Arg His Phe Gln
                85                  90                  95

Ile Asp Tyr Asp Glu Asp Gly Asn Cys Ser Leu Ile Ile Ser Asp Val
            100                 105                 110

Cys Gly Asp Asp Asp Ala Lys Tyr Thr Cys Lys Ala Val Asn Ser Leu
        115                 120                 125

Gly Glu Ala Thr Cys Thr Ala Glu Leu Ile Val Glu Thr Met Glu Glu
    130                 135                 140

Gly Glu Gly Glu Gly Glu Glu Glu Glu Glu
145                 150                 155

<210> SEQ ID NO 7
<211> LENGTH: 155
<212> TYPE: PRT
<213> ORGANISM: Leporidae

<400> SEQUENCE: 7

Met Ala Met Ile Ser Gly Leu Ser Gly Arg Lys Ser Thr Gly Ser
1               5                   10                  15

Pro Thr Ser Pro Leu Thr Ala Glu Arg Leu Glu Thr Glu Glu Asp Val
            20                  25                  30

Ser Gln Ala Phe Leu Glu Ala Val Ala Glu Glu Lys Pro His Val Lys
        35                  40                  45

Pro Tyr Phe Ser Lys Thr Ile Arg Asp Leu Glu Val Val Glu Gly Ser
    50                  55                  60

Ala Ala Arg Phe Asp Cys Lys Ile Glu Gly Tyr Pro Asp Pro Glu Val
65                  70                  75                  80

Val Trp Phe Lys Asp Asp Gln Ser Ile Arg Glu Ser Arg His Phe Gln
                85                  90                  95

Ile Asp Tyr Asp Glu Asp Gly Asn Cys Ser Leu Ile Ile Ser Asp Val
            100                 105                 110

Cys Gly Asp Asp Asp Ala Lys Tyr Thr Cys Lys Ala Val Asn Ser Leu
        115                 120                 125

Gly Glu Ala Thr Cys Thr Ala Glu Leu Ile Val Glu Thr Met Glu Glu
    130                 135                 140

Gly Glu Gly Glu Gly Glu Glu Glu Glu Glu
145                 150                 155

<210> SEQ ID NO 8
<211> LENGTH: 113
<212> TYPE: PRT
<213> ORGANISM: Rattus rattus

<400> SEQUENCE: 8

Met Lys Pro Ser Pro Ser Gln Asp Arg Asp Ser Ser Asp Ser Ser Ser
```

-continued

```
                1               5              10              15
Lys Ala Pro Pro Thr Phe Lys Val Ser Leu Met Asp Gln Ser Val Arg
                       20                  25                  30

Glu Gly Gln Asp Val Ile Met Ser Ile Arg Val Gln Gly Glu Pro Lys
            35                  40                  45

Pro Val Val Ser Trp Leu Arg Asn Arg Gln Pro Val Arg Pro Asp Gln
        50                  55                  60

Arg Arg Phe Ala Glu Glu Ala Glu Gly Gly Leu Cys Arg Leu Arg Ile
65                  70                  75                  80

Leu Ala Ala Glu Arg Gly Asp Ala Gly Phe Tyr Thr Cys Lys Ala Val
                    85                  90                  95

Asn Glu Tyr Gly Ala Arg Gln Cys Glu Ala Arg Leu Val Arg Gly
                100                 105                 110

Glu
```

<210> SEQ ID NO 9
<211> LENGTH: 35
<212> TYPE: PRT
<213> ORGANISM: Artificial Sequence
<220> FEATURE:
<223> OTHER INFORMATION: synthetic consensus sequence

<400> SEQUENCE: 9

```
Ser Arg Ser Ser Pro Pro Phe Asp Val Glu Gly Gly Pro Pro Val Trp
1               5              10              15

Gln Glu Gly Cys Leu Ile Asp Tyr Thr Cys Lys Ala Val Asn Gly Cys
                20                  25                  30

Ala Leu Val
        35
```

<210> SEQ ID NO 10
<211> LENGTH: 14
<212> TYPE: DNA
<213> ORGANISM: Artificial Sequence
<220> FEATURE:
<223> OTHER INFORMATION: synthetic poly T anchoring primer

<400> SEQUENCE: 10
tttttttttt ttvg                                                        14

<210> SEQ ID NO 11
<211> LENGTH: 1238
<212> TYPE: DNA
<213> ORGANISM: Homo sapiens
<220> FEATURE:
<221> NAME/KEY: CDS
<222> LOCATION: (88)...(426)
<221> NAME/KEY: misc_feature
<222> LOCATION: (1)...(1238)
<223> OTHER INFORMATION: n = A,T,C or G

<400> SEQUENCE: 11

```
tcacctctga tgaggaatac ctgagccccc cagaggagtt cccagagcct ggggagacct      60 gggagacct ggccgcgaac ccccacc atg aag ccc agt ccc agc cag gac cgc     114
                              Met Lys Pro Ser Pro Ser Gln Asp Arg
                                1               5 cgt tct tct gac act ggc tcc aag gca ccc ccc acc ttc aag gtc tca      162
Arg Ser Ser Asp Thr Gly Ser Lys Ala Pro Pro Thr Phe Lys Val Ser
 10              15                  20                  25 ctt atg gac cag tca gta aga gaa ggc caa gat gtc atc atg agc atc      210
Leu Met Asp Gln Ser Val Arg Glu Gly Gln Asp Val Ile Met Ser Ile
```

```
                30              35              40
cgc gtg cag ggg gag ccc aag cct gtg gtc tcc tgg ctg aga aac cgc    258
Arg Val Gln Gly Glu Pro Lys Pro Val Val Ser Trp Leu Arg Asn Arg
             45              50              55 cag ccc gtg cgc cca gac cag cgg cgc ttt gcg gag gag gct gag ggt    306
Gln Pro Val Arg Pro Asp Gln Arg Arg Phe Ala Glu Glu Ala Glu Gly
         60              65              70 ggg ctg tgc cgg ctg cgg atc ctg gct gca gag cgt ggc gat gct ggt    354
Gly Leu Cys Arg Leu Arg Ile Leu Ala Ala Glu Arg Gly Asp Ala Gly
     75              80              85 ttc tac act tgc aaa gcg gtc aat gag tat ggt gct cgg cag tgc gag    402
Phe Tyr Thr Cys Lys Ala Val Asn Glu Tyr Gly Ala Arg Gln Cys Glu
 90              95             100             105 gcc cgc ttg gag gtc cga ggc gag tgagctcagg gggccacctg cgctccccc    456
Ala Arg Leu Glu Val Arg Gly Glu
                110 gctaccctcc gagccgcgcc cctgtctcag gcacctctcg gacctcgctg tgtttcactg   516 cctcctgccc acagacccag gcctgccggc ccggacccgt cccagcctcc cctccccacc   576 ccatgcagcc cccaggggga tagcccatgg gcccctgtgg acactccctc cccaagtgga   636 cacatggctg tgcaggccag gaggcccaca gatggactga gtgctgggaa ggggcggctt   696 cgagggtat caacccccg agtctctccc tgaagggag caccgggcga gtgcatgtgc      756 tactgctgct acaggcctgt ctatctgttt gtctgtctgt gtgtctgtga cagtcaggga   816 aggatgcctc ggagctgagg tggggtgaga cagagtggga gagattacgg catggcatgg   876 aggggcccaa ggagcagggg ctgttgacaa aggccttacc aggaagggtt aggacactga   936 ccattctaga aatgggtttc gaatggcaca acactttcta tttcacaaaa gaccaaaagc   996 cagaggcccc aggctctgtg ctgatgaaca gcctggctga gccctggccc tggcaggttt  1056 agggcccatt tgggcccccc tccttctctg tcagggctgg ggtgctctgt ctgggaatga  1116 gggagttaac caagtttggt gcaggagcag gggcagggg ccactgtagt gagcgtggat   1176 gaaatttgga nacacctatn tcttaantca aataaagtcc agtttgtacc taaaaaaaaa  1236 aa                                                                 1238

<210> SEQ ID NO 12
<211> LENGTH: 113
<212> TYPE: PRT
<213> ORGANISM: Homo sapiens

<400> SEQUENCE: 12

Met Lys Pro Ser Pro Ser Gln Asp Arg Arg Ser Ser Asp Thr Gly Ser
 1               5                  10                  15

Lys Ala Pro Pro Thr Phe Lys Val Ser Leu Met Asp Gln Ser Val Arg
                20                  25                  30

Glu Gly Gln Asp Val Ile Met Ser Ile Arg Val Gln Gly Glu Pro Lys
             35                  40                  45

Pro Val Val Ser Trp Leu Arg Asn Arg Gln Pro Val Arg Pro Asp Gln
         50                  55                  60

Arg Arg Phe Ala Glu Glu Ala Glu Gly Gly Leu Cys Arg Leu Arg Ile
 65                  70                  75                  80

Leu Ala Ala Glu Arg Gly Asp Ala Gly Phe Tyr Thr Cys Lys Ala Val
                 85                  90                  95

Asn Glu Tyr Gly Ala Arg Gln Cys Glu Ala Arg Leu Glu Val Arg Gly
                100                 105                 110
```

Glu

<210> SEQ ID NO 13
<211> LENGTH: 2793
<212> TYPE: DNA
<213> ORGANISM: Homo sapiens
<220> FEATURE:
<221> NAME/KEY: CDS
<222> LOCATION: (3)...(1985)

<400> SEQUENCE: 13

| | | | | | | | | | | | | | | | | |
|---|---|---|---|---|---|---|---|---|---|---|---|---|---|---|---|---|
| ga att | ccg | gtc | caa | atc | cgc | gct | gct | ccc | ccc | acc | gtc | ccc | tcg | ggt | | 47 |
| Ile | Pro | Val | Gln | Ile | Arg | Ala | Ala | Pro | Pro | Thr | Val | Pro | Ser | Gly | | |
| | 1 | | | 5 | | | | | 10 | | | | | 15 | | |
| cgg | gaa | gcg | gtc | ccc | gcc | ggg | acc | ccc | ggc | cca | gcc | cgc | ggc | cac | ccc | 95 |
| Arg | Glu | Ala | Val | Pro | Ala | Gly | Thr | Pro | Gly | Pro | Ala | Arg | Gly | His | Pro | |
| | | | 20 | | | | | 25 | | | | | 30 | | | |
| cac | gtc | gcc | cca | ccg | tcg | cac | tca | gga | gcc | tgt | gct | gcc | cga | gga | cac | 143 |
| His | Val | Ala | Pro | Pro | Ser | His | Ser | Gly | Ala | Cys | Ala | Ala | Arg | Gly | His | |
| | | 35 | | | | | 40 | | | | | 45 | | | | |
| cac | cac | cga | aga | gaa | gcg | agg | gaa | gaa | gtc | caa | gtc | gtc | cgg | gcc | ctc | 191 |
| His | His | Arg | Arg | Glu | Ala | Arg | Glu | Glu | Val | Gln | Val | Val | Arg | Ala | Leu | |
| | 50 | | | | | 55 | | | | | 60 | | | | | |
| cct | ggc | ggg | cac | cgg | gaa | tcc | cga | ccc | cag | acg | cca | ctg | agc | gag | gcc | 239 |
| Pro | Gly | Gly | His | Arg | Glu | Ser | Arg | Pro | Gln | Thr | Pro | Leu | Ser | Glu | Ala | |
| 65 | | | | | 70 | | | | | 75 | | | | | | |
| tca | ggc | cgc | ctg | tgg | gcg | ttg | ggc | cga | tcg | cct | agg | ctg | gtg | cgc | gcc | 287 |
| Ser | Gly | Arg | Leu | Trp | Ala | Leu | Gly | Arg | Ser | Pro | Arg | Leu | Val | Arg | Ala | |
| 80 | | | | | 85 | | | | | 90 | | | | | 95 | |
| ggc | tcc | cgc | atc | ctg | gac | aag | ctg | cag | ttc | ttc | gag | gag | cga | cgg | cgc | 335 |
| Gly | Ser | Arg | Ile | Leu | Asp | Lys | Leu | Gln | Phe | Phe | Glu | Glu | Arg | Arg | Arg | |
| | | | 100 | | | | | 105 | | | | | 110 | | | |
| agc | ctg | gag | cgc | agc | gac | tcg | ccg | ccg | gcg | ccc | ctg | cgg | ccc | tgg | gtg | 383 |
| Ser | Leu | Glu | Arg | Ser | Asp | Ser | Pro | Pro | Ala | Pro | Leu | Arg | Pro | Trp | Val | |
| | | 115 | | | | | 120 | | | | | 125 | | | | |
| ccc | ctg | cgc | aag | gcc | cgc | tct | ctg | gag | cag | ccc | aag | tcg | gag | cgc | ggc | 431 |
| Pro | Leu | Arg | Lys | Ala | Arg | Ser | Leu | Glu | Gln | Pro | Lys | Ser | Glu | Arg | Gly | |
| | 130 | | | | | 135 | | | | | 140 | | | | | |
| gca | ccg | tgg | ggc | acc | ccc | ggg | gcc | tcg | cag | gaa | gaa | ctg | cgg | gcg | cca | 479 |
| Ala | Pro | Trp | Gly | Thr | Pro | Gly | Ala | Ser | Gln | Glu | Glu | Leu | Arg | Ala | Pro | |
| 145 | | | | | 150 | | | | | 155 | | | | | | |
| ggc | agc | gtg | gcc | gag | cgg | cgc | cgc | ctg | ttc | cag | cag | aaa | gcg | gcc | tcg | 527 |
| Gly | Ser | Val | Ala | Glu | Arg | Arg | Arg | Leu | Phe | Gln | Gln | Lys | Ala | Ala | Ser | |
| 160 | | | | | 165 | | | | | 170 | | | | | 175 | |
| ctg | gac | gag | cgc | acg | cgt | cag | cgc | agc | ccg | gcc | tca | gac | ctc | gag | ctg | 575 |
| Leu | Asp | Glu | Arg | Thr | Arg | Gln | Arg | Ser | Pro | Ala | Ser | Asp | Leu | Glu | Leu | |
| | | | 180 | | | | | 185 | | | | | 190 | | | |
| cgc | ttc | gcc | cag | gag | ctg | ggc | cgc | atc | cgc | cgc | tcc | acg | tcg | cgg | gag | 623 |
| Arg | Phe | Ala | Gln | Glu | Leu | Gly | Arg | Ile | Arg | Arg | Ser | Thr | Ser | Arg | Glu | |
| | | 195 | | | | | 200 | | | | | 205 | | | | |
| gag | ctg | gtg | cgc | tcg | cac | gag | tcc | ctg | cgc | gcc | acg | ctg | cag | cgt | gcc | 671 |
| Glu | Leu | Val | Arg | Ser | His | Glu | Ser | Leu | Arg | Ala | Thr | Leu | Gln | Arg | Ala | |
| | 210 | | | | | 215 | | | | | 220 | | | | | |
| cca | tcc | cct | cga | gag | ccc | ggc | gag | ccc | ccg | ctc | ttc | tct | cgg | ccc | tcc | 719 |
| Pro | Ser | Pro | Arg | Glu | Pro | Gly | Glu | Pro | Pro | Leu | Phe | Ser | Arg | Pro | Ser | |
| 225 | | | | | 230 | | | | | 235 | | | | | | |
| acc | ccc | aag | aca | tcg | cgg | gcc | gtg | agc | ccc | gcc | gcc | gcc | cag | ccg | ccc | 767 |
| Thr | Pro | Lys | Thr | Ser | Arg | Ala | Val | Ser | Pro | Ala | Ala | Ala | Gln | Pro | Pro | |
| 240 | | | | 245 | | | | | 250 | | | | | 255 | | |
| tct | ccg | agc | agc | gcg | gag | aag | ccg | ggg | gac | gag | cct | ggg | agg | ccc | agg | 815 |
| Ser | Pro | Ser | Ser | Ala | Glu | Lys | Pro | Gly | Asp | Glu | Pro | Gly | Arg | Pro | Arg | |

```
            260                 265                 270
agc cgc ggg ccg gcg ggc agg aca gag ccg ggg gaa ggc ccg cag cag    863
Ser Arg Gly Pro Ala Gly Arg Thr Glu Pro Gly Glu Gly Pro Gln Gln
            275                 280                 285 gag gtt agg cgt cgg gac caa ttc ccg ctg acc cgg agc aga gcc atc    911
Glu Val Arg Arg Arg Asp Gln Phe Pro Leu Thr Arg Ser Arg Ala Ile
            290                 295                 300 cag gag tgc agg agc cct gtg ccg ccc ccc gcc gcc gat ccc cca gag    959
Gln Glu Cys Arg Ser Pro Val Pro Pro Pro Ala Ala Asp Pro Pro Glu
    305                 310                 315 gcc agg acg aaa gca ccc ccc ggt cgg aag cgg gag ccc ccg gcg cag   1007
Ala Arg Thr Lys Ala Pro Pro Gly Arg Lys Arg Glu Pro Pro Ala Gln
320                 325                 330                 335 gcc gtg cgc ttc ctg ccc tgg gcc acg ccg ggc ctg gag ggc gct gct   1055
Ala Val Arg Phe Leu Pro Trp Ala Thr Pro Gly Leu Glu Gly Ala Ala
                340                 345                 350 gta ccc cag acc ttg gag aag aac agg gcg ggg cct gag gca gag aag   1103
Val Pro Gln Thr Leu Glu Lys Asn Arg Ala Gly Pro Glu Ala Glu Lys
            355                 360                 365 agg ctt cgc aga ggg ccg gag gag gac ggt ccc tgg ggg ccc tgg gac   1151
Arg Leu Arg Arg Gly Pro Glu Glu Asp Gly Pro Trp Gly Pro Trp Asp
            370                 375                 380 cgc cga ggg gcc cgc agc cag ggc aaa ggt cgc ggg gcc cgg ccc acc   1199
Arg Arg Gly Ala Arg Ser Gln Gly Lys Gly Arg Arg Ala Arg Pro Thr
385                 390                 395 tcc cct gag ctc gag tct tcg gat gac tcc tac gtg tcc gct gga gaa   1247
Ser Pro Glu Leu Glu Ser Ser Asp Asp Ser Tyr Val Ser Ala Gly Glu
400                 405                 410                 415 gag ccc cta gag gcc cct gtg ttt gag atc ccc ctg cag aat gtg gtg   1295
Glu Pro Leu Glu Ala Pro Val Phe Glu Ile Pro Leu Gln Asn Val Val
                420                 425                 430 gtg gca cca ggg gca gat gtg ctc ctc aaa tgt atc atc act gcc aac   1343
Val Ala Pro Gly Ala Asp Val Leu Leu Lys Cys Ile Ile Thr Ala Asn
            435                 440                 445 ccc ccg ccc caa gtg tcc tgg cac aag gat ggg tca gcg ctg cgc agc   1391
Pro Pro Pro Gln Val Ser Trp His Lys Asp Gly Ser Ala Leu Arg Ser
            450                 455                 460 gag ggc cgc ctc ctc ctc cgg gct gag ggt gag cgg cac acc ctg ctg   1439
Glu Gly Arg Leu Leu Leu Arg Ala Glu Gly Glu Arg His Thr Leu Leu
465                 470                 475 ctc agg gag gcc agg gca gca gat gcc ggg agc tat atg gcc acc gcc   1487
Leu Arg Glu Ala Arg Ala Ala Asp Ala Gly Ser Tyr Met Ala Thr Ala
480                 485                 490                 495 acc aac gag ctg ggc cag gcc acc tgt gcc gcc tca ctg acc gtg aga   1535
Thr Asn Glu Leu Gly Gln Ala Thr Cys Ala Ala Ser Leu Thr Val Arg
                500                 505                 510 ccc ggt ggg tct aca tcc cct ttc agc agc ccc atc acc tcc gac gag   1583
Pro Gly Gly Ser Thr Ser Pro Phe Ser Ser Pro Ile Thr Ser Asp Glu
            515                 520                 525 gaa tac ctg agc ccc cca gag gag ttc cca gag cct ggg gag acc tgg   1631
Glu Tyr Leu Ser Pro Pro Glu Glu Phe Pro Glu Pro Gly Glu Thr Trp
            530                 535                 540 ccg cga acc ccc acc atg aag ccc agt ccc agc cag aac cgc cgt tct   1679
Pro Arg Thr Pro Thr Met Lys Pro Ser Pro Ser Gln Asn Arg Arg Ser
545                 550                 555 tct gac act ggc tcc aag gca ccc ccc acc ttc aag gtc tca ctt atg   1727
Ser Asp Thr Gly Ser Lys Ala Pro Pro Thr Phe Lys Val Ser Leu Met
560                 565                 570                 575 gac cag tca gta aga gaa ggc caa gat gtc atc atg agc atc cgc gtg   1775
Asp Gln Ser Val Arg Glu Gly Gln Asp Val Ile Met Ser Ile Arg Val
```

-continued

```
                Asp Gln Ser Val Arg Glu Gly Gln Asp Val Ile Met Ser Ile Arg Val
                            580                 585                 590 cag ggg gag ccc aag cct gtg gtc tcc tgg ctg aga aac cgc cag ccc        1823
Gln Gly Glu Pro Lys Pro Val Val Ser Trp Leu Arg Asn Arg Gln Pro
            595                 600                 605 gtg cgc cca gac cag cgg cgc ttt gcg gag gag gct gag ggt ggg ctg        1871
Val Arg Pro Asp Gln Arg Arg Phe Ala Glu Glu Ala Glu Gly Gly Leu
        610                 615                 620 tgc cgg ctg cgg atc ctg gct gca gag cgt ggc gat gct ggt ttc tac        1919
Cys Arg Leu Arg Ile Leu Ala Ala Glu Arg Gly Asp Ala Gly Phe Tyr
    625                 630                 635 act tgc aaa gcg gtc aat gag tat ggt gct cgg cag tgc gag gcc cgc        1967
Thr Cys Lys Ala Val Asn Glu Tyr Gly Ala Arg Gln Cys Glu Ala Arg
640                 645                 650                 655 ttg gag gtc cga ggc gag tgagctcagg gggccacctg cgctccccc               2015
Leu Glu Val Arg Gly Glu
                660 gctaccctcc gagccgcgcc cctgtctcag gcacctctcg gacctcgctg tgtttcactg      2075 cctcctgccc acagacccag ctgccggccc ggacccgtcc cagcctcccc tcccacccc      2135 atgcagcccc caggggata gcccatgggc cctgtggac cctcctccc caagtggaca        2195 catggctgtg cagccaggag gcccacagat ggactgagtg ctgggaaggg gcggctgcga     2255 ggggtatcaa ccccccgagt ctctccctga aggggagcac cgggcgagtg catgtgctac    2315 tgctgctaca ggcctgtcta tctgtttgtc tgtctgtgtg tctgtgacag tcagggaagg     2375 atgcctcgga gctgaggtgg ggtgagacag agtgggagag attacggcat ggcatggagg    2435 ggcccaagga gcaggggctg ttgacaaagg ccttaccagg aagggttagg acactgacca    2495 ttctagaaat gggtttcgaa tggcacaaca ctttctattt cacaaaagac caaaagccag    2555 aggccccagg ctctgtgctg atgaacagcc tggctgagcc ctggccctgg caggtttagg    2615 gcccatttgg ggccccctcc ttctctgtca gggctggggt gctctgtctg ggaatgaggg    2675 agttaaccaa gtttggtgca ggagcagggg caggggggcca ctgtagtgag cgtggagaaa    2735 tttggaaaca cctatttctt aactcaaata aagtccagtt tgtacctaaa aaaaaaa       2793
```

<210> SEQ ID NO 14
<211> LENGTH: 661
<212> TYPE: PRT
<213> ORGANISM: Homo sapiens

<400> SEQUENCE: 14

```
Ile Pro Val Gln Ile Arg Ala Ala Pro Pro Thr Val Pro Ser Gly Arg
  1               5                  10                  15

Glu Ala Val Pro Ala Gly Thr Pro Gly Pro Ala Arg Gly His Pro His
                 20                  25                  30

Val Ala Pro Pro Ser His Ser Gly Ala Cys Ala Ala Arg Gly His His
             35                  40                  45

His Arg Arg Glu Ala Arg Glu Val Gln Val Arg Ala Leu Pro
         50                  55                  60

Gly Gly His Arg Glu Ser Arg Pro Gln Thr Pro Leu Ser Glu Ala Ser
 65                  70                  75                  80

Gly Arg Leu Trp Ala Leu Gly Arg Ser Pro Arg Leu Val Arg Ala Gly
                 85                  90                  95

Ser Arg Ile Leu Asp Lys Leu Gln Phe Phe Glu Glu Arg Arg Ser
            100                 105                 110

Leu Glu Arg Ser Asp Ser Pro Pro Ala Pro Leu Arg Pro Trp Val Pro
```

-continued

```
            115                 120                 125
Leu Arg Lys Ala Arg Ser Leu Glu Gln Pro Lys Ser Glu Arg Gly Ala
    130                 135                 140
Pro Trp Gly Thr Pro Gly Ala Ser Gln Glu Leu Arg Ala Pro Gly
145                 150                 155                 160
Ser Val Ala Glu Arg Arg Leu Phe Gln Gln Lys Ala Ala Ser Leu
                165                 170                 175
Asp Glu Arg Thr Arg Gln Arg Ser Pro Ala Ser Asp Leu Glu Leu Arg
                180                 185                 190
Phe Ala Gln Glu Leu Gly Arg Ile Arg Arg Ser Thr Ser Arg Glu Glu
                195                 200                 205
Leu Val Arg Ser His Glu Ser Leu Arg Ala Thr Leu Gln Arg Ala Pro
    210                 215                 220
Ser Pro Arg Glu Pro Gly Glu Pro Leu Phe Ser Arg Pro Ser Thr
225                 230                 235                 240
Pro Lys Thr Ser Arg Ala Val Ser Pro Ala Ala Gln Pro Pro Ser
                245                 250                 255
Pro Ser Ser Ala Glu Lys Pro Gly Asp Glu Pro Gly Arg Pro Arg Ser
                260                 265                 270
Arg Gly Pro Ala Gly Arg Thr Glu Pro Gly Glu Gly Pro Gln Gln Glu
                275                 280                 285
Val Arg Arg Arg Asp Gln Phe Pro Leu Thr Arg Ser Arg Ala Ile Gln
    290                 295                 300
Glu Cys Arg Ser Pro Val Pro Pro Ala Ala Asp Pro Pro Glu Ala
305                 310                 315                 320
Arg Thr Lys Ala Pro Pro Gly Arg Lys Arg Glu Pro Pro Ala Gln Ala
                325                 330                 335
Val Arg Phe Leu Pro Trp Ala Thr Pro Gly Leu Glu Gly Ala Ala Val
                340                 345                 350
Pro Gln Thr Leu Glu Lys Asn Arg Ala Gly Pro Glu Ala Glu Lys Arg
    355                 360                 365
Leu Arg Arg Gly Pro Glu Glu Asp Gly Pro Trp Gly Pro Trp Asp Arg
    370                 375                 380
Arg Gly Ala Arg Ser Gln Gly Lys Gly Arg Arg Ala Arg Pro Thr Ser
385                 390                 395                 400
Pro Glu Leu Glu Ser Ser Asp Asp Ser Tyr Val Ser Ala Gly Glu Glu
                405                 410                 415
Pro Leu Glu Ala Pro Val Phe Glu Ile Pro Leu Gln Asn Val Val Val
                420                 425                 430
Ala Pro Gly Ala Asp Val Leu Leu Lys Cys Ile Ile Thr Ala Asn Pro
                435                 440                 445
Pro Pro Gln Val Ser Trp His Lys Asp Gly Ser Ala Leu Arg Ser Glu
                450                 455                 460
Gly Arg Leu Leu Leu Arg Ala Glu Gly Glu Arg His Thr Leu Leu Leu
465                 470                 475                 480
Arg Glu Ala Arg Ala Ala Asp Ala Gly Ser Tyr Met Ala Thr Ala Thr
                485                 490                 495
Asn Glu Leu Gly Gln Ala Thr Cys Ala Ala Ser Leu Thr Val Arg Pro
                500                 505                 510
Gly Gly Ser Thr Ser Pro Phe Ser Ser Pro Ile Thr Ser Asp Glu Glu
                515                 520                 525
Tyr Leu Ser Pro Pro Glu Glu Phe Pro Glu Pro Gly Glu Thr Trp Pro
    530                 535                 540
```

```
Arg Thr Pro Thr Met Lys Pro Ser Pro Ser Gln Asn Arg Arg Ser Ser
545                 550                 555                 560

Asp Thr Gly Ser Lys Ala Pro Pro Thr Phe Lys Val Ser Leu Met Asp
                565                 570                 575

Gln Ser Val Arg Glu Gly Gln Asp Val Ile Met Ser Ile Arg Val Gln
            580                 585                 590

Gly Glu Pro Lys Pro Val Val Ser Trp Leu Arg Asn Arg Gln Pro Val
                595                 600                 605

Arg Pro Asp Gln Arg Arg Phe Ala Glu Ala Glu Gly Gly Leu Cys
        610                 615                 620

Arg Leu Arg Ile Leu Ala Ala Glu Arg Gly Asp Ala Gly Phe Tyr Thr
625                 630                 635                 640

Cys Lys Ala Val Asn Glu Tyr Gly Ala Arg Gln Cys Glu Ala Arg Leu
                645                 650                 655

Glu Val Arg Gly Glu
            660

<210> SEQ ID NO 15
<211> LENGTH: 2614
<212> TYPE: DNA
<213> ORGANISM: Mus musculus
<220> FEATURE:
<221> NAME/KEY: CDS
<222> LOCATION: (1)...(1806)

<400> SEQUENCE: 15 gaa ttc cgg ctg gcg ggc aca gtg gag tcc cgg ccc cag acg cca ctg      48
Glu Phe Arg Leu Ala Gly Thr Val Glu Ser Arg Pro Gln Thr Pro Leu
1               5                   10                  15 agc gag gct tcg ggt cgc ctg tca gca ctg ggc cgc tcg ccc cgg ctg      96
Ser Glu Ala Ser Gly Arg Leu Ser Ala Leu Gly Arg Ser Pro Arg Leu
            20                  25                  30 gtg cgc gcg ggg tcc cgc atc ctg gac aag cta cag ttc ttc gaa gag    144
Val Arg Ala Gly Ser Arg Ile Leu Asp Lys Leu Gln Phe Phe Glu Glu
        35                  40                  45 cgg cga cgc agc ctg gag cgc agc gac tcg ccg cca gcg ccc ctg cgg    192
Arg Arg Arg Ser Leu Glu Arg Ser Asp Ser Pro Pro Ala Pro Leu Arg
    50                  55                  60 ccc tgg gtg ccc ctg cgc aag gct cgc tcg ctg gag cag ccg aag tcc    240
Pro Trp Val Pro Leu Arg Lys Ala Arg Ser Leu Glu Gln Pro Lys Ser
65                  70                  75                  80 gag ggc ggt gcg gcg tgg ggc aca ccc gag gcc tcg cag gag gag ctg    288
Glu Gly Gly Ala Ala Trp Gly Thr Pro Glu Ala Ser Gln Glu Glu Leu
                85                  90                  95 cgg tca cct cgg ggc agt gtg gca gag cgg cgt cgc ctg ttc cag caa    336
Arg Ser Pro Arg Gly Ser Val Ala Glu Arg Arg Arg Leu Phe Gln Gln
            100                 105                 110 aag gcg gcc tcg ttg gat gaa cgc acg cga caa cgc agt gca acc tcg    384
Lys Ala Ala Ser Leu Asp Glu Arg Thr Arg Gln Arg Ser Ala Thr Ser
        115                 120                 125 gac ctc gaa ctc cgc ttc gcc cag gag ctg ggt cgc atc cgc cga tct    432
Asp Leu Glu Leu Arg Phe Ala Gln Glu Leu Gly Arg Ile Arg Arg Ser
    130                 135                 140 acg tcg cgg gag gag ctg gtg cgt tcg cac gag tcc ctg cgt gcc acg    480
Thr Ser Arg Glu Glu Leu Val Arg Ser His Glu Ser Leu Arg Ala Thr
145                 150                 155                 160 ctg cag cgc gcc cca tcc cct cgg gag ccc ggc gag ccc cca ctc ttc    528
Leu Gln Arg Ala Pro Ser Pro Arg Glu Pro Gly Glu Pro Pro Leu Phe
                165                 170                 175
```

-continued

| | |
|---|---|
| tcc cgg cct tcc aca ccc aag acc tca cgg gct gtg agc ccg gct gcc<br>Ser Arg Pro Ser Thr Pro Lys Thr Ser Arg Ala Val Ser Pro Ala Ala<br>180                        185                      190 | 576 |
| acc cag ccg ccg cct cct agt ggt gcg ggc aaa tct ggg gac gag cct<br>Thr Gln Pro Pro Pro Ser Gly Ala Gly Lys Ser Gly Asp Glu Pro<br>       195                    200                    205 | 624 |
| ggg agg ccc cga agc aga ggg ccg gtg ggc agg act gaa ccg ggg gaa<br>Gly Arg Pro Arg Ser Arg Gly Pro Val Gly Arg Thr Glu Pro Gly Glu<br>210                        215                      220 | 672 |
| ggc ccg cag cag gag atc aag cgt cgg gac caa ttc ccg cta acc agg<br>Gly Pro Gln Gln Glu Ile Lys Arg Arg Asp Gln Phe Pro Leu Thr Arg<br>225                        230                    235                    240 | 720 |
| agc aga gcc atc cag gag tgc agg agc cct gtg ccg ccc tac acc gcg<br>Ser Arg Ala Ile Gln Glu Cys Arg Ser Pro Val Pro Pro Tyr Thr Ala<br>                  245                    250                    255 | 768 |
| gat ccc ccg gag agc agg aca aaa gcc ccc tcc ggt cgc aag cgg gaa<br>Asp Pro Pro Glu Ser Arg Thr Lys Ala Pro Ser Gly Arg Lys Arg Glu<br>       260                    265                    270 | 816 |
| ccc cct gct caa gcg gtg cgc ttt ctg ccc tgg gcc act ccg gga gtg<br>Pro Pro Ala Gln Ala Val Arg Phe Leu Pro Trp Ala Thr Pro Gly Val<br>275                        280                    285 | 864 |
| gag gac tct gtt ctg ccc caa acc ttg gag aag aat aga gcg gga ccc<br>Glu Asp Ser Val Leu Pro Gln Thr Leu Glu Lys Asn Arg Ala Gly Pro<br>290                        295                    300 | 912 |
| gag gct gag aag agg ctt cgc aga gga cct gag gag gat ggc ccc tgg<br>Glu Ala Glu Lys Arg Leu Arg Arg Gly Pro Glu Glu Asp Gly Pro Trp<br>305                        310                    315                    320 | 960 |
| ggg ccc tgg gac cgc aga ggg acc cgc agc caa ggc aaa ggt cgc cgt<br>Gly Pro Trp Asp Arg Arg Gly Thr Arg Ser Gln Gly Lys Gly Arg Arg<br>                  325                    330                    335 | 1008 |
| gct cgg cct act tcc ccc gag ctc gag tcc tca gac gac tcc tat gtg<br>Ala Arg Pro Thr Ser Pro Glu Leu Glu Ser Ser Asp Asp Ser Tyr Val<br>                340                    345                    350 | 1056 |
| tcc gct ggg gaa gag ccc ctg gag gca ccc gtg ttt gag atc cct ctg<br>Ser Ala Gly Glu Glu Pro Leu Glu Ala Pro Val Phe Glu Ile Pro Leu<br>355                        360                    365 | 1104 |
| cag aat atg gtg gtg gcg cca gga gct gac gtg cta ctt aag tgt atc<br>Gln Asn Met Val Val Ala Pro Gly Ala Asp Val Leu Leu Lys Cys Ile<br>370                        375                    380 | 1152 |
| atc acc gcc aac ccc cca ccc caa gtg tcc tgg aaa aag gat ggg tcc<br>Ile Thr Ala Asn Pro Pro Pro Gln Val Ser Trp Lys Lys Asp Gly Ser<br>385                        390                    395                    400 | 1200 |
| atg ttg cac agc gag ggt cgt ctt ctc atc cgg gct gaa ggt gaa cgg<br>Met Leu His Ser Glu Gly Arg Leu Leu Ile Arg Ala Glu Gly Glu Arg<br>                405                    410                    415 | 1248 |
| cac aca ctg ctg ctc aga gag gcc cag gct gct gat gct ggg agc tac<br>His Thr Leu Leu Leu Arg Glu Ala Gln Ala Ala Asp Ala Gly Ser Tyr<br>                420                    425                    430 | 1296 |
| aca gcc act gcc acc aac gaa ctg ggc caa gct acc tgt gct tct tca<br>Thr Ala Thr Ala Thr Asn Glu Leu Gly Gln Ala Thr Cys Ala Ser Ser<br>                  435                    440                    445 | 1344 |
| ctg gct gtg aga cct ggc ggc tcc aca tcc cct ttc agc agc ccc atc<br>Leu Ala Val Arg Pro Gly Gly Ser Thr Ser Pro Phe Ser Ser Pro Ile<br>450                        455                    460 | 1392 |
| acc tct gat gag gag tac ctg agc ccc cca gag gag ttc cca gag cct<br>Thr Ser Asp Glu Glu Tyr Leu Ser Pro Pro Glu Glu Phe Pro Glu Pro<br>465                        470                    475                    480 | 1440 |
| ggg gag acc tgg ccc cga acc cct acc atg aag ctc agt ccc agc cag<br>Gly Glu Thr Trp Pro Arg Thr Pro Thr Met Lys Leu Ser Pro Ser Gln | 1488 |

| | | | | | | | | | | | | | | | | |
|---|---|---|---|---|---|---|---|---|---|---|---|---|---|---|---|---|
| | | | 485 | | | | | 490 | | | | | 495 | | | |
| gat | cat | gat | tcc | tcc | gac | tct | tct | tcc | aag | gca | ccc | cca | acg | ttc | aag | 1536 |
| Asp | His | Asp | Ser | Ser | Asp | Ser | Ser | Ser | Lys | Ala | Pro | Pro | Thr | Phe | Lys | |
| | | | 500 | | | | | 505 | | | | | 510 | | | |
| gtc | tca | ctc | atg | gac | caa | tcg | gtg | aga | gaa | ggt | caa | gat | gtc | att | atg | 1584 |
| Val | Ser | Leu | Met | Asp | Gln | Ser | Val | Arg | Glu | Gly | Gln | Asp | Val | Ile | Met | |
| | | 515 | | | | | 520 | | | | | 525 | | | | |
| agc | atc | cgt | gtg | cag | gga | gag | ccc | aag | cct | gtg | gtt | tcc | tgg | ctg | agg | 1632 |
| Ser | Ile | Arg | Val | Gln | Gly | Glu | Pro | Lys | Pro | Val | Val | Ser | Trp | Leu | Arg | |
| | 530 | | | | | 535 | | | | | 540 | | | | | |
| aat | cga | cag | ccc | gtg | cgc | cca | gac | cag | cgg | cgc | ttt | gca | gag | gag | gcc | 1680 |
| Asn | Arg | Gln | Pro | Val | Arg | Pro | Asp | Gln | Arg | Arg | Phe | Ala | Glu | Glu | Ala | |
| 545 | | | | | 550 | | | | | 555 | | | | | 560 | |
| gag | ggt | ggg | ctc | tgc | cgc | ttg | agg | atc | ctg | gct | gct | gaa | cgg | ggc | gat | 1728 |
| Glu | Gly | Gly | Leu | Cys | Arg | Leu | Arg | Ile | Leu | Ala | Ala | Glu | Arg | Gly | Asp | |
| | | | | 565 | | | | | 570 | | | | | 575 | | |
| gct | ggt | ttc | tac | aca | tgc | aag | gcg | gtc | aac | gaa | tat | ggc | gct | cgg | cag | 1776 |
| Ala | Gly | Phe | Tyr | Thr | Cys | Lys | Ala | Val | Asn | Glu | Tyr | Gly | Ala | Arg | Gln | |
| | | | 580 | | | | | 585 | | | | | 590 | | | |
| tgc | gag | gcc | cgc | ctg | gag | gtc | cga | ggc | gag | tgagctcagg | gggccacctg | | | | | 1826 |
| Cys | Glu | Ala | Arg | Leu | Glu | Val | Arg | Gly | Glu | | | | | | | |
| | | 595 | | | | | 600 | | | | | | | | | |

```
cgctgccccc gctaccctcc gagctgcacc cctgtctcag gcacctctcg gacctcgctg    1886
tgtttcactg cctcctgccc acagacccag ccggctcgcc ggcccggact tagcccatgc    1946
tcccctttccc tccctagccc atacagcacc ctggggtaac ccaccgggcc cctgtggatc    2006
ctccctcccc aagtggatat gtggctgtgc agaccaggag gccccagaa ggactgagtg     2066
ttgggaaggg atggccatga ggggtgccaa gctccctcgg tctccccata gggagcatcc    2126
agcgagtgca tgtgctatgc tgctacaggc cactgtctgt ctatctgttt gtccgtctgt    2186
gtgtctgtga cagtcaggga agaaagcctt tgagctgagg tgggctaaga cagaataaga    2246
tgacagagca cagcatccat gagatgcagg ggttcagagg ggtcaggtac agtggatatg    2306
aggctctctg ggaaggggca gggcactgac catttcagaa atgggttta aatggcacaa     2366
cattttttat tccacaagag accaaaagct agaggtctag ggttaagccc tagctgctgg    2426
caagattagg accaagtggg gtaccttct ttacagacac atccgacacg cgctgtctga     2486
gaatgagaga ggtagccagg ctgaacacag gagcagggtc atagtggagg tggagatttg    2546
gaaacactat ttcgtagctc aaataaagtc cagtttgtac ccaaaaaaaa aaaaaaaaa     2606
aaaaaaaa                                                              2614
```

<210> SEQ ID NO 16
<211> LENGTH: 602
<212> TYPE: PRT
<213> ORGANISM: Mus musculus

<400> SEQUENCE: 16

```
Glu Phe Arg Leu Ala Gly Thr Val Glu Ser Arg Pro Gln Thr Pro Leu
 1               5                  10                  15

Ser Glu Ala Ser Gly Arg Leu Ser Ala Leu Gly Arg Ser Pro Arg Leu
            20                  25                  30

Val Arg Ala Gly Ser Arg Ile Leu Asp Lys Leu Gln Phe Phe Glu Glu
        35                  40                  45

Arg Arg Arg Ser Leu Glu Arg Ser Asp Ser Pro Ala Pro Leu Arg
    50                  55                  60

Pro Trp Val Pro Leu Arg Lys Ala Arg Ser Leu Glu Gln Pro Lys Ser
```

```
                65                  70                  75                  80
Glu Gly Gly Ala Ala Trp Gly Thr Pro Glu Ala Ser Gln Glu Glu Leu
                    85                  90                  95
Arg Ser Pro Arg Gly Ser Val Ala Glu Arg Arg Leu Phe Gln Gln
                100                 105                 110
Lys Ala Ala Ser Leu Asp Glu Arg Thr Arg Gln Arg Ser Ala Thr Ser
                115                 120                 125
Asp Leu Glu Leu Arg Phe Ala Gln Glu Leu Gly Arg Ile Arg Arg Ser
            130                 135                 140
Thr Ser Arg Glu Glu Leu Val Arg Ser His Glu Ser Leu Arg Ala Thr
145                 150                 155                 160
Leu Gln Arg Ala Pro Ser Pro Arg Glu Pro Gly Glu Pro Pro Leu Phe
                165                 170                 175
Ser Arg Pro Ser Thr Pro Lys Thr Ser Arg Ala Val Ser Pro Ala Ala
                180                 185                 190
Thr Gln Pro Pro Pro Ser Gly Ala Gly Lys Ser Gly Asp Glu Pro
                195                 200                 205
Gly Arg Pro Arg Ser Arg Gly Pro Val Gly Arg Thr Glu Pro Gly Glu
    210                 215                 220
Gly Pro Gln Gln Glu Ile Lys Arg Arg Asp Gln Phe Pro Leu Thr Arg
225                 230                 235                 240
Ser Arg Ala Ile Gln Glu Cys Arg Ser Pro Val Pro Tyr Thr Ala
                245                 250                 255
Asp Pro Pro Glu Ser Arg Thr Lys Ala Pro Ser Gly Arg Lys Arg Glu
                260                 265                 270
Pro Pro Ala Gln Ala Val Arg Phe Leu Pro Trp Ala Thr Pro Gly Val
            275                 280                 285
Glu Asp Ser Val Leu Pro Gln Thr Leu Glu Lys Asn Arg Ala Gly Pro
290                 295                 300
Glu Ala Glu Lys Arg Leu Arg Arg Gly Pro Glu Glu Asp Gly Pro Trp
305                 310                 315                 320
Gly Pro Trp Asp Arg Arg Gly Thr Arg Ser Gln Gly Lys Gly Arg Arg
                325                 330                 335
Ala Arg Pro Thr Ser Pro Glu Leu Glu Ser Ser Asp Asp Ser Tyr Val
                340                 345                 350
Ser Ala Gly Glu Glu Pro Leu Glu Ala Pro Val Phe Glu Ile Pro Leu
                355                 360                 365
Gln Asn Met Val Val Ala Pro Gly Ala Asp Val Leu Leu Lys Cys Ile
                370                 375                 380
Ile Thr Ala Asn Pro Pro Pro Gln Val Ser Trp Lys Lys Asp Gly Ser
385                 390                 395                 400
Met Leu His Ser Glu Gly Arg Leu Leu Ile Arg Ala Glu Gly Glu Arg
                405                 410                 415
His Thr Leu Leu Leu Arg Glu Ala Gln Ala Ala Asp Ala Gly Ser Tyr
                420                 425                 430
Thr Ala Thr Ala Thr Asn Glu Leu Gly Gln Ala Thr Cys Ala Ser Ser
                435                 440                 445
Leu Ala Val Arg Pro Gly Gly Ser Thr Ser Pro Phe Ser Ser Pro Ile
                450                 455                 460
Thr Ser Asp Glu Glu Tyr Leu Ser Pro Pro Glu Glu Phe Pro Glu Pro
465                 470                 475                 480
Gly Glu Thr Trp Pro Arg Thr Pro Thr Met Lys Leu Ser Pro Ser Gln
                485                 490                 495
```

-continued

```
Asp His Asp Ser Ser Asp Ser Ser Lys Ala Pro Pro Thr Phe Lys
            500                 505                 510

Val Ser Leu Met Asp Gln Ser Val Arg Glu Gly Gln Asp Val Ile Met
        515                 520                 525

Ser Ile Arg Val Gln Gly Glu Pro Lys Pro Val Val Ser Trp Leu Arg
    530                 535                 540

Asn Arg Gln Pro Val Arg Pro Asp Gln Arg Arg Phe Ala Glu Glu Ala
545                 550                 555                 560

Glu Gly Gly Leu Cys Arg Leu Arg Ile Leu Ala Ala Glu Arg Gly Asp
                565                 570                 575

Ala Gly Phe Tyr Thr Cys Lys Ala Val Asn Glu Tyr Gly Ala Arg Gln
            580                 585                 590

Cys Glu Ala Arg Leu Glu Val Arg Gly Glu
    595                 600
```

<210> SEQ ID NO 17
<211> LENGTH: 2738
<212> TYPE: DNA
<213> ORGANISM: Mus musculus

<400> SEQUENCE: 17

```
gcgatagata acctggtgat ccaaacctgt aatcctaact actgtggagg ctgagataat      60
aacttgccag agatacagag tcagttcaag accaccctag caactaaag agatcttgtt     120
tcagactaag aaaagaggc ctagcaaggc cctacattca atcccccaga acaaatgac      180
tcagacagcc caagtccaga ctgtaaatca gagactacag gggaccatac cccaaagaac    240
tctctagaat tcctgtgctc agaaaacttt gaaacccaat caaccaaact gggcagtggt    300
gtcacatgct tttaatccca gtactcagga ggcagaggca ggcagatctc tgagttcaag    360
tccagcctga tttactgatt gagtcaaggc tacacagaga taccctgtct caaaaaacta    420
acaagcaaaa tacaaaaaca aaaccaaaa aaaaaaaaaa aaaaaaaaaa aaaataagaa    480
gcccaaccat ataagaagca ttttgaaaaa aaactaatgt ttgaaatcgc tggcatgggg    540
ttaaagatct agttcaaatt gggaagctgg ctgctgtcat tggaatcaca agggctgtcg    600
aaccagactt agggatttac agccctgctc tgaagttgaa tggccaagag ctgtgagatt    660
cagtgaaatc acctcttaga gttcccatcc tcccatgagg atttgcctag gtctcaaaac    720
ttccatgtgc ctagggatct ctagagtgct tttgaaaaaa aattacagtg ttcgactcct    780
cactttagaa aatcaattct gtaggctgga taaggtctaa gaatctgtat ttcaaaacaa    840
gccccaagtg gtacccgtgt gggtggttca agcatcacgc acacagtcct ggtgtagatg    900
gccttgggtg atgctatccg tgtgctagaa actgggtgtc tgtcgtgaag agactacaga    960
cagctgggat gtcaggcttg actggatata ctggcctggg ggaaattcct gcttgtgggc    1020
tgtctaatgc cagttcttat tgaatgatac tggcctgaaa gaactgtcca agggcagct   1080
agatgaatag agtcagctca tggagagctg ggtcaaatgt aatgaagtgg tcctttaatg    1140
ggaaggtttg ggatcaaaag aacactgccc ttgctggtgt tatctcccac agtgaaatct    1200
gggtttgtag atggatcagg cttgggatgt tacaaaaaaa tggctacaaa gttgctttag    1260
cccatgcggt ctgcagggct tgggattcta cagcttggtg gtgtactttg gggttatggc    1320
tggaacagag gccacttctt tttctcagag aggcattcca ttggagcttg agcctgcagc    1380
ctgacaagca atctcgccaa gactcttgac ctaggcttgc tgctgattgg ctggctagca    1440
cctaggttct atttccctgc tggccaccag gggtctctga agcaaacata gacctttggc    1500
```

-continued

```
aattcgagtt aaatgtttgc cccgccctcc tttccttagc ctgggagctt gcctcagcac    1560
tgtccagcct ggaggtgacc ctggagccag gaatctaaac tctgtagagg gaaaggagtc    1620
ccctcttcca agggctgtgc ctatgacctc agtatcagct ggtggccacg cccccggcca    1680
caaatgccat tcggatttct ctctcctccc caaccttgag actgccagcc tgaaagtggg    1740
ctgtcctctt ggcccccaca cttcttcatc actggcagtg ctggggaaca caggtcatag    1800
cttgggaatg tggccctggg tggagagagg ggatcaagga gggagagaga tttgtggcct    1860
ctgctcaaca cctctgcttc tattattctt cctgagcccc ttccctaccc actgggtgca    1920
aacggaagct ggggaggagc gaccattggg gaggagcggc ccacacttcc ctagctttga    1980
gccctggtgg gctgagggt gagggcagt ttgccagcag aaattcagta gaacccatgg      2040
ttgagcaggg tgcaggcctg tgtcctgaag tacctgctct cctgaacttg tctagggcag    2100
gacctgggag tctgcagcca tgggctcagt ttccttaggt tggcagggga caaatctgga    2160
aaggagggtc aagccctgac agttcttttgg ttctctgtgt ctgaaaaagc tggttgtggc   2220
ctatttgggg gtttaaggct ggctagttat gtattcctag gtcaggattc ttcttggttt    2280
gggcaaagca tggcgcttgc tgtgctgtat gggtcaacac ttctggccca ggcaaggata    2340
ttaaatgccg cagtgcagtg ccacccctta gaccctctg aggaccgggg tccccacacc     2400
tgtagtctag gccctactga tgggttcagc tcttgtcagt gtcccaagct gtaaggagag    2460
gaaaggcaga cagctagctg cttggaatga tcagagtcta aattcagctg gtctgggctc    2520
cgcccctccc ccgttcctat tccaccactc caggggctgc tccctgtggt ctcagcaggc    2580
accaccttcc cagccagcgc ctgcctgctg cccagcctct tgctggccac cccaccctcc    2640
tccttccccc gctcctaggc tcacttcccc tcccccagg gctggctcag tgcggggcct    2700
cagctgggtc agcgagtgag tggggctggc caggctga                           2738
```

<210> SEQ ID NO 18
<211> LENGTH: 113
<212> TYPE: PRT
<213> ORGANISM: Homo sapiens

<400> SEQUENCE: 18

```
Met Lys Leu Ser Pro Ser Gln Asp His Asp Ser Ser Asp Ser Ser Ser
 1               5                  10                  15

Lys Ala Pro Pro Thr Phe Lys Val Ser Leu Met Asp Gln Ser Val Arg
             20                  25                  30

Glu Gly Gln Asp Val Ile Met Ser Ile Arg Val Gln Gly Glu Pro Lys
         35                  40                  45

Pro Val Val Ser Trp Leu Arg Asn Arg Gln Pro Val Arg Pro Asp Gln
     50                  55                  60

Arg Arg Phe Ala Glu Glu Ala Glu Gly Gly Leu Cys Arg Leu Arg Ile
 65                  70                  75                  80

Leu Ala Ala Glu Arg Gly Asp Ala Gly Phe Tyr Thr Cys Lys Ala Val
                 85                  90                  95

Asn Glu Tyr Gly Ala Arg Gln Cys Glu Ala Arg Leu Glu Val Arg Gly
            100                 105                 110

Glu
```

<210> SEQ ID NO 19
<211> LENGTH: 114
<212> TYPE: PRT
<213> ORGANISM: Artificial Sequence

```
<220> FEATURE:
<223> OTHER INFORMATION: synthetic consensus sequence
<220> FEATURE:
<221> NAME/KEY: VARIANT
<222> LOCATION: (1)...(114)
<223> OTHER INFORMATION: Xaa = Any Amino Acid

<400> SEQUENCE: 19

Met Lys Xaa Ser Pro Ser Gln Asp Xaa Xaa Ser Ser Asp Xaa Xaa Ser
 1               5                  10                  15

Lys Ala Pro Pro Thr Phe Lys Val Ser Leu Met Asp Gln Ser Val Arg
                20                  25                  30

Glu Gly Gln Asp Val Ile Met Ser Ile Arg Val Gln Gly Glu Pro Lys
            35                  40                  45

Pro Val Val Ser Trp Leu Arg Asn Arg Gln Pro Val Arg Pro Asp Gln
     50                  55                  60

Arg Arg Phe Ala Glu Glu Ala Glu Gly Gly Leu Cys Arg Leu Arg Ile
65                  70                  75                  80

Leu Ala Ala Glu Arg Gly Asp Ala Gly Phe Tyr Thr Cys Lys Ala Val
                85                  90                  95

Asn Glu Tyr Gly Ala Arg Gln Cys Glu Ala Arg Leu Glu Val Arg Gly
            100                 105                 110

Glu Xaa

<210> SEQ ID NO 20
<211> LENGTH: 73
<212> TYPE: DNA
<213> ORGANISM: Mus musculus

<400> SEQUENCE: 20
tcccctcccc ccagggctgg ctcagtgcgg ggcctcagct gggtcagcga gtgagtgggg      60
ctggccaggc tga                                                         73

<210> SEQ ID NO 21
<211> LENGTH: 18
<212> TYPE: DNA
<213> ORGANISM: Mus musculus

<400> SEQUENCE: 21
gggcctcagc tgggtcag                                                    18

<210> SEQ ID NO 22
<211> LENGTH: 18
<212> TYPE: DNA
<213> ORGANISM: Mus musculus

<400> SEQUENCE: 22
gggcctcagc acggtcag                                                    18

<210> SEQ ID NO 23
<211> LENGTH: 39
<212> TYPE: DNA
<213> ORGANISM: Mus musculus

<400> SEQUENCE: 23
tcagctgggt cagcgagtga gtggggctgg ccaggctga                             39

<210> SEQ ID NO 24
<211> LENGTH: 3487
<212> TYPE: DNA
<213> ORGANISM: Mus musculus
```

<400> SEQUENCE: 24

```
gagctctgcc tgcctctgcc tctcaagcgc tgggattaaa agtgtgtgac accatggccc      60
tattgccccc tttcttagtt tatcacccat gtccattcct aaacagtctg caggcctctg     120
agcctatact ttctacctca catagtttgt tgccttagtt tctctaaagc aagctctaat     180
ttaaatacca catcttccct cattcccaga gccaagagtc acctgtatgt atgaccctta     240
ttggctcctc cctgtccact cagcctctgt cctgctcacc attatatatt gtatattaat     300
ctatgttata tattatagtg tctttcttat caagtcaaag tcccctgact acacaactgt     360
cttttccaca ccttggtcct cgaagccatg cttggagaca ctgctagatt gattgtggac     420
cacagaactt ggggatgagg ggagaggaat aagggaagca ttgtccaggg agttcaagcc     480
atgagcactc cctgagtagc ctgtggatgc taaggaggac acacagtaat aaggctgtgt     540
ttgagagggg aggttgggat ggcagcagaa actataggcc atagagatgt ggttccatga     600
gccctcaaaa gcatcagcac acacacacac acacacacac acacacacac acacacacac     660
acacacacga gattgcgata gataacctgg gatccaaacc tgtaatccta actactgtgg     720
aggctgagat aataacttgc cagagataca gagtcagttc aagaccaccc taggcaacta     780
aagagatctt gtttcagact aagaaaaaga ggcctagcaa ggccctacat tcaatccccc     840
agaaacaaat gactcagaca gcccaagtcc agactgtaaa tcagagacta caggggacca     900
taccccaaag aactctctag aattcctgtg ctcagaaaac tttgaaaccc aatcaaccaa     960
actgggcagt ggtgtcacat gcttttaatc ccagtactca ggaggcagag gcaggcagat    1020
ctctgagttc aagtccagcc tgatttactg attgagtcaa ggctacacag agataccctg    1080
tctcaaaaaa ctaacaagca aaatacaaaa acaaaaacca aaaaaaaaa aaaaaaaaa     1140
aaaaaaataa gaagcccacc atataagaag cattttgaaa aaaaaactaa tgtttgaaat    1200
cgctggcatg gggttaaaga tctagttcaa attgggaagc tggctgctgt cattggaatc    1260
acaagggctg tcgaaccaga cttagggatt tacagccctg ctctgaagtt gaatggccaa    1320
gagctgtgag attcagtgaa atcacctctt agagttccca tcctccatga ggatttgcct    1380
aggtctcaaa acttccatgt cctaggatct ctagagtgct tttgaaaaaa aattacagtg    1440
ttcgactcct cactttagaa aatcaattct gtaggctgga taaggtctaa gaatctgtat    1500
ttcaaaacaa gccccagtgg tacccgtgtg ggtggttcaa gcatcacgca cacagtcctg    1560
gtgtagatgg ccttgggtga tgctatccgt gtctagaaac tgggtgtctg tcgtgaagag    1620
actacagaca gctgggatgt caggcttgac tgatatactg gcctggggga aattcctgct    1680
tgtgggctgt ctaatgccag ttcttattga atgatactgg cctgaaagaa ctgtccaaag    1740
ggcagctaga tgaatagagt cagctcatgg agagctgggt caaatgtaat gaagtggtcc    1800
tttaatggga aggtttggga tcaaaagaac actgcccttg ctggtgttat ctcccacagt    1860
gaaatctggg tttgtagatg gatcaggctt gggatgttac aaaaaatggc tacaaagttg    1920
ctttagccca tgcggtctgc agggcttggg attctacagc ttggtggtgt actttgggat    1980
tatggctgga acagaggcca cttcttttc tcagagaggc attccattgg agcttgagcc    2040
tgcagcctga caagcaatct cgccaagact cttgacctag gcttgctgct gattggctgg    2100
ctagcaccta ggttctattt ccctgctggc caccagggt ctctgaagca aacatagacc    2160
tttggcaatt cgagttaaat gtttgccccg ccctcctttc cttagcctgg gagcttgcct    2220
cagcactgtc cagcctggag gtgaccctgg agccaggaat ctaaactctg tagagggaaa    2280
```

-continued

```
ggagtcccct cttccaaggg ctgtgcctat gacctcagta tcagctggtg gccacgcccc    2340
cggccacaaa tgccattcgg atttctctct cctccccaac cttgagactg ccagcctgaa    2400
agtgggctgt cctcttggcc cccacacttc ttcatcactg gcagtgctgg ggaacacagg    2460
tcatagcttg ggaatgtggc cctgggtgga gagagggat caaggaggga gagagatttg     2520
tggcctctgc tcaacacctc tgcttctatt attcttcctg agccccttcc ctaccactgg    2580
tgcaaacgga agctggggag gagcgaccat tggggaggag cggcccacac ttccctagct    2640
ttgagccctg gtgggctgag gggtgagggg cagttgccag cagaaattca gtagaaaccc    2700
atggtgtagc aggtgtcagg cctgtgtcct gaagtacctg ctctcctgaa cttgtctagg    2760
gcaggacctg ggaagtcagc catgggctca gtttccttag gttggcaggg gacaaatctg    2820
gaaaggaggg tcaagccctg acagttcttt ggttctctgt gtctgaaaaa gctggttgtg    2880
gcctatttgg gggtttaagg ctggctagtt atgtattcct aggtcaggat tcttcttggt    2940
ttgggcaaag catggcgctt gctgtgctgt atgggtcaac acttctggcc caggcaagga    3000
tattaaatgc cgcagtgcag tgccacccct tagaccoctc tgaggaccttg gctgtgctgt    3060 atgggtcaac acttctggcc caggcaagga tattaaatgc cgcagtgcag tgccaccctt    3120 agaccctct gaggaccggg gtccccacac ctgtagtcta ggccctactg atgggttcag     3180
ctcttgtcag gtcccaagct gtaaggagag gaaaggcaga cagctagctg cttggaatga    3240
tcagagtcta aattcagctg gtctgggctc cgcccctccc ccgttcctat tccaccactc    3300
caggggctgc tccctgtggt ctcagcaggc accaccttcc cagccagcgc ctgcctgctg    3360
cccagcctct tgctggccac ccccacctcc tccttccccg ctcctaggct cacttcccct    3420 cccccaggg ctggctcagt gcggggcctc agctgggtca gcgagtgagt ggggctggcc     3480
aggctga                                                              3487
```